US008738395B2

(12) United States Patent
Hyde et al.

(10) Patent No.: US 8,738,395 B2
(45) Date of Patent: *May 27, 2014

(54) METHODS AND SYSTEMS FOR PRESENTING AN INHALATION EXPERIENCE

(75) Inventors: Roderick A. Hyde, Redmond, WA (US); Robert Langer, Newton, MA (US); Eric C. Leuthardt, St. Louis, MO (US); Robert W. Lord, Seattle, WA (US); Elizabeth A. Sweeney, Seattle, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 768 days.

This patent is subject to a terminal disclaimer.

(21) Appl. No.: 12/386,669

(22) Filed: Apr. 21, 2009

(65) Prior Publication Data

US 2010/0163028 A1  Jul. 1, 2010

Related U.S. Application Data

(63) Continuation-in-part of application No. 12/317,934, filed on Dec. 30, 2008, and a continuation-in-part of application No. 12/319,143, filed on Dec. 31, 2008, and a continuation-in-part of application No. 12/378,284, filed on Feb. 12, 2009, and a continuation-in-part of application No. 12/378,485, filed on Feb. 13, 2009, and a continuation-in-part of application No. 12/380,013, filed on Feb. 20, 2009, and a continuation-in-part of application No. 12/380,108, filed on Feb. 23, 2009, and a continuation-in-part of application No. 12/380,587, filed on Feb. 27, 2009, and a continuation-in-part of application No. 12/380,679, (Continued)

(51) Int. Cl.
G06Q 10/00 (2012.01)
G06F 19/00 (2011.01)
A61M 11/00 (2006.01)

(52) U.S. Cl.
USPC .............. 705/2; 702/19; 128/200.15

(58) Field of Classification Search
USPC ........................................... 705/2
See application file for complete search history.

(56) References Cited

U.S. PATENT DOCUMENTS 3,946,726 A  3/1976 Pikul
4,652,261 A  3/1987 Mech et al.
(Continued)

FOREIGN PATENT DOCUMENTS

EP  0328145  8/1989

OTHER PUBLICATIONS

U.S. Appl. No. 12/387,057, Hyde et al.
(Continued)

Primary Examiner — Hiep V Nguyen

(57) ABSTRACT

Methods, computer program products, and systems are described that include monitoring at least one health attribute of an individual during an artificial sensory experience, associating a characteristic of the artificial sensory experience with the at least one health attribute of the individual, and modifying at least one of an inhalation device-dispensed bioactive agent or the artificial sensory experience at least partially based on associating a characteristic of the artificial sensory experience with the at least one health attribute of the individual.

39 Claims, 37 Drawing Sheets

Related U.S. Application Data filed on Mar. 2, 2009, and a continuation-in-part of application No. 12/383,509, filed on Mar. 25, 2009, and a continuation-in-part of application No. 12/383,819, filed on Mar. 26, 2009, and a continuation-in-part of application No. 12/384,104, filed on Mar. 31, 2009, and a continuation-in-part of application No. 12/384,203, filed on Apr. 1, 2009, and a continuation-in-part of application No. 12/386,574, filed on Apr. 20, 2009.

(56) References Cited

U.S. PATENT DOCUMENTS

| | | | |
|---|---|---|---|
| 4,784,162 | A | 11/1988 | Ricks et al. |
| 4,974,729 | A | 12/1990 | Steinnagel |
| 5,071,704 | A | 12/1991 | Fischel-Ghodsian |
| 5,455,043 | A | 10/1995 | Fischel-Ghodsian |
| 5,458,853 | A | 10/1995 | Porter et al. |
| 5,487,378 | A | 1/1996 | Robertson et al. |
| 5,546,943 | A | 8/1996 | Gould |
| 5,610,674 | A * | 3/1997 | Martin ............................ 352/85 |
| 5,709,863 | A | 1/1998 | Pageat |
| 5,725,472 | A | 3/1998 | Weathers |
| 5,822,726 | A | 10/1998 | Taylor et al. |
| 5,842,467 | A | 12/1998 | Greco |
| 5,954,641 | A | 9/1999 | Kehr et al. |
| 6,026,807 | A | 2/2000 | Puderbaugh et al. |
| 6,067,523 | A | 5/2000 | Bair et al. |
| 6,168,562 | B1 | 1/2001 | Miller et al. |
| 6,223,744 | B1 | 5/2001 | Garon |
| 6,280,383 | B1 | 8/2001 | Damadian |
| 6,314,384 | B1 | 11/2001 | Goetz |
| 6,315,719 | B1 | 11/2001 | Rode et al. |
| 6,338,338 | B1 | 1/2002 | Brace |
| 6,411,905 | B1 | 6/2002 | Guoliang et al. |
| 6,425,764 | B1 | 7/2002 | Lamson |
| 6,443,153 | B1 | 9/2002 | Viljanen et al. |
| 6,491,643 | B2 | 12/2002 | Katzman et al. |
| 6,500,862 | B1 | 12/2002 | Zanello |
| 6,513,523 | B1 | 2/2003 | Izuchukwu et al. |
| 6,585,519 | B1 | 7/2003 | Jenkins et al. |
| 6,609,068 | B2 | 8/2003 | Cranley et al. |
| 6,647,358 | B2 | 11/2003 | Grass et al. |
| 6,684,880 | B2 | 2/2004 | Trueba |
| 6,780,171 | B2 | 8/2004 | Gabel et al. |
| 6,783,753 | B2 | 8/2004 | Rabinowitz et al. |
| 6,860,239 | B1 | 3/2005 | Begun |
| 6,889,687 | B1 | 5/2005 | Olsson |
| 6,978,212 | B1 | 12/2005 | Sunshine |
| 6,981,502 | B2 | 1/2006 | McCormick et al. |
| 7,044,911 | B2 * | 5/2006 | Drinan et al. .................. 600/300 |
| 7,155,680 | B2 | 12/2006 | Akazawa et al. |
| 7,198,044 | B2 * | 4/2007 | Trueba ...................... 128/200.16 |
| 7,353,065 | B2 * | 4/2008 | Morrell ............................ 607/45 |
| 7,373,377 | B2 | 5/2008 | Altieri |
| 7,383,837 | B2 | 6/2008 | Robertson et al. |
| 7,427,417 | B2 | 9/2008 | Jendrucko et al. |
| 7,447,541 | B2 | 11/2008 | Huiku et al. |
| 7,720,696 | B1 | 5/2010 | Berger et al. |
| 8,068,983 | B2 | 11/2011 | Vian et al. |
| 2001/0006939 | A1 | 7/2001 | Niven et al. |
| 2001/0034023 | A1 | 10/2001 | Stanton, Jr. et al. |
| 2002/0084996 | A1 | 7/2002 | Temkin et al. |
| 2003/0032638 | A1 | 2/2003 | Kim et al. |
| 2003/0036683 | A1 | 2/2003 | Kehr et al. |
| 2003/0114475 | A1 | 6/2003 | Fox et al. |
| 2004/0107961 | A1 | 6/2004 | Trueba |
| 2004/0116784 | A1 | 6/2004 | Gavish |
| 2004/0254501 | A1 | 12/2004 | Mault |
| 2005/0054942 | A1 | 3/2005 | Melker et al. |
| 2005/0115561 | A1 | 6/2005 | Stahmann et al. |
| 2005/0220843 | A1 | 10/2005 | DeWitt et al. |
| 2006/0031099 | A1 | 2/2006 | Vitello et al. |
| 2006/0058694 | A1 | 3/2006 | Clark et al. |
| 2006/0207596 | A1 | 9/2006 | Lane |
| 2007/0068514 | A1 | 3/2007 | Giroux |
| 2007/0068515 | A1 | 3/2007 | Churchill |
| 2007/0112624 | A1 | 5/2007 | Jung et al. |
| 2007/0123783 | A1 | 5/2007 | Chang |
| 2008/0014566 | A1 | 1/2008 | Chapman et al. |
| 2008/0038701 | A1 | 2/2008 | Booth et al. |
| 2008/0087279 | A1 | 4/2008 | Tieck et al. |
| 2008/0142010 | A1 | 6/2008 | Weaver et al. |
| 2008/0172044 | A1 | 7/2008 | Shelton |
| 2008/0209289 | A1 | 8/2008 | Farnsworth et al. |
| 2008/0230057 | A1 | 9/2008 | Sutherland |
| 2008/0294012 | A1 | 11/2008 | Kurtz et al. |
| 2008/0318913 | A1 | 12/2008 | Fox et al. |
| 2009/0171259 | A1 | 7/2009 | Soerensen et al. |
| 2009/0223249 | A1 | 9/2009 | Julkowski et al. |
| 2009/0306741 | A1 | 12/2009 | Hogle et al. |
| 2011/0226242 | A1 | 9/2011 | Von Hollen et al. |

OTHER PUBLICATIONS

U.S. Appl. No. 12/387,151, Hyde et al.
U.S. Appl. No. 12/387,321, Hyde et al.
U.S. Appl. No. 12/387,472, Hyde et al.
Dog Health: Asthma, http://www.animalhospitals-usa.com/dogs/asthma.html, 2009, Publisher: Harper Collins.
Karen Vail, Chemical and Nonchemical Management of Fleas, 1999, Publisher: facilities.lipscomb.edu/media.asp?145&UKEY=7743, Published in: US.
Julian R. Yates III, *Ctenocephalides felis* (Bouche), http://www.extento.hawaii.edu/kbase/urban/site/catflea.htm, , Published in: US.
Mehlhorn, et al., Effects of Imidacloprid on Adult and Larval Stages of the Flea *Ctenocephalides felis* After In Vivo and In Vitro Applicat, Parasitology Research, 1999, pp. 625-637, vol. 85, No. 8-9, Published in: US.
Susan Little, Feline Asthma, The Winn Feline Foundation, 2003, Publisher: http://www.winnfelinehealth.org/health/asthma.html, Published in: US.
Placerville Veterinary Clinic, Flea Control, www://placervillevet.com/flea_control.htm, 1995-2008, Published in: US.
Cranshaw, et al., Fleas and Plague, http://www.ext.colostate.edu/pubs/insect/05600.html, 2008, Published in: US.
Jeff Feinman, VMD,CVH, Fleas and Ticks, http://www.homevet.com/petcare/fleas.html, 1996-1997, Published in: US.
Omar S. Usmani, et al., Glucocorticoid Receptor Nuclear Translocation in Airway Cells After Inhaled Combination Therapy, American Journal of Respiratory and Critical Care Medicine, Apr. 28, 2005, pp. 704-712, vol. 172, Published in: US; printed from http://ajrccm.atsjournals.org/cgi/content/abstract/172/6/704.
J.B. Siddall, Insect Growth Regulators and Insect Control: A Critical Appraisal, Environmental Health Perspectives, Apr. 1976, pp. 119-126, vol. 14, Published in: US.
Label Instructions Tightened on Flea & Tick Control Products for Pets, http://www.epa.gov/pesticides/factsheets/hartzq_a.htm, Nov. 2002, Publisher: Environmental Protection Agency, Published in: US.
T. Roy Fukuto, Mechanism of Action of Organophosphorus and Carbamate Insecticides, Environmental Health Perspectives, Jul. 1990, pp. 245-254, vol. 87, Published in: US.
M. Tomizawa, et al., Neonicotinoid Insecticide Toxicology: Mechanisms of Selective Action, Annual Review of Pharmacology and Toxicology, Feb. 2005, pp. 247-268, vol. 45.
C.J. Harland, et al., Remote Detection of Human Electroencephalograms Using Ultrahigh Input Impedance Electric Potential Sensors, Applied Physics Letters, Oct. 21, 2002, pp. 3284-3286, vol. 81, No. 17, Publisher: American Institute of Physics.
Mencke, et al., Therapy and Prevention of Parasitic Insects in Veterinary Medicine Using Imidacloprid, Current Topics in Medicinal Chemistry, Jul. 2002, vol. 2, No. 7.
Hovda, et al., Toxicology of Newer Pesticides for Use in Dogs and Cats, Vet Clin North Am Small Anim. Pract., Mar. 2002, pp. 455-567, vol. 32, No. 2.
"Fear of Flying"; The Virtual Reality Medical Center (VRMC); Bearing a date of Jan. 1, 2007, p. 1; located at: http://www.vrphobia.com/therapy.htm.

* cited by examiner

600

Start 610
accepting an indication of a bioactive agent-dispensing inhalation device 620
presenting an indication of an artificial sensory experience at least partially based on accepting an indication of a bioactive agent-dispensing inhalation device Finish

FIG. 6

```
                                                                    600
                          ┌─────┐                                  ↙
                          │Start│
                          └─────┘
```

610
accepting an indication of a bioactive agent-dispensing inhalation device

| 702 accepting an indication of a bioactive agent-dispensing inhalation device configured to interface with a computing device<br><br>704 accepting an indication of a bioactive agent-dispensing inhalation device configured to interface wirelessly with a computing device | 706 accepting an indication of a bioactive agent-dispensing inhalation collar | 708 accepting an indication of a bioactive agent-dispensing virtual-reality headset |

620
presenting an indication of an artificial sensory experience at least partially based on accepting an indication of a bioactive agent-dispensing inhalation device

```
                          ┌──────┐
                          │Finish│
                          └──────┘
```

Start 610
accepting an indication of a bioactive agent-dispensing inhalation device 802
accepting at least one of a bioactive agent dosing schedule or a bioactive agent administration schedule 804
accepting an indication of a medicine-dispensing inhalation device 806
accepting an indication of a prescription medicine-dispensing inhalation device 808
accepting an indication of at least one of a steroid, a bronchodilator, menthol, nitrous oxide, a benzodiazepine, an anti-allergic agent, a muscle relaxant, or anesthetic 620
presenting an indication of an artificial sensory experience at least partially based on accepting an indication of a bioactive agent-dispensing inhalation device Finish

FIG. 8

```
┌─────────────────────────────────────────────────────────────────────┐
│ 610                                                                 │
│ accepting an indication of a bioactive agent-dispensing inhalation device │
│ ┌─────────────────────┐ ┌───────────────────────────────────────┐ │
│ │ 902                 │ │ 904                                   │ │
│ │ accepting        an │ │ accepting an indication of a recreational │
│ │ indication of    an │ │ bioactive agent-dispensing inhalation device │
│ │ unregulated bioactive│ ├───────────────────────────────────────┤ │
│ │ agent-dispensing    │ │ 906                                   │ │
│ │ inhalation device   │ │ accepting an indication of at least one │
│ │                     │ │ artificial smoke or an aroma compound │ │
│ └─────────────────────┘ └───────────────────────────────────────┘ │
└─────────────────────────────────────────────────────────────────────┘

┌─────────────────────────────────────────────────────────────────────┐
│ 620                                                                 │
│ presenting an indication of an artificial sensory experience at least partially │
│ based on accepting an indication of a bioactive agent-dispensing inhalation │
│ device                                                              │
└─────────────────────────────────────────────────────────────────────┘
```

FIG. 9

```
┌─────────────────────────────────────────────────────────────────────────┐
│ 610                                                                     │
│ accepting an indication of a bioactive agent-dispensing inhalation device│
└─────────────────────────────────────────────────────────────────────────┘

┌─────────────────────────────────────────────────────────────────────────┐
│ 620                                                                     │
│ presenting an indication of an artificial sensory experience at least partially │
│ based on accepting an indication of a bioactive agent-dispensing inhalation │
│ device                                                                  │
│  ┌───────────────────────────────────────────────────────────────────┐ │
│  │ 1002 presenting an indication of a prescribed artificial sensory experience │ │
│  │ ┌──────────────┬──────────────────────────────────────────────┐  │ │
│  │ │ 1004         │ 1006                                         │  │ │
│  │ │ presenting an│ presenting an indication of at least one effect of the │ │
│  │ │ indication of a│ prescribed artificial sensory experience   │  │ │
│  │ │ virtual world│ ┌──────────────────┬──────────────────────┐ │  │ │
│  │ │ experience, a│ │ 1008             │ 1010                 │ │  │ │
│  │ │ massively    │ │ presenting an indication│ presenting an indication │ │
│  │ │ multiplayer  │ │ of at least one desired│ of at least one expected │ │
│  │ │ online game, or│ effect of the prescribed│ adverse effect of the │ │
│  │ │ a learning   │ │ artificial sensory│ prescribed artificial │ │  │ │
│  │ │ tutorial     │ │ experience       │ sensory experience   │ │  │ │
│  │ │              │ └──────────────────┴──────────────────────┘ │  │ │
│  │ └──────────────┴──────────────────────────────────────────────┘  │ │
│  └───────────────────────────────────────────────────────────────────┘ │
└─────────────────────────────────────────────────────────────────────────┘
```

FIG. 10

```
                                                          600
                            ┌─────┐                      ↙
                           (Start)
                            └──┬──┘

┌──────────────────────────────┴──────────────────────────────┐
│ 610                                                         │
│ accepting an indication of a bioactive agent-dispensing inhalation device │
└──────────────────────────────┬──────────────────────────────┘

┌──────────────────────────────┴──────────────────────────────────────┐
│ 620                                                                 │
│ presenting an indication of an artificial sensory experience at least partially │
│ based on accepting an indication of a bioactive agent-dispensing inhalation │
│ device                                                              │
│ ┌─────────────────────────────────────────────────────────────────┐ │
│ │ 1002 presenting an indication of a prescribed artificial sensory experience │ │
│ │ ┌─────────────┐ ┌─────────────────┐ ┌─────────────────┐ │ │
│ │ │ 1102        │ │ 1104            │ │ 1106            │ │ │
│ │ │ presenting an│ │ presenting an indication│ │ recommending an │ │ │
│ │ │ indication of at least│ │ of at least one time│ │ artificial sensory│ │ │
│ │ │ one time period of│ │ period of an expected│ │ experience       │ │ │
│ │ │ an expected change│ │ change in bioactive│ │ administration   │ │ │
│ │ │ in bioactive agent│ │ agent blood│ │ schedule         │ │ │
│ │ │ effectiveness│ │ concentration│ │                 │ │ │
│ │ └─────────────┘ └─────────────────┘ └─────────────────┘ │ │
│ └─────────────────────────────────────────────────────────────────┘ │
└──────────────────────────────┬──────────────────────────────────────┘
                            ┌──┴───┐
                           (Finish)
                            └──────┘

FIG. 11
```

```
┌─────────┐
│  Start  │
└────┬────┘
     │                    2200
     │
┌────┴──────────────────────────────────────────┐
│ 2210                                          │
│ monitoring at least one health attribute of an individual during │
│ an artificial sensory experience              │
└────┬──────────────────────────────────────────┘
     │
┌────┴──────────────────────────────────────────┐
│ 2220                                          │
│ associating a characteristic of the artificial sensory experience │
│ with the at least one health attribute of the individual │
└────┬──────────────────────────────────────────┘
     │
┌────┴──────────────────────────────────────────┐
│ 2230                                          │
│ modifying at least one of an inhalation device-dispensed │
│ bioactive agent or the artificial sensory experience at least │
│ partially based on associating a characteristic of the artificial │
│ sensory experience with the at least one health attribute of the │
│ individual                                    │
│  ┌ ─ ─ ─ ─ ─ ─ ─ ─ ─ ─ ─ ─ ─ ─ ─ ─ ─ ─ ─ ─ ─ ┐ │
│  │ 2802                                     │ │
│  │ modifying access to at least a portion of the artificial sensory │ │
│  │ experience                               │ │
│  │ ┌ ─ ─ ─ ─ ─ ─ ─ ─ ┐  ┌ ─ ─ ─ ─ ─ ─ ─ ─ ┐ │ │
│  │ │ 2804            │  │ 2806            │ │ │
│  │ │ restricting access to at │ granting access to at least a │ │
│  │ │ least a portion of the │ portion of the artificial │ │
│  │ │ artificial sensory │  │ sensory experience │ │ │
│  │ │ experience        │  │                  │ │ │
│  │ └ ─ ─ ─ ─ ─ ─ ─ ─ ┘  └ ─ ─ ─ ─ ─ ─ ─ ─ ┘ │ │
│  └ ─ ─ ─ ─ ─ ─ ─ ─ ─ ─ ─ ─ ─ ─ ─ ─ ─ ─ ─ ─ ─ ┘ │
└────┬──────────────────────────────────────────┘
     │
┌────┴────┐
│ Finish  │
└─────────┘
```

FIG. 28

METHODS AND SYSTEMS FOR PRESENTING AN INHALATION EXPERIENCE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 30, 2008, application Ser. No. 12/317,934, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 31, 2008, application Ser. No. 12/319,143, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 12, 2009, application Ser. No. 12/378,284, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 13, 2009, application Ser. No. 12/378,485, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 20, 2009, application Ser. No. 12/380,013, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 23, 2009, application Ser. No. 12/380,108, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 27, 2009, application Ser. No. 12/380,587, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 2, 2009, application Ser. No. 12/380,679, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 25, 2009, application Ser. No. 12/383,509, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 26, 2009, application Ser. No. 12/383,819, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 31, 2009, application Ser. No. 12/384,104, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 1, 2009, application Ser. No. 12/384,203, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Apr. 20, 2009, application Ser. No. 12/386,574, which is currently co-pending, or is an application of which a currently co-pending application is entitled to the benefit of the filing date.

TECHNICAL FIELD

This description relates to methods and systems for an inhaled bioactive agent combined with an artificial sensory experience.

SUMMARY

In one aspect, a method includes but is not limited to monitoring at least one health attribute of an individual during an artificial sensory experience, associating a characteristic of the artificial sensory experience with the at least one health attribute of the individual, and modifying at least one of an inhalation device-dispensed bioactive agent or the artificial sensory experience at least partially based on associating a characteristic of the artificial sensory experience with the at least one health attribute of the individual. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for monitoring at least one health attribute of an individual during an artificial sensory experience, means for associating a characteristic of the artificial sensory experience with the at least one health attribute of the individual, and means for modifying at least one of an inhalation device-dispensed bioactive agent or the artificial sensory experience at least partially based on associating a characteristic of the artificial sensory experience with the at least one health attribute of the individual. In addition to the foregoing, other method aspects are described in the claims, drawings, and text forming a part of the present disclosure.

In one aspect, a system includes but is not limited to circuitry for monitoring at least one health attribute of an individual during an artificial sensory experience, circuitry for associating a characteristic of the artificial sensory experience with the at least one health attribute of the individual, circuitry for modifying at least one of an inhalation device-dispensed bioactive agent or the artificial sensory experience at least partially based on associating a characteristic of the artificial sensory experience with the at least one health attribute of the individual. In addition to the foregoing, other method aspects are described in the claims, drawings, and text forming a part of the present disclosure.

In one aspect, a computer program product includes but is not limited to a signal-bearing medium bearing one or more instructions for monitoring at least one health attribute of an individual during an artificial sensory experience, one or more instructions for associating a characteristic of the artificial sensory experience with the at least one health attribute of the individual, and one or more instructions for modifying at least one of an inhalation device-dispensed bioactive agent or the artificial sensory experience at least partially based on associating a characteristic of the artificial sensory experience with the at least one health attribute of the individual. In addition to the foregoing, other method aspects are described in the claims, drawings, and text forming a part of the present disclosure.

In one aspect, a system includes but is not limited to a computing device and instructions that when executed on the computing device cause the computing device to monitor at least one health attribute of an individual during an artificial sensory experience, associate a characteristic of the artificial sensory experience with the at least one health attribute of the individual, and modify at least one of an inhalation device-dispensed bioactive agent or the artificial sensory experience at least partially based on associating a characteristic of the artificial sensory experience with the at least one health attribute of the individual. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 6 illustrates an operational flow representing example operations related to combining an inhaled bioactive agent and an artificial sensory experience.

FIG. 7 illustrates an alternative embodiment of the operational flow of FIG. 6.

FIG. 8 illustrates an alternative embodiment of the operational flow of FIG. 6.

FIG. 9 illustrates an alternative embodiment of the operational flow of FIG. 6.

FIG. 10 illustrates an alternative embodiment of the operational flow of FIG. 6.

FIG. 11 illustrates an alternative embodiment of the operational flow of FIG. 6.

FIG. 28 illustrates an alternative embodiment of the operational flow of FIG. 22.

DETAILED DESCRIPTION

Figure 1:
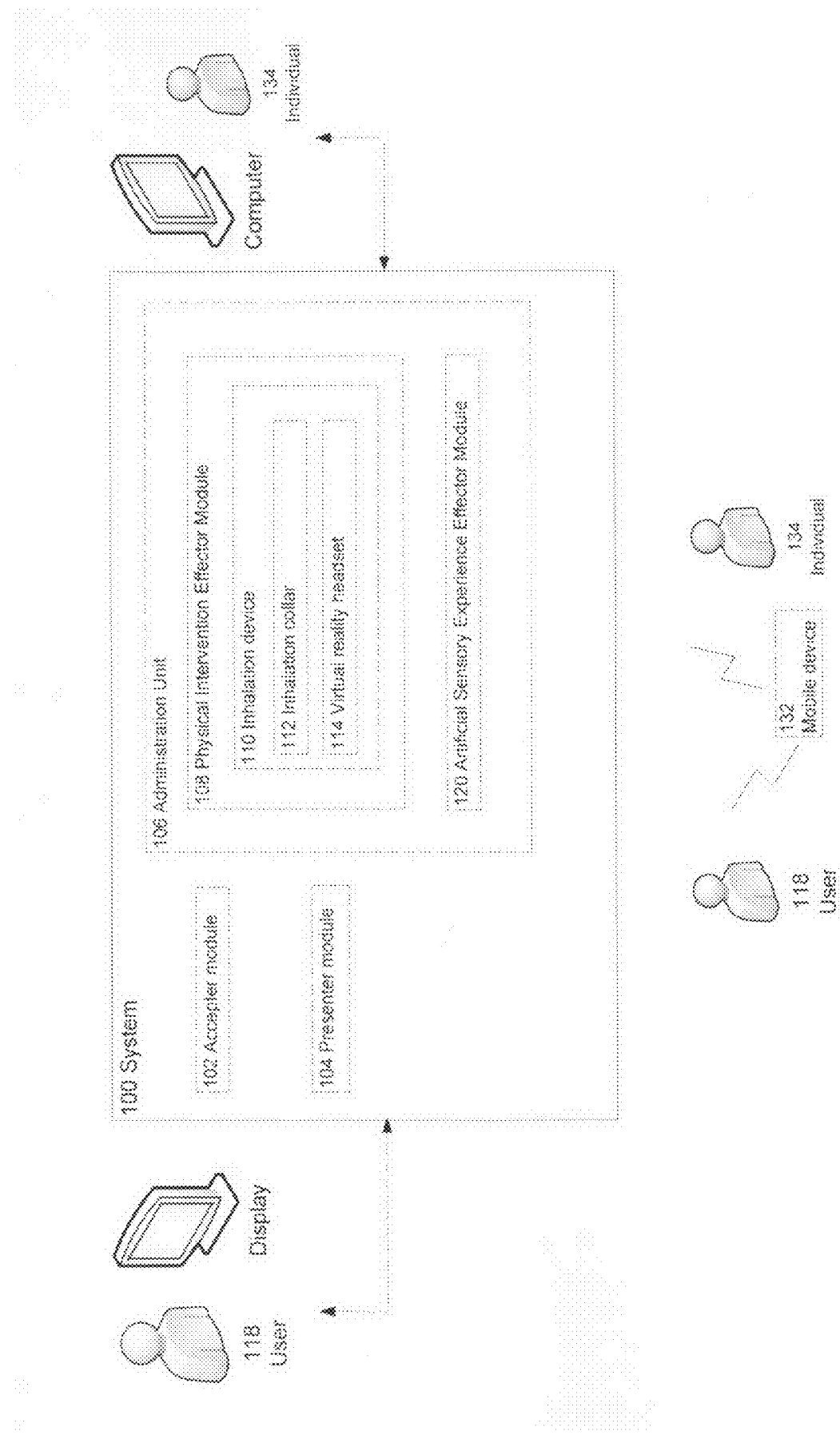
FIG. 1 illustrates an exemplary environment in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 3200 may include mobile device 132.

Figure 2:
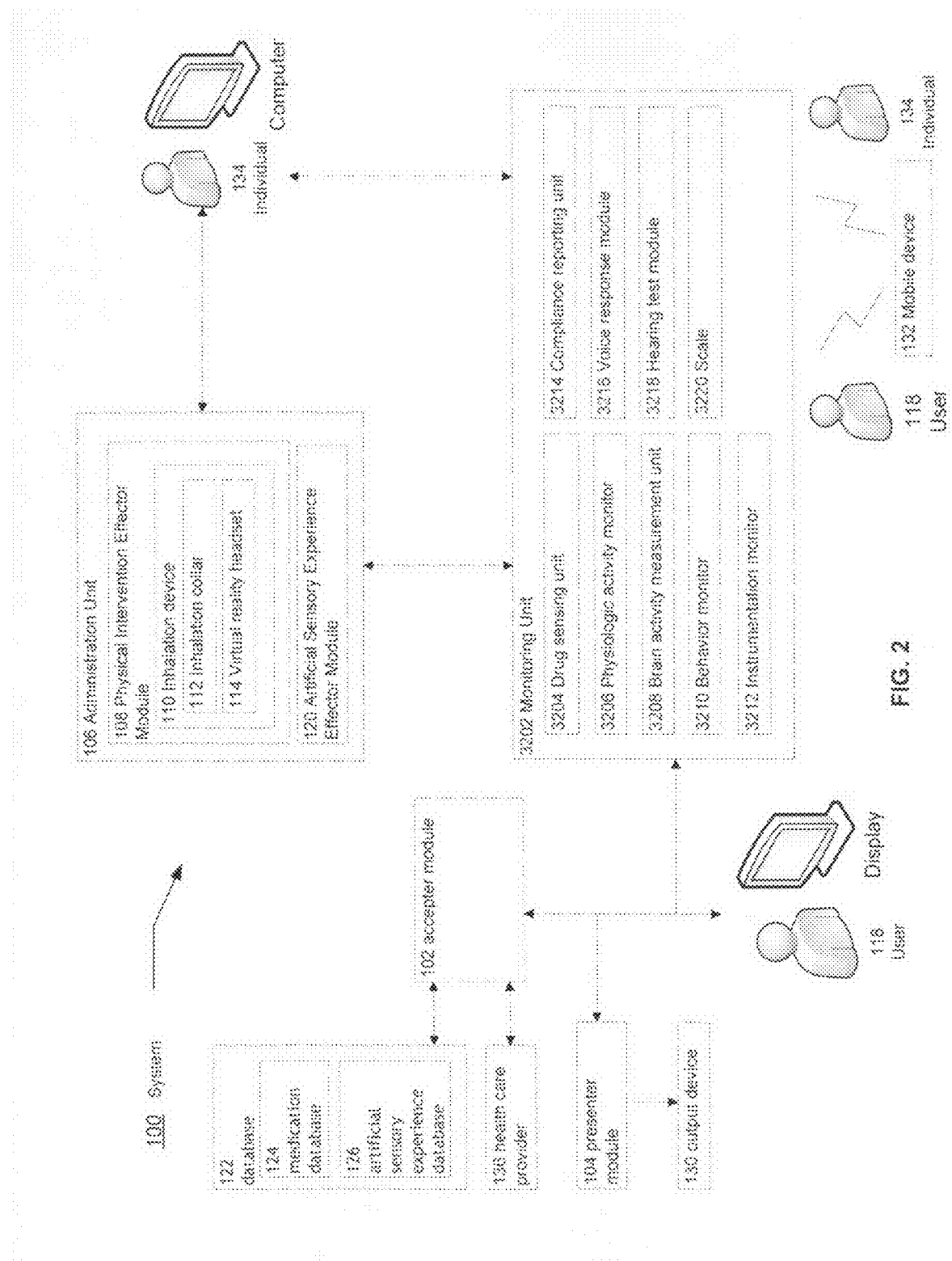
FIG. 2 illustrates an exemplary environment in which one or more technologies may be implemented.

FIG. 2 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, administration unit 106, and/or monitoring unit 3202. Accepter module 102 may receive and/or transmit information and/or data to and/or from user 118, database 122, presenter module 3410, output device 130, and/or health care provider 136. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120.

Physical intervention effector module 108 may include inhalation device 110. Inhalation device 110 may include inhalation collar 112 and/or virtual reality headset 114. Additionally, mobile device 132 may communicate with accepter module 102, presenter module 104, healthcare provider 136, user 118, individual 134, monitoring unit 3202, and/or administration unit 3222.

Figure 3:
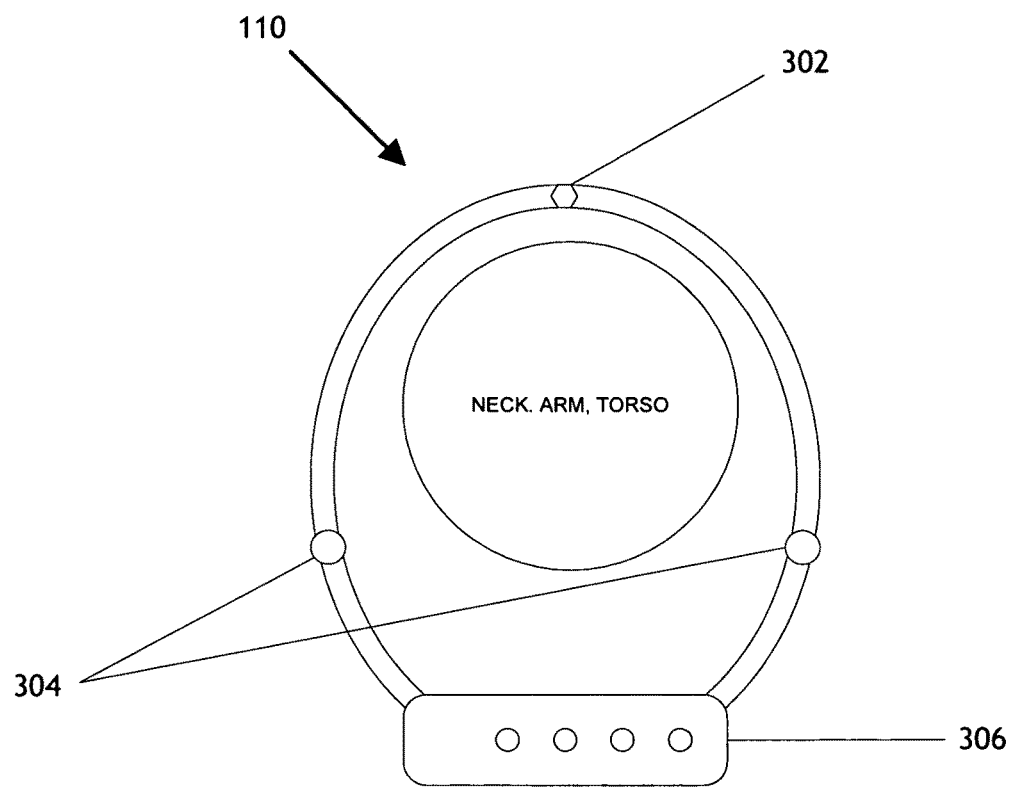
FIG. 3 illustrates an exemplary inhalation device.

FIG. 3 illustrates an exemplary inhalation device 110. An exemplary inhalation device 110 may include a closure device, a transducer, and/or a dispensing reservoir. Inhalation device 110 may include, for example, a collar, a necklace, and/or a bracelet. Inhalation device 110 may include tubing, a chain, a polymer, a metal, a textile, and may be solid and/or hollow. Closure device 302 may include a buckle, Velcro, a snap, a clasp, a lock, a coupler, elastic, and/or magnets. Transducer 304 may include a blood glucose monitor, a blood oxygen monitor, means for sending a signal to a reservoir to dispense medication, such as an antenna, means for powering the unit, such as a battery, memory, and/or a computer processor. Dispensing reservoir 306 may include means for power, such as a battery, means for receiving conditional input, such as a processor and/or memory, means for dispensing a bioactive agent in aerosol, dust and/or vapor form, such as a nebulizer, a sprayer, and/or a nozzle. Additionally, the dispensing reservoir 306 may be removable and/or refillable.

Figure 4:
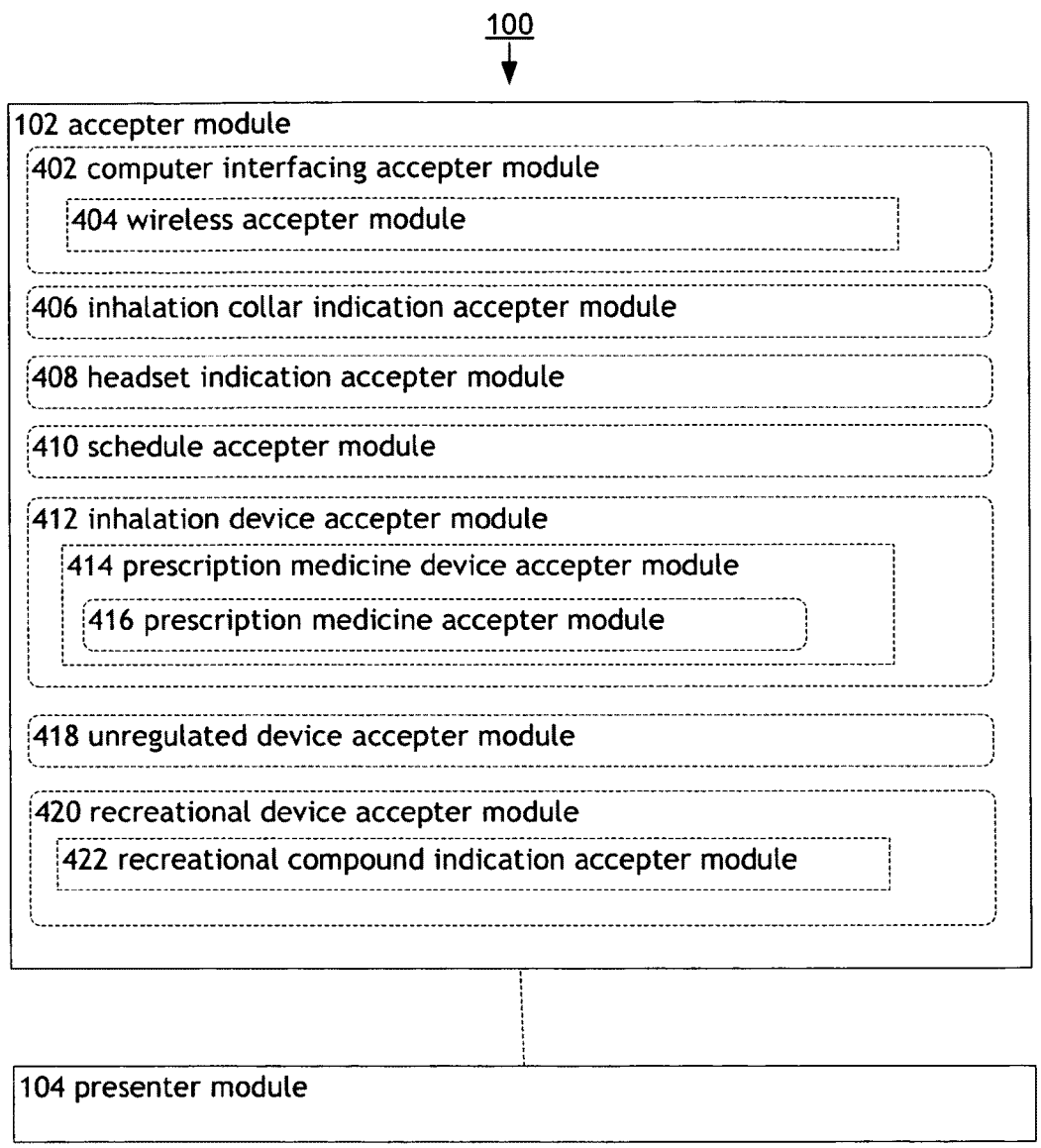
FIG. 4 illustrates an exemplary environment in which one or more technologies may be implemented.

FIG. 4 further illustrates system 100 including accepter module 102 and/or presenter module 104. Accepter module 102 may include computer interfacing accepter module 402, inhalation collar indication accepter module 406, headset indication accepter module 408, schedule accepter module 410, inhalation device accepter module 412, unregulated device accepter module 418, and/or recreational device accepter module 420. Computer interfacing accepter module 402 may include wireless accepter module 404. Inhalation device accepter module 412 may include prescription medicine device accepter module 414 and/or prescription medicine accepter module 416. Recreational device accepter module 420 may include recreational compound indication accepter module 422.

Figure 5:
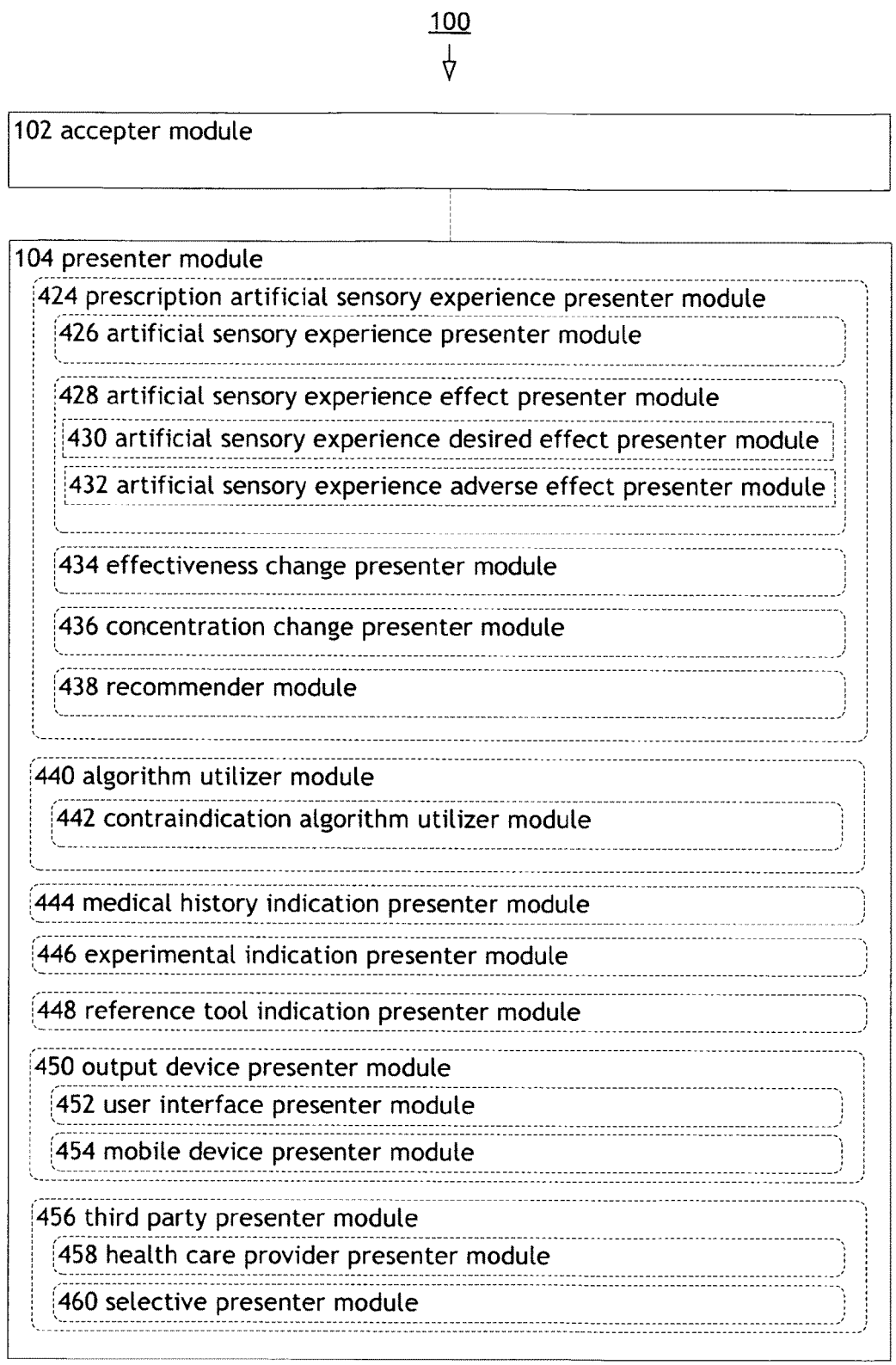
FIG. 5 illustrates an exemplary environment in which one or more technologies may be implemented.

FIG. 5 illustrates system 100 including accepter module 102 and/or presenter module 104. Presenter module 104 may include prescription artificial sensory experience presenter module 424, algorithm utilizer module 440, medical history indication presenter module 444, experimental indiciation presenter module 446, reference tool indication presenter module 448, output device presenter module 450, and/or third party presenter module 456. Prescription artificial sensory experience presenter module 424 may include artificial sensory experience presenter module 426, artificial sensory experience effect presenter module 428, effectiveness change presenter module 434, concentration change presenter module 436, and/or recommender module 438. Artificial sensory experience effect presenter module 428 may include artificial sensory experience desired effect presenter module 430 and/or artificial sensory experience adverse effect presenter module 432. Algorithm utilizer module 440 may include contraindication algorithm utilizer module 442. Output device presenter module 450 may include user interface presenter module 452 and/or mobile device presenter module 454. Third party presenter module 456 may include health care provider presenter module 458 and/or selective presenter module 460.

FIG. 6 illustrates an operational flow 600 representing example operations related to accepting an indication of at least one health-related condition and presenting an indication of at least one artificial sensory experience and an indication of at least one inhalation therapy at least partially based on the accepting at least one indication of a health-related condition. In FIG. 6 and in following figures that include various examples of operational flows, discussion and explanation may be provided with respect to the above-described examples of FIGS. 1 through 5, and/or with respect to other examples and contexts. However, it should be understood that the operational flows may be executed in a number of other environments and contexts, and/or in modified versions of FIGS. 1 through 5. Also, although the various operational flows are presented in the sequence(s) illustrated, it should be understood that the various operations may be performed in other orders than those which are illustrated, or may be performed concurrently.

After a start operation, the operational flow 600 moves to operation 610. Operation 610 depicts accepting an indication of at least one health-related condition. For example, as shown in FIGS. 1 through 5, accepter module 102 may accept an indication of a bioactive agent-dispensing inhalation device. One example of a bioactive agent-dispensing inhalation device may include an inhaler used for delivering a bioactive agent into the body using a body airway. Some other examples may include a collar, necklace, and/or a bracelet with a bioactive agent dispenser proximate to the nose, mouth, and/or inhalation route. In one embodiment, accepter module 102 may accept an indication of a bioactive agent-dispensing collar for dispensing a medication, such as a steroid and/or a bronchodilator. In some instances, accepter module 102 may include a computer processor, a user interface, and/or computer memory.

Then, operation 620 depicts presenting an indication of at least one artificial sensory experience and an indication of at least one inhalation therapy at least partially based on the accepting at least one indication of a health-related condition. For example, as shown in FIGS. 1 through 5, presenter module 104 may present an indication of a virtual world at least partially based on accepting an indication of a bioactive agent-dispensing inhalation device. One example of an artificial sensory experience may include a virtual world and/or other computer-simulated experience. Other examples of an artificial sensory experience may include experiences triggering sight, smell, hearing, touch, and/or taste. For example, presenter module 104 may present an indication of an artificial sensory experience including a virtual scent environment, which may include olfactory stimulation for improving memory. In an additional embodiment, presenter module 104 may present an indication of an artificial sensory experience including a virtual experience where the user is exposed to a virtual mountain environment coupled with a bronchodilator dose from a bioactive agent-dispensing inhalation collar. In this embodiment, the combination bronchodilator and virtual world treatment may serve to help an asthma sufferer to learn effective breathing techniques. Presenting an indication of an artificial sensory experience may include presenting the indication to a physician, to a computer monitor, to a mobile device, and/or to a third party. In some instances, presenter module 104 may include a computer processor and/or a communication device, such as a printer, a computer monitor, and/or a speaker.

FIG. 7 illustrates alternative embodiments of the example operational flow 600 of FIG. 6. FIG. 7 illustrates example embodiments where operation 610 may include at least one additional operation. Additional operations may include operation 702, operation 704, operation 706, and/or operation 708.

Operation 702 illustrates accepting an indication of a health-related physical condition. For example, as shown in FIGS. 1 through 5, computer interfacing accepter module 402 may accept an indication of a bioactive agent-dispensing inhalation device configured to interface with a computing device. In one embodiment, computer interfacing accepter module 402 may accept an indication of a bioactive agent-dispensing inhalation device configured to interface with a virtual game, such as World of Warcraft. Some examples of a computing device may include a personal computer, a virtual-reality helmet and/or headset, and/or a virtual environment. In some instances, computer interfacing accepter module 402 may include a computer processor.

Further, operation 704 illustrates accepting an indication of a bioactive agent-dispensing inhalation device configured to interface wirelessly with a computing device. For example, as shown in FIGS. 1 through 5, wireless accepter module 404 may accept an indication of a bioactive agent-dispensing inhalation device configured to interface wirelessly with a computing device. In one embodiment, wireless accepter module 404 may accept an indication of a wireless inhalation collar configured to interface wirelessly with a computer coupled to wireless video glasses. In this embodiment, both the inhalation collar and the video glasses may be wirelessly connected to the computer. The wireless bioactive agent-dispensing inhalation device may be wirelessly coupled to a computing device using, for example, an IEEE 802.11 computer network and/or a Bluetooth wireless sensor network. One example of wireless video glasses may include Qingbar GP300 video glasses available from 22moo International Pty Ldt., Cabramatta NSW, Australia. In some instances, wireless accepter module 404 may include a computer processor and/or a wireless receiving device, such as a receiving antenna.

Operation 706 illustrates accepting an indication a health-related condition from a medical history. For example, as shown in FIGS. 1 through 5, inhalation collar indication accepter module 406 may accept an indication of a bioactive agent-dispensing inhalation collar. A bioactive agent-dispensing inhalation collar may include a collar with, for example, means for dispensing a bioactive agent, such as a reservoir and/or an accompanying valve and spray nozzle. Additionally, means for dispensing a bioactive agent may include means for dispensing an aerosol, vapor, a powder (e.g. pulmicort and/or foradil), and/or a mist, such as a nebulizer, means for measuring and/or detecting a condition, such as blood oxygen level and/or body temperature, and/or means for processing information, such as a computer processor and/or computer memory. Further, a bioactive agent may be dispensed and/or dispersed in and/or include a surfactant. In one embodiment, inhalation collar indication accepter module 406 may accept an indication of a bioactive agent-dispensing collar having means for dispensing a steroid as an aerosol. Further, a bioactive agent-dispensing inhalation collar may include means for power, such as a battery and/or circuitry for receiving power from an external source, such as an AC adapter power supply. In some instances, inhalation collar indication accepter module 406 may include a computer processor.

Operation 708 illustrates accepting an indication of a bioactive agent-dispensing virtual-reality headset. For example, as shown in FIGS. 1 through 5, headset indication accepter module 408 may accept an indication of a bioactive agent-dispensing virtual-reality headset. A virtual-reality headset may include a microphone, headphones or speakers for hearing, and/or a display. A virtual-reality headset may be configured for enabling a user to engage in an artificial sensory experience including sound, smell, and/or sight. One example of a virtual-reality headset may include a virtual reality helmet configured to give the user a 360° view of a mountain landscape while dispensing a bronchodilator for helping the user learn improved breathing techniques. Another example of a virtual reality head set may include an Olympus Eye-Trek FMD-200-TFT active matrix head mounted display with Speaker, available from Olympus America Inc., Center Valley Pa. In some instances, headset indication accepter module 408 may include a computer processor.

FIG. 8 illustrates alternative embodiments of the example operational flow 600 of FIG. 6. FIG. 8 illustrates example embodiments where the operation 610 may include at least one additional operation. Additional operations may include an operation 802, an operation 804, an operation 806, and/or an operation 808.

Operation 802 illustrates accepting an indication of a health-related mental condition. For example, as shown in FIGS. 1 through 5, schedule accepter module 410 may accept at least one of a bioactive agent dosing schedule or a bioactive agent administration schedule. Accepting a bioactive agent dosing schedule or a bioactive agent administration schedule may include accepting from a computer processor, accepting from a memory device, and/or accepting from a user input. In one embodiment, schedule accepter module 410 may accept a dosing schedule specifying a bronchoditator administration dosage for a specified time period, such one dose from an inhalation device once every thirty minutes. In another embodiment, schedule accepter module 410 may accept a bioactive agent administration schedule specifying at least one time a bronchodilator may be administered. In some instances, schedule accepter module 410 may include a computer processor.

Operation 804 illustrates accepting an indication of a medicine-dispensing inhalation device. For example, as shown in FIGS. 1 through 5, inhalation device accepter module 412 may accept an indication of a medicine-dispensing inhalation device. A medicine-dispensing inhalation device may include a device for dispensing a substance for treating a disease and/or illness. For example, a medicine-dispensing inhalation device may include an inhaler as described in Robertson et al., U.S. Pat. No. 7,383,837, which is incorporated herein by reference. Some other examples may include a metered-dose inhaler, a dry powder inhaler, and/or a nebulizer. In one embodiment, inhalation device accepter module 412 may accept an indication of a medicine-dispensing metered-dose inhaler configured to dispense albuterol. In some instances, inhalation device accepter module 412 may include a computer processor.

Further, operation 806 illustrates accepting an indication of a health-related condition from a user input. For example, as shown in FIGS. 1 through 5, prescription medicine device accepter module 414 may accept an indication of a prescription medicine-dispensing inhalation device. A prescription medicine-dispensing inhalation device may include a device configured to dispense a medication only available from a licensed health care provider. Some examples of a prescription medication available from a licensed health care provider may include albuterol, coricosteroids, nitrous oxide, a benzodiazepine, Theophylline, nedocromil sodium, and/or fluticasone/salmeterol. In one embodiment, prescription medicine device accepter module 414 may accept an indication of a prescription medicine-dispensing inhalation device configured for dispensing ciclesonide. In some instances, prescription medicine device accepter module 414 may include a computer processor.

Further, operation 808 illustrates indication of at least one of a prescribed artificial sensory experience or a prescribed inhalation therapy. For example, as shown in FIGS. 1 through 5, prescription medicine accepter module 416 may accept an indication of at least one of a steroid, a bronchodilator, menthol, nitrous oxide, a benzodiazepine, or halothane. One example of a steroid may include an anabolic steroid, which may be a derivative of androgens (such as testosterone), for stimulating growth. Another example of a steroid may include a corticosteroid, which may be often used as an anti-inflammatory prescribed for asthma. A bronchodilator may include a substance that dilates the bronchi and bronchioles decreasing airway resistance and thereby facilitating airflow. Menthol may include an organic and/or synthetic compound with local anesthetic and counterirritant qualities often used for relieving throat irritation and/or as a decongestant. Nitrous oxide may include a gas often used as a weak general anesthetic. A benzodiazepine may include a class of psychoactive drugs with varying hypnotic, sedative, anxiolytic, anticonvulsant, muscle relaxant and amnesic properties, which may be mediated by slowing down the central nervous system. In one embodiment, prescription medicine accepter module 416 may accept an indication of a benzodiazepine. One example of benzodiazepine delivery through an inhalation route may be disclosed in Kim et al., U.S. Patent Publication No. 2003/0032638, which is incorporated herein by reference. An anti-allergic agent may include an agent configured to block the action of allergic mediators and/or to prevent activation of cells and degranulation processes. Some examples of an anti-allergic agent may include an antihistamine and/or cromones like mast cell stabilizers, such as cromoglicic acid and nedocromil sodium. A muscle relaxant may include a bioactive agent for affecting skeletal muscle function and/or decreasing muscle tone. One example of a skeletal muscle relaxant may include carisoprodol. Additionally, a muscle relaxant may include a smooth muscle relaxant. One example of a smooth muscle relaxant may include a methylxanthine, such as Theophylline. An anesthetic may include an inhalational general anesthetic, such as halothane, desflurane, enflurane, isoflurane, and/or sevoflurane. In some instances, prescription medicine accepter module 416 may include a computer processor.

FIG. 9 illustrates alternative embodiments of the example operational flow 600 of FIG. 6. FIG. 9 illustrates example embodiments where the operation 610 may include at least one additional operation. Additional operations may include an operation 902, an operation 904, and/or an operation 906.

Operation 902 illustrates accepting an indication of an unregulated bioactive agent-dispensing inhalation device. For example, as shown in FIGS. 1 through 5, unregulated device accepter module 418 may accept an indication of an unregulated bioactive agent-dispensing inhalation device. In one embodiment, unregulated device accepter module 418 may accept an indication of an oxygen-dispensing inhalation device. Some examples of an unregulated bioactive agent may include oxygen, aromas used for aromatherapy, and/or menthol. In another embodiment, unregulated device accepter module 418 may accept an indication of an aromatherapeutic-dispensing inhalation collar. In some instances, unregulated device accepter module 418 may include a computer processor.

Operation 904 illustrates accepting an indication of a recreational bioactive agent-dispensing inhalation device. For example, as shown in FIGS. 1 through 5, recreational device accepter module 420 may accept an indication of a recreational bioactive agent-dispensing inhalation device. In one embodiment, recreational device accepter module 420 may accept an indication of a recreational bioactive agent-dispensing inhalation device. Some examples of a recreational bioactive agent may include an aroma compound used for aromatherapy and/or artificial smoke. Other examples of a recreational bioactive agent may include incense and/or smoke, such as incense and/or smoke used in a religious rite. In some instances, recreational device accepter module 420 may include a computer processor.

Further, operation 906 illustrates accepting an indication of at least one artificial smoke or an aroma compound. For example, as shown in FIGS. 1 through 5, recreational compound indication accepter module 422 may accept an indication of at least one artificial smoke or an aroma compound. In one embodiment, recreational compound indication accepter module 422 may accept an indication of artificial smoke while experiencing a virtual world. In another embodiment, recreational compound indication accepter module 422 may accept an indication of lemon oil while experiencing an artificial sensory experience. In this embodiment, the use of lemon oil as an aromatherapeutic may serve to enhance a user's mood and/or provide relaxation. In some instances, recreational compound indication accepter module 422 may include a computer processor.

FIG. 10 illustrates alternative embodiments of the example operational flow 600 of FIG. 6. FIG. 10 illustrates example embodiments where operation 620 may include at least one additional operation. Additional operations may include operation 1002, operation 1004, operation 1006, operation 1008, and/or operation 1010.

Operation 1002 illustrates indication of at least one of a prescribed artificial sensory experience or a prescribed inhalation therapy. For example, as shown in FIGS. 1 through 5, prescription artificial sensory experience presenter module 424 may present an indication of a prescribed artificial sensory experience. A prescribed artificial sensory experience may include any artificial sensory experience prescribed by a health care professional, such as a physician, a mental health specialist, a nurse, a physical therapist, an occupational therapist, a chiropractor, and/or a homeopathic practitioner. In one embodiment, prescription artificial sensory experience presenter module 424 may present an indication of a virtual world prescribed by a psychiatrist. In this embodiment, the prescribed virtual world may be configured to be administered in conjunction with a prescribed bioactive agent. Administering a prescribed bioactive agent in conjunction with a prescribed artificial sensory experience may serve to increase efficacy of the combined therapy, for example, by serving as a distraction from pain. In some instances, prescription artificial sensory experience presenter module 424 may include a computer processor and/or a display device, such as a computer monitor and/or a printer.

Further, operation 1004 illustrates an indication of at least one of a virtual world experience, a massively multiplayer online game, or a learning tutorial. For example, as shown in FIGS. 1 through 5, artificial sensory experience presenter module 426 may present an indication of a virtual world experience, a massively multiplayer online game, or a Learning tutorial. A virtual world experience may include a computer-based simulated environment intended to be interactive. Some examples of a virtual world experience may include a text-based chat room, computer conferencing, an online game, a single player game, and/or a computer tutorial. A massively multiplayer online game may include a video game capable of supporting multiple players, such as World of Warcraft and/or SecondLife. Additionally, a massively multiplayer online game may include an experience, such as a game, which may include a video game or other interactive experience involving numbers of individuals, for example, a religious ceremony or combat training exercise. An online learning tutorial may include a screen recording, a written document (either online or downloadabte), or an audio file, where a user may be given step by step instructions on how to do something. In one embodiment, artificial sensory experience presenter module 426 may present an indication of a virtual world experience, such as World of Warcraft. In some instances, artificial sensory experience presenter module 426 may include a computer processor.

Further, operation 1006 illustrates indication of at least one effect of the indication of at least one of a prescribed artificial sensory experience. For example, as shown in FIGS. 1 through 5, artificial sensory experience effect presenter module 428 may present an indication of at least one effect of the prescribed artificial sensory experience. In one embodiment, artificial sensory experience effect presenter module 428 may present an indication of at Least one effect of the prescribed artificial sensory experience. An effect may include a reaction and/or thing that occurs as a result of the artificial sensory experience. For example, an effect may include a side effect, a desired effect, and/or an adverse effect. Some examples of an effect may include an increased bioactive agent efficacy, dizziness, and/or a decreased heart rate. In some instances, artificial sensory experience effect presenter module 428 may include a computer processor.

Further, operation 1008 illustrates presenting an indication of at least one expected desired effect of the prescribed artificial sensory experience. For example, as shown in FIGS. 1 through 5, artificial sensory experience desired effect presenter module 430 may present an indication of at least one desired effect of the prescribed artificial sensory experience. Some examples of a desired effect may include effects such as an increased bioactive agent efficacy, a cured illness and/or condition, and/or a changed behavior. In one embodiment, artificial sensory experience desired effect presenter module 430 may present an indication of an increased opioid efficacy measured by self pain evaluation by an individual. In some instances, artificial sensory experience desired effect presenter module 430 may include a computer processor and/or a display, such as a monitor and/or a printer.

Further, operation 1010 illustrates an indication of at least one prescribed inhalation therapy. For example, as shown in FIGS. 1 through 5, artificial sensory experience adverse effect presenter module 432 may present an indication of an expected adverse effect of the prescribed artificial sensory experience. An adverse effect may include a harmful and/or undesired effect resulting from an intervention, such as an artificial sensory experience. Some examples of an adverse effect may include headache, dizziness, depression, bleeding, seizure, and/or fever. In one embodiment, artificial sensory experience adverse effect presenter module 432 may present an indication of fever in an individual while being administered a prescribed artificial sensory experience and bioactive agent. In some instances, artificial sensory experience adverse effect presenter module 432 may include a computer processor, a display device, such as a monitor and/or printer, and/or medical instrumentation, such as a thermometer configured for measuring a body temperature.

FIG. 11 illustrates alternative embodiments of the example operational flow 600 of FIG. 6. FIG. 11 illustrates example embodiments where operation 620 may include at least one additional operation. Additional operations may include operation 1102, operation 1104, and/or operation 1106.

Operation 1102 illustrates an indication of at least one prescribed bioactive agent. For example, as shown in FIGS. 1 through 5, effectiveness change presenter module 434 may present an indication of at least one time period of an expected change in bioactive agent effectiveness. In one embodiment, effectiveness change presenter module 434 may present an indication of a time period when an opioid is expected to decrease in effectiveness. Such an indication of decrease and/or change in bioactive agent effectiveness may serve to indicate an appropriate time period for administering and/or modifying an artificial sensory experience to compensate for a change in bioactive agent efficacy. In another embodiment, effectiveness change presenter module 434 may present an indication of a time period where a blood stream morphine concentration drops. This time period of low blood stream morphine concentration may be appropriate for presenting an immersive virtual world for serving as a distraction to any increase in pain caused by lowered morphine concentration. In some instances, effectiveness change presenter module 434 may include a computer processor.

Further, operation 1104 illustrates an indication of at least one time period of an expected change in bioactive agent blood concentration. For example, as shown in FIGS. 1 through 5, concentration change presenter module 436 may present an indication of at least one time period of an expected change in bioactive agent blood concentration. In one embodiment, concentration change presenter module 436 may present an indication of a one hour time period of an expected change in hydrocodone blood concentration. Indicating a time period of a change in blood concentration may serve to help determine an artificial sensory experience administration schedule. For example, if a bioactive agent blood concentration is expected to be reduced during a certain time period, an artificial sensory experience configured for distracting an individual from pain may be selected for administration during that time period. In some instances, concentration change presenter module 436 may include a computer processor and/or a display device, such as a printer and/or a computer monitor.

Further, operation 1106 illustrates recommending at least one of an artificial sensory experience administration schedule. For example, as shown in FIGS. 1 through 5, recommender module 438 may recommend an artificial sensory experience administration schedule. In one embodiment, recommender module 438 may recommend a time schedule for administration of a virtual world experience. A time schedule may be recommended by taking into account factors involving the individual and/or the bioactive agent. For example, efficacy of the bioactive agent versus time may be a factor, such as a time period when the bioactive agent is less effective. Efficacy of the bioactive agent may be a factor in determining when an artificial sensory experience is administered because of the potential for the artificial sensory experience to compensate for a changed bioactive agent efficacy. An additional factor may include an attribute of the individual, such as how a bioactive agent and/or specific artificial sensory experience affects the individual, for example a side effect. Another example of recommending an artificial sensory experience may be found in Akazawa et al., U.S. Pat. No. 7,155,680, which is incorporated herein by reference. In some instances, recommender module 438 may include a computer processor.

Figure 12:
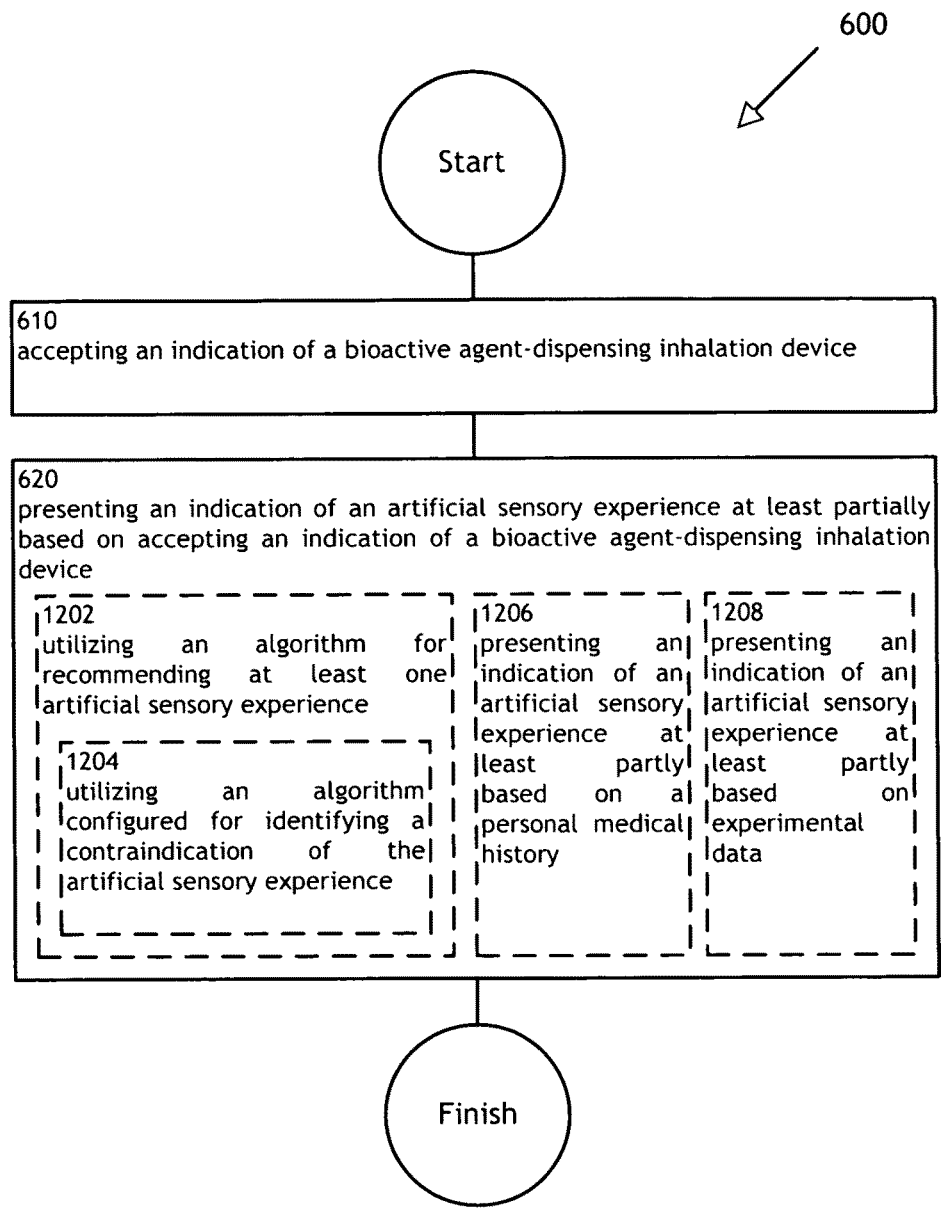
FIG. 12 illustrates an alternative embodiment of the operational flow of FIG. 6.

FIG. 12 illustrates alternative embodiments of the example operational flow 600 of FIG. 6. FIG. 12 illustrates example embodiments where operation 620 may include at least one additional operation. Additional operations may include operation 1202, operation 1204, operation 1206, and/or operation 1208.

Operation 1202 illustrates an indication of an unregulated inhalation. For example, as shown in FIGS. 1 through 5, algorithm utilizer module 440 may utilize an algorithm for recommending at least one artificial sensory experience. An algorithm for recommending an artificial sensory experience may include any computation, formula, statistical survey, and/or look-up table for determining and/or selecting a suitable artificial sensory experience. Some examples may include a computer software algorithm, a calculator, a flowchart, and/or a decision tree. In one embodiment, algorithm utilizer module 440 may utilize an algorithm that uses an inputted indication of an analgesic, such as oxycodone, and determines a suitable artificial sensory experience by analyzing periods of low blood concentration of the oxycodone. In this embodiment, algorithm utilizer module 440 may recommend an artificial sensory experience that may be effective in pain distraction when bioactive agent blood concentration may be reduced but before an additional dose may be available. In some instances, algorithm utilizer module 440 may include a computer processor.

Further, operation 1204 illustrates an indication of an unregulated inhalation. For example, as shown in FIGS. 1 through 5, contraindication algorithm utilizer module 442 may utilize an algorithm configured for identifying a contraindication of the artificial sensory experience. A contraindication of an artificial sensory experience may include giving an indication against the advisability of the artificial sensory experience. For example, contraindication algorithm utilizer module 442 may utilize an algorithm that considers an individual's personal medical history, such as a phobia, and may recommend not prescribing a certain artificial sensory experience, which may include an object that may trigger the phobia. Contraindication algorithm utilizer module 442 may identify a contraindication of an artificial sensory experience for reasons such as an adverse effect and/or inefficacy. In some instances, contraindication algorithm utilizer module 442 may include a computer processor.

Operation 1206 illustrates presenting an indication of an artificial sensory experience at least partly based on a personal medical history. For example, as shown in FIGS. 1 through 5, medical history indication presenter module 444 may present an indication of an artificial sensory experience at least partly based on a personal medical history. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In one embodiment, medical history indication presenter module 444 may present an indication of a suitable virtual world based on a personal medical history. In this embodiment, the personal medical history may indicate that an individual may be averse to a certain virtual world, such as a virtual world with rapid animation that may cause nausea. In some instances, medical history indication presenter module 444 may include a computer processor and/or a display device, such as a computer monitor and/or a printer.

Operation 1208 illustrates utilizing an algorithm configured for recommending at least one of an artificial sensory experience. For example, as shown in FIGS. 1 through 5, experimental data indication presenter module 446 may present an indication of an artificial sensory experience at least partly based on experimental data. Experimental data may include any data from an experiment, such as a clinical trial. The experiment may be an experiment including an individual and/or a group of people. In one embodiment, experimental data indication presenter module 446 may present an indication of a virtual world suitable for an individual based on a clinical trial involving a group of 1,000 people showing a certain success rate for reducing a phobia, such as fear of heights. In some instances, experimental data indication presenter module 446 may include a computer processor and/or a display device, such as a computer monitor, a mobile phone, and/or a printer.

Figure 13:
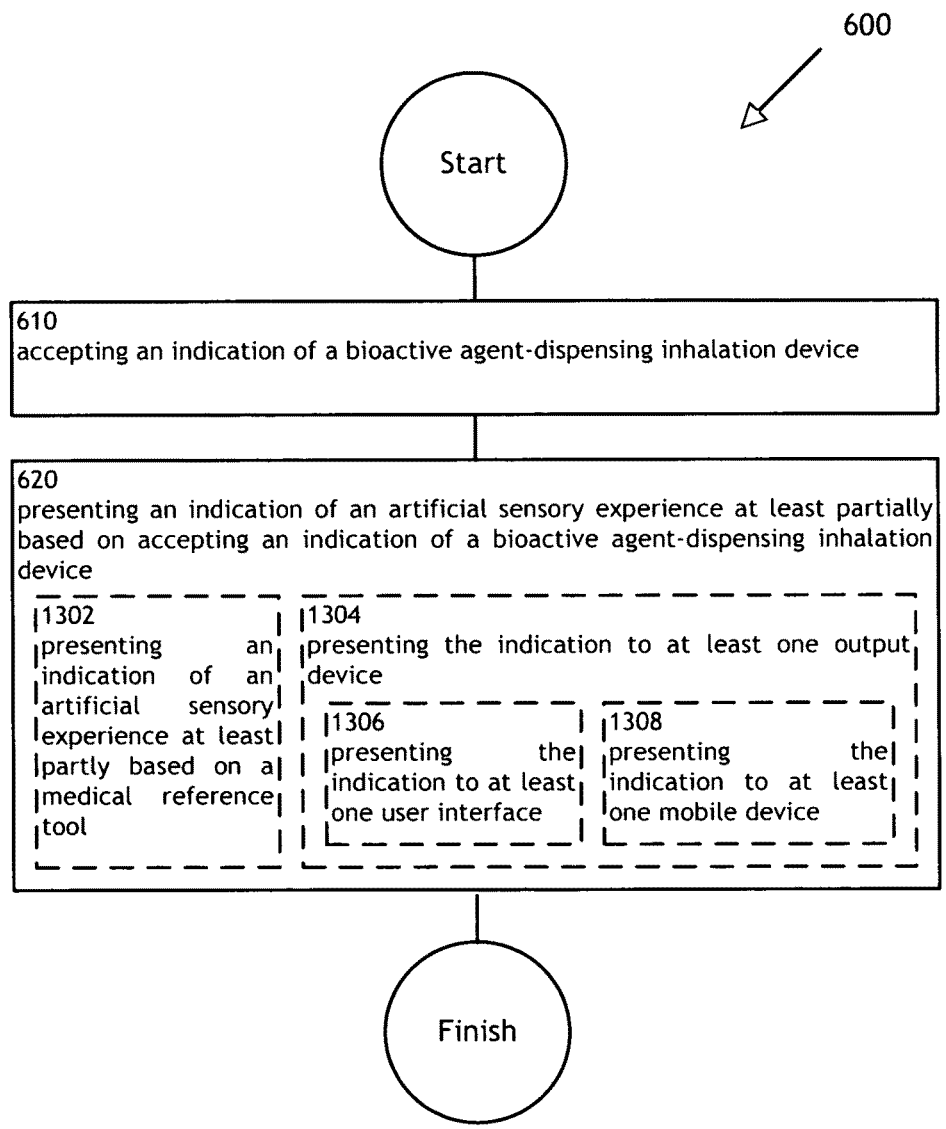
FIG. 13 illustrates an alternative embodiment of the operational flow of FIG. 6.

FIG. 13 illustrates alternative embodiments of the example operational flow 600 of FIG. 6. FIG. 13 illustrates example embodiments where the operation 620 may include at least one additional operation. Additional operations may include an operation 1302, an operation 1304, an operation 1306, and/or an operation 1308.

Operation 1302 illustrates presenting at least one of an indication of an artificial sensory experience or an indication of inhalation therapy at least partly based on a medical reference tool. For example, as shown in FIGS. 1 through 5, reference tool indication presenter module 448 may present an indication of an artificial sensory experience at least partly based on a medical reference tool. A medical reference tool may include a reference book, a reference database, and/or reference software. Some examples of a medical reference book may include a medical dictionary, a medical journal, and/or a book of drug interactions. One example of a reference database may include the National Cancer Center Cancer Image Reference (NCC-CIR) database and/or DynaMed. Some examples of reference software may include Skyscape software for a mobile phone and/or MedAlert. In one embodiment, reference tool indication presenter module 448 may present an indication of an artificial sensory experience based on a reference database, such as a database including data from a clinical trial. In some instances, reference tool indication presenter module 448 may include a computer processor and/or a display device, such as a mobile phone, a printer, and/or a computer monitor.

Operation 1304 illustrates presenting the indication to at least one output device. For example, as shown in FIGS. 1 through 5, output device presenter module 450 may present to at least one output device. In one example, output device presenter module 450 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134. In some instances, output device presenter module 450 may include a computer processor.

Further, operation 1306 illustrates presenting the indication to at least one user interface. For example, as shown in FIGS. 1 through 5, user interface presenter module 452 may present to at least one user interface. In one embodiment, user interface presenter module 452 may present to a touchscreen device. A user interface may include means by which an individual may interact with a system. Some examples of a user interface may include a touchscreen, a graphical user interface, a tactile interface, and/or a live user interface. In some instances, user interface presenter module 452 may include a computer processor.

Further, operation 1308 illustrates presenting the indication to at least one mobile device. For example, as shown in FIGS. 1 through 5, mobile device presenter module 454 may present to at least one mobile device. In one embodiment, mobile device presenter module 454 may present to a mobile phone. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, mobile device presenter module 454 may include a computer processor.

Figure 14:
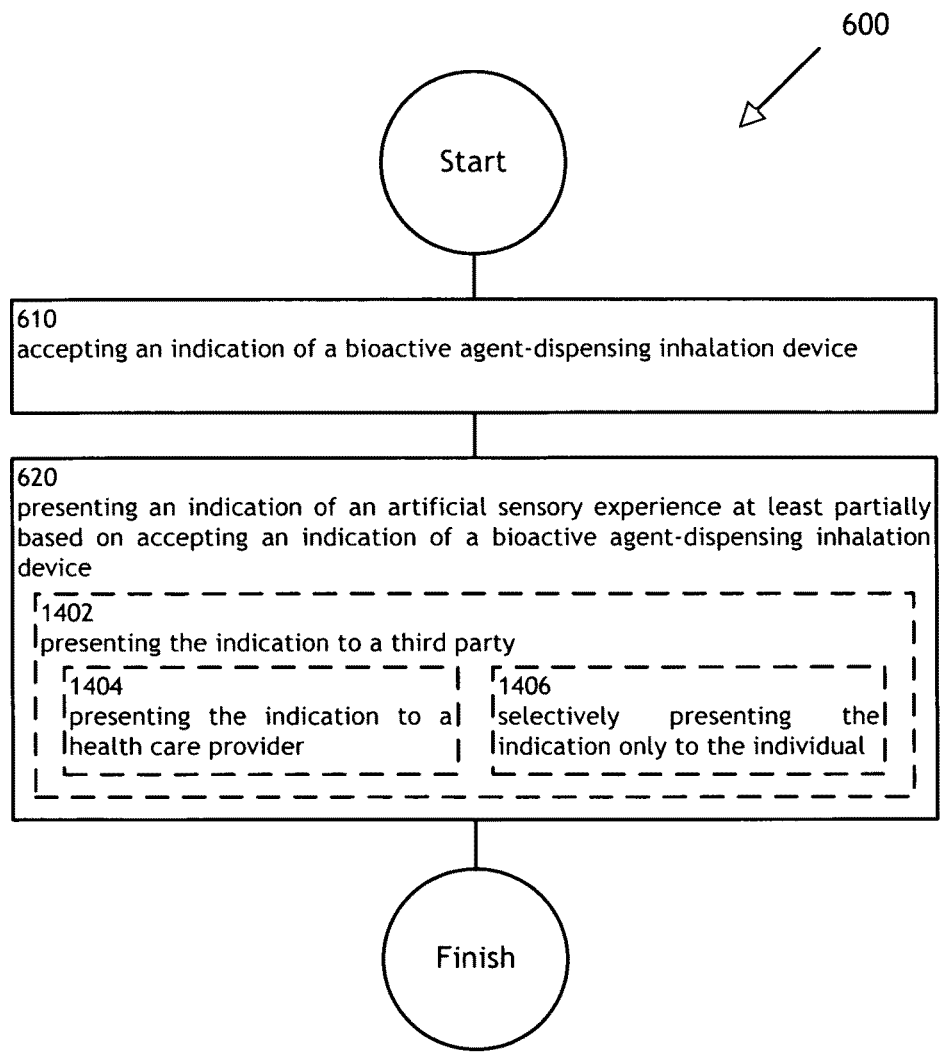
FIG. 14 illustrates an alternative embodiment of the operational flow of FIG. 6.

FIG. 14 illustrates alternative embodiments of the example operational flow 600 of FIG. 6. FIG. 14 illustrates example embodiments where operation 620 may include at least one additional operation. Additional operations may include operation 1402, operation 1404, and/or operation 1406.

Operation 1402 illustrates presenting the indication to at least one third party. For example, as shown in FIGS. 1 through 5, third party presenter module 456 may present to an individual's physician. A third party may include a party that is an independent party, person, and/or entity. Some examples of a third party may include a physician, a medical database, a hospital, a law enforcement agency, and/or a pharmacy. In one embodiment, third party presenter module 456 may present an indication to an insurance company. Another example of reporting to a third party may include creating displays and reports for aggregating data from therapy results, further discussed in Bair et al., U.S. Pat. No. 6,067,523, which is incorporated herein by reference. In some instances, third party presenter module 456 may include a computer processor and/or a communications device, such as a monitor and network link.

Further, operation 1404 illustrates presenting the indication to at least one health care provider. For example, as shown in FIGS. 1 through 5, health care provider presenter module 458 may present to a health care provider. A health care provider may include a pharmacy, a pharmaceutical company, a medical device company, a research institution, a computer software and/or computer hardware company, a website, a nurse and/or a physician. In one embodiment, health care provider presenter module 458 may present to a physician a prescribed combination artificial sensory experience and bioactive agent therapy via a secured website. In some instances, health care provider presenter module 458 may include a computer processor.

Further, operation 1406 illustrates selectively presenting the indication only to the individual. For example, as shown in FIGS. 1 through 5, selective presenter module 460 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 460 may present only to individual 134 and may keep results of a certain combination therapy confidential. In one embodiment, an encryption key may be employed to protect selected information. In an additional example, selective presenter module 460 may report only to a law enforcement agency and/or representative, such as a probation officer, and not to individual 134. In some instances, selective presenter module 460 may include a computer processor.

Figure 15:
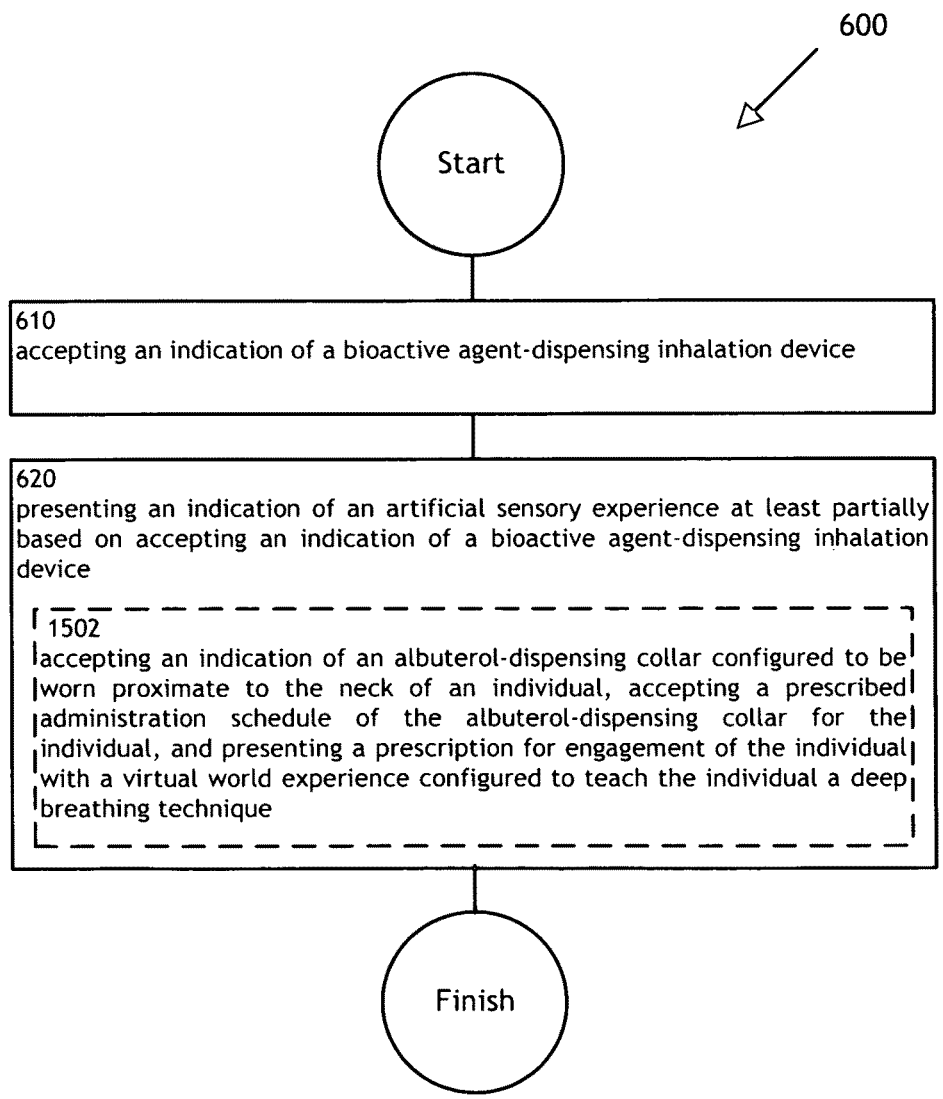
FIG. 15 illustrates an alternative embodiment of the operational flow of FIG. 6.

FIG. 15 illustrates alternative embodiments of the example operational flow 600 of FIG. 6. FIG. 15 illustrates example embodiments where the operation 620 may include at least one additional operation. Additional operations may include an operation 1502.

Operation 1502 illustrates accepting an indication of an individual's asthma, presenting a prescribed administration schedule of an albuterol-dispensing collar therapy for the individual, and presenting a prescription for engagement of the individual with a virtual world experience configured to teach the individual a deep breathing technique. For example, as shown in FIGS. 1 through 5, accepter module 102 and/or presenter module 104 may accept an indication of an albuterol-dispensing collar configured to be worn proximate to the neck of an individual, accept a prescribed administration schedule of the albuterot-dispensing collar for the individual, and present a prescription for engagement of the individual with a virtual world experience configured to teach the individual a deep breathing technique. In some instances, accepter module 102 and/or presenter module 104 may include a computer processor.

Figure 16:
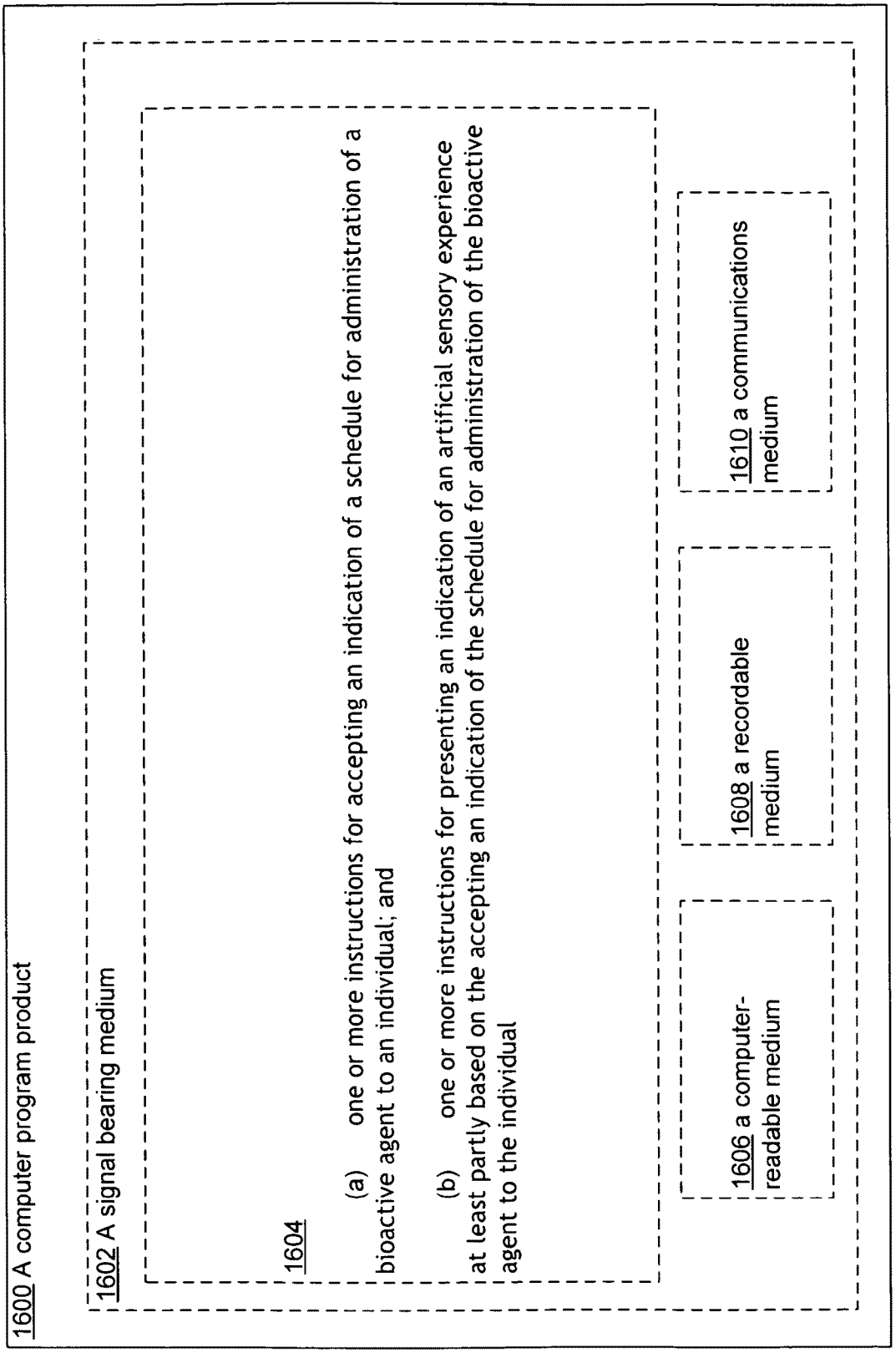
FIG. 16 illustrates a computer program product related to combining an inhaled bioactive agent and an artificial sensory experience.

FIG. 16 illustrates a partial view of an example computer program product 1600 that includes a computer program 1604 for executing a computer process on a computing device. An embodiment of the example computer program product 1600 is provided using a signal-bearing medium bearing 1602, and may include one or more instructions for accepting an indication of at least one health-retated condition and one or more instructions for presenting an indication of at least one artificial sensory experience and an indication of at least one inhalation therapy at least partially based on the accepting at least one indication of a health-related condition. The one or more instructions may be, for example, computer executable and/or logic-implemented instructions. In one implementation, the signal-bearing medium 1602 may include a computer-readable medium 1606. In one implementation, the signal bearing medium 1602 may include a recordable medium 1608. In one implementation, the signal bearing medium 1602 may include a communications medium 1610.

Figure 17:
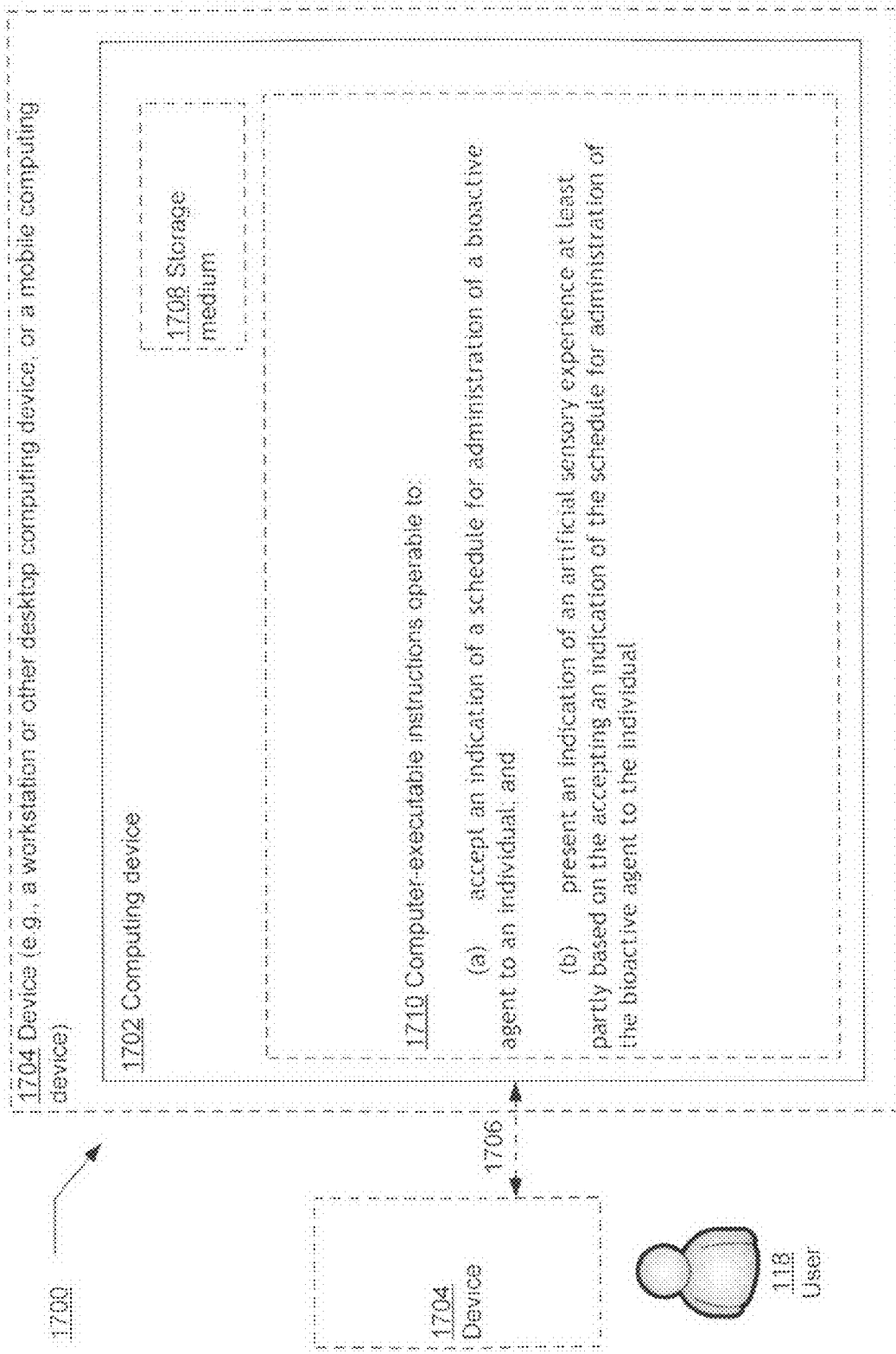
FIG. 17 illustrates a system related to combining an inhaled bioactive agent and an artificial sensory experience.

FIG. 17 illustrates an example system 1700 in which embodiments may be implemented. The system 1700 includes a computing system environment. The system 1700 also illustrates the user 118 using a device 1704, which is optionally shown as being in communication with a computing device 1702 by way of an optional coupling 1706. The optional coupling 1706 may represent a local, wide-area, or peer-to-peer network, or may represent a bus that is internal to a computing device (e.g., in example embodiments in which the computing device 1702 is contained in whole or in part within the device 1704). A storage medium 1708 may be any computer storage media.

The computing device 1702 includes computer-executable instructions 1710 that when executed on the computing device 1702 cause the computing device 1702 to accept an indication of a schedule for administration of a bioactive agent to an individual and present an indication of an artificial sensory experience at least partly based on the accepting an indication of the schedule for administration of the bioactive agent to the individual. As referenced above and as shown in FIG. 17, in some examples, the computing device 1702 may optionally be contained in whole or in part within the device 1704.

In FIG. 17, then, the system 1700 includes at least one computing device (e.g., 1702 and/or 1704). The computer-executable instructions 1710 may be executed on one or more of the at least one computing device. For example, the computing device 1702 may implement the computer-executable instructions 1710 and output a result to (and/or receive data from) the computing device 1704. Since the computing device 1702 may be wholly or partially contained within the computing device 1704, the device 1704 also may be said to execute some or all of the computer-executable instructions 1710, in order to be caused to perform or implement, for example, various ones of the techniques described herein, or other techniques.

The device 1704 may include, for example, a portable computing device, workstation, or desktop computing device. In another example embodiment, the computing device 1702 is operable to communicate with the device 1704 associated with the user 118 to receive information about the input from the user 118 for performing data access and data processing and presenting an output of the user-health test function at least partly based on the user data.

Figure 18:
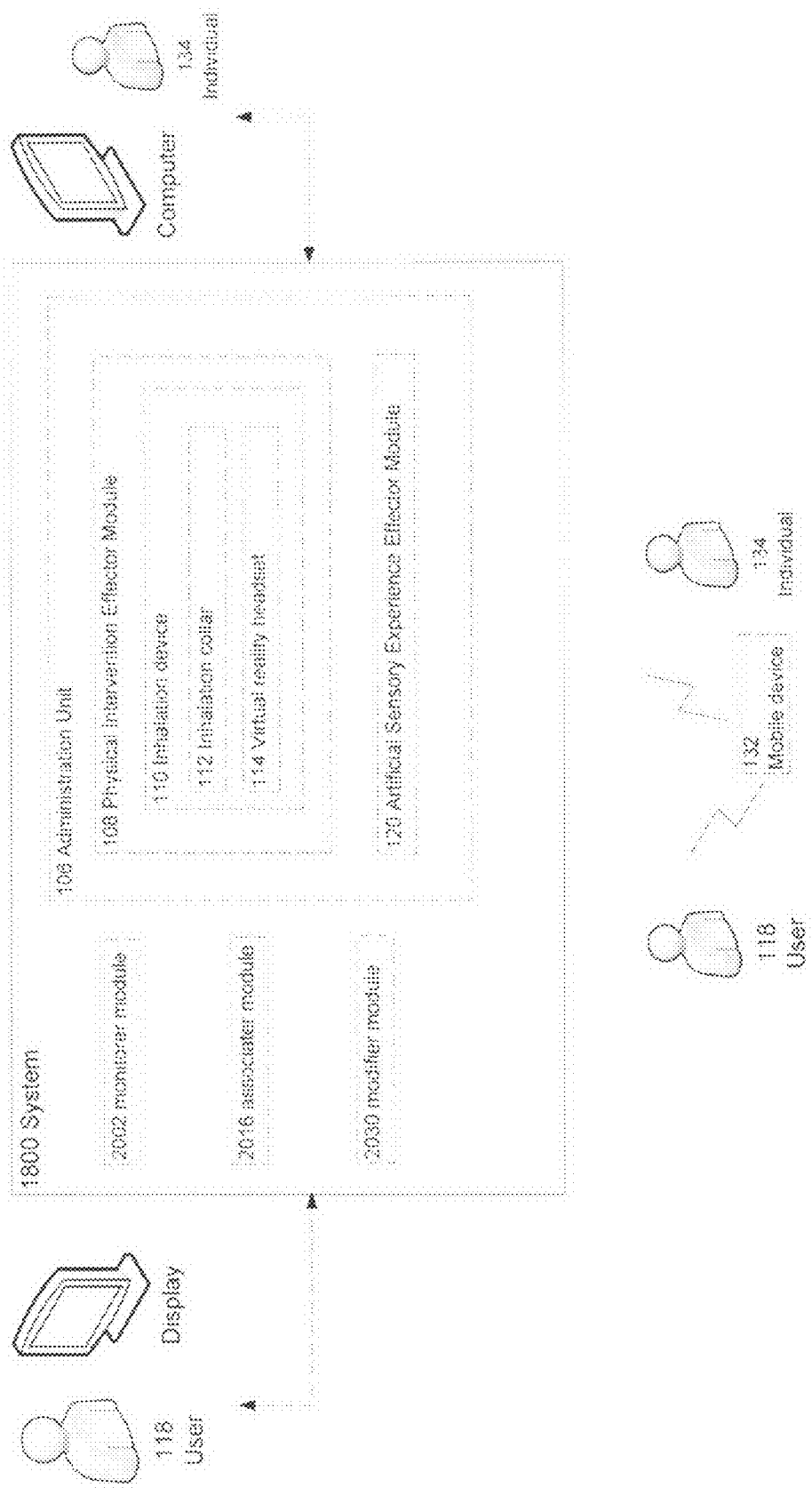
FIG. 18 illustrates an exemplary environment in which one or more technologies may be implemented.

FIG. 18 illustrates system 1800 for monitoring at least one health attribute of an individual during an artificial sensory experience, associating a characteristic of the artificial sensory experience with the at least one health attribute of the individual, and/or modifying at least one of an inhalation device-dispensed bioactive agent or the artificial sensory experience at least partially based on associating a characteristic of the artificial sensory experience with the at least one health attribute of the individual. System 1800 may include monitorer module 2002, associater module 2016, modifier module 2030, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 1800 may include mobile device 132.

Figure 19:
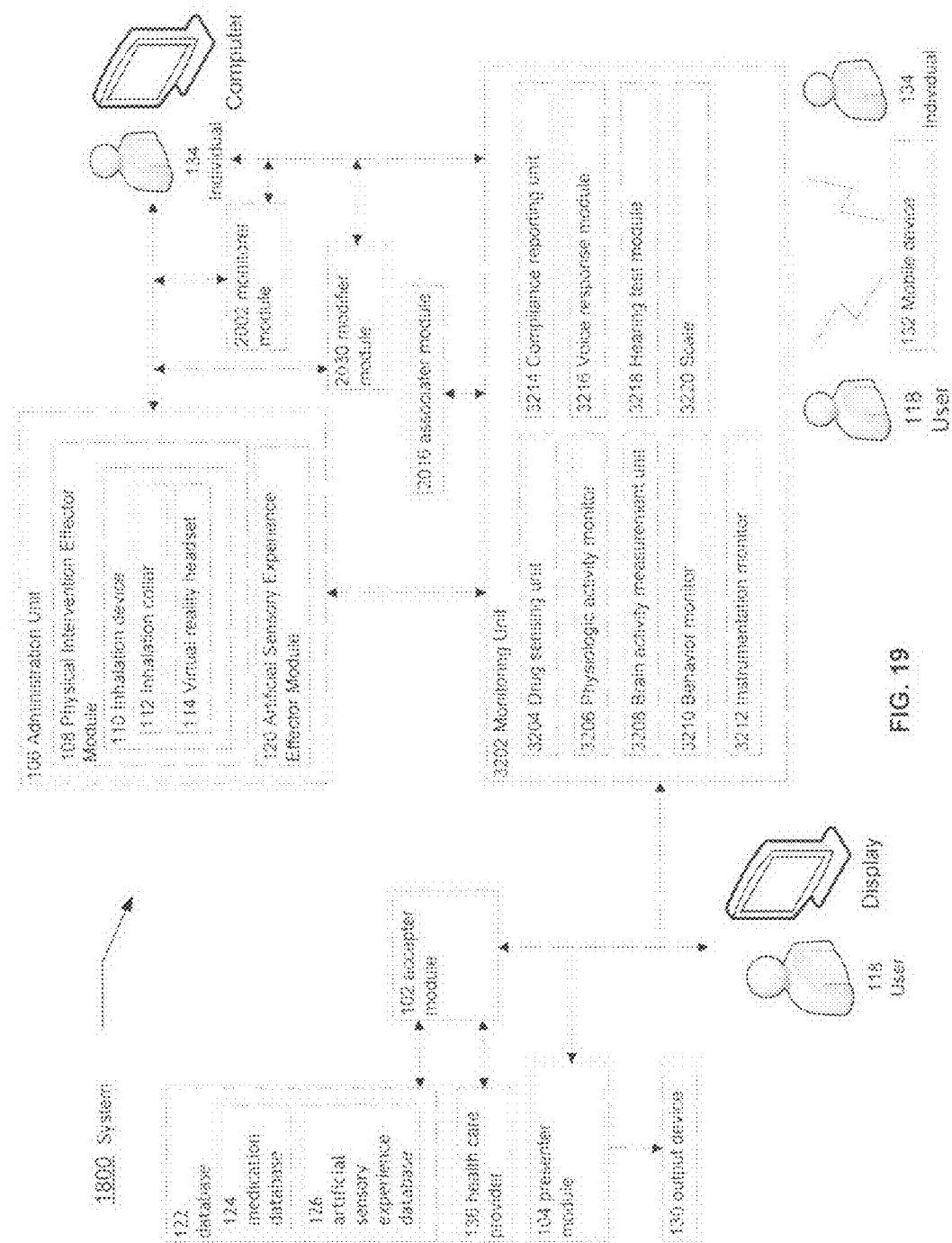
FIG. 19 illustrates an exemplary environment in which one or more technologies may be implemented.

FIG. 19 illustrates system 1800 for monitoring at least one health attribute of an individual during an artificial sensory experience, associating a characteristic of the artificial sensory experience with the at least one health attribute of the individual, and/or modifying at least one of an inhalation device-dispensed bioactive agent or the artificial sensory experience at least partially based on associating a characteristic of the artificial sensory experience with the at least one health attribute of the individual. System 1800 may include monitorer module 2002, associater module 2016, modifier module 2030, accepter module 102, administration unit 106, and/or monitoring unit 3202. Accepter module 102 may receive and/or transmit information and/or data to and/or from user 118, database 122, side effect monitor presenter module 2028, output device 130, and/or health care provider 136. A user may include user 118, individual 134, health care provider 136, a patient, and/or another affected person or entity. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, mobile device 132 may communicate with accepter module 102, presenter module 104, monitorer module 2002, associater module 2016, modifier module 2030, healthcare provider 136, user 118, individual 134, monitoring unit 3202, and/or administration unit 106.

Figure 20:
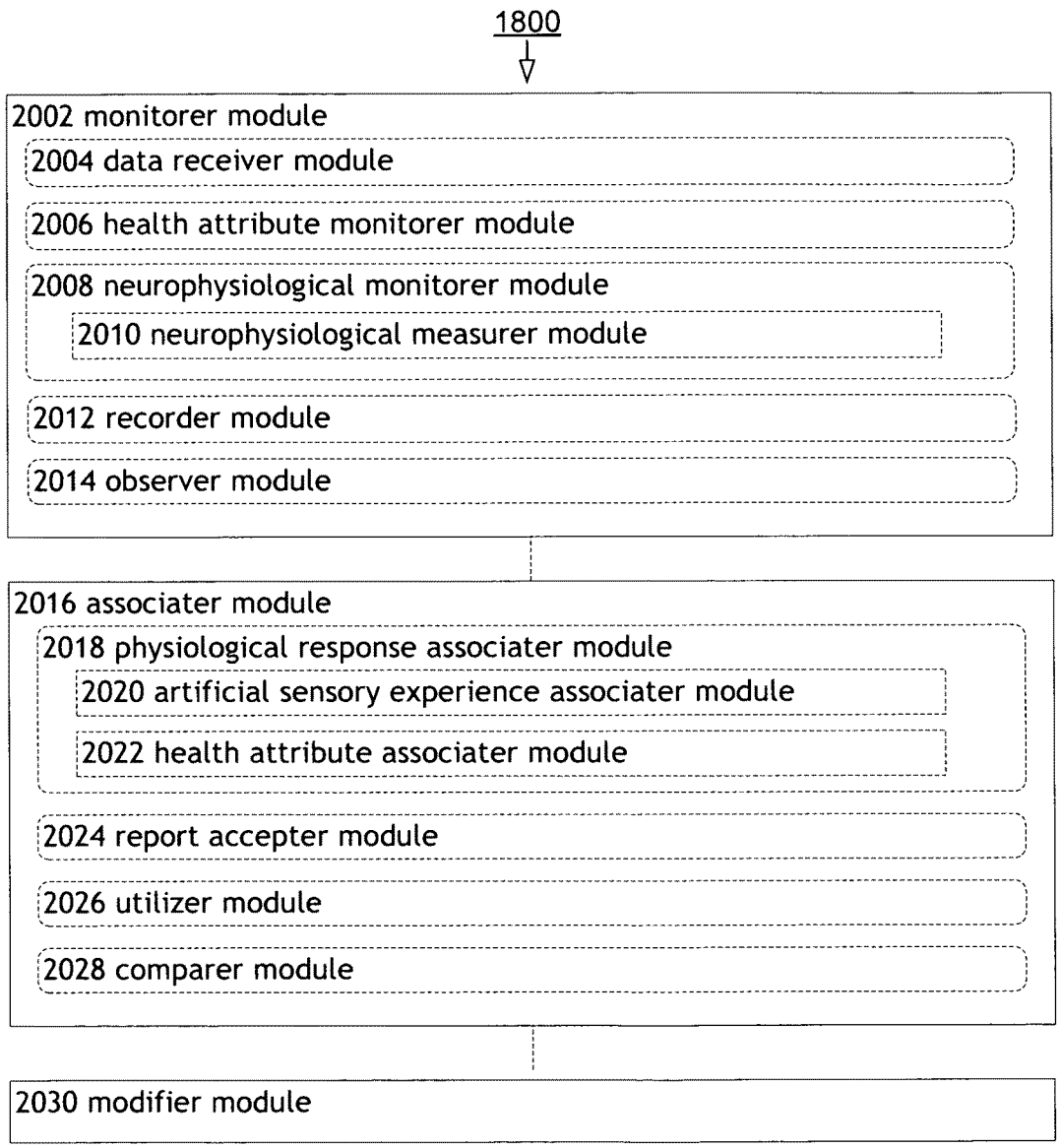
FIG. 20 illustrates an exemplary environment in which one or more technologies may be implemented.

FIG. 20 further illustrates system 1800 including monitorer module 2002, associater module 2016, and/or modifier module 2030. Monitorer module 2002 may include data receiver module 2004, health attribute monitorer module 2006, neurophysiological monitorer module 2008, recorder module 2012, and/or observer module 2014. Neurophysiological monitorer module 2008 may include neurophysiological measurer module 2010. Associater module 2016 may include physiological response associater module 2018, report accepter module 2024, utilizer module 2026, and/or comparer module 2028. Physiological response associater module 2018 may include artificial sensory experience associater module 2020 and/or health attribute associater module 2022.

Figure 21:
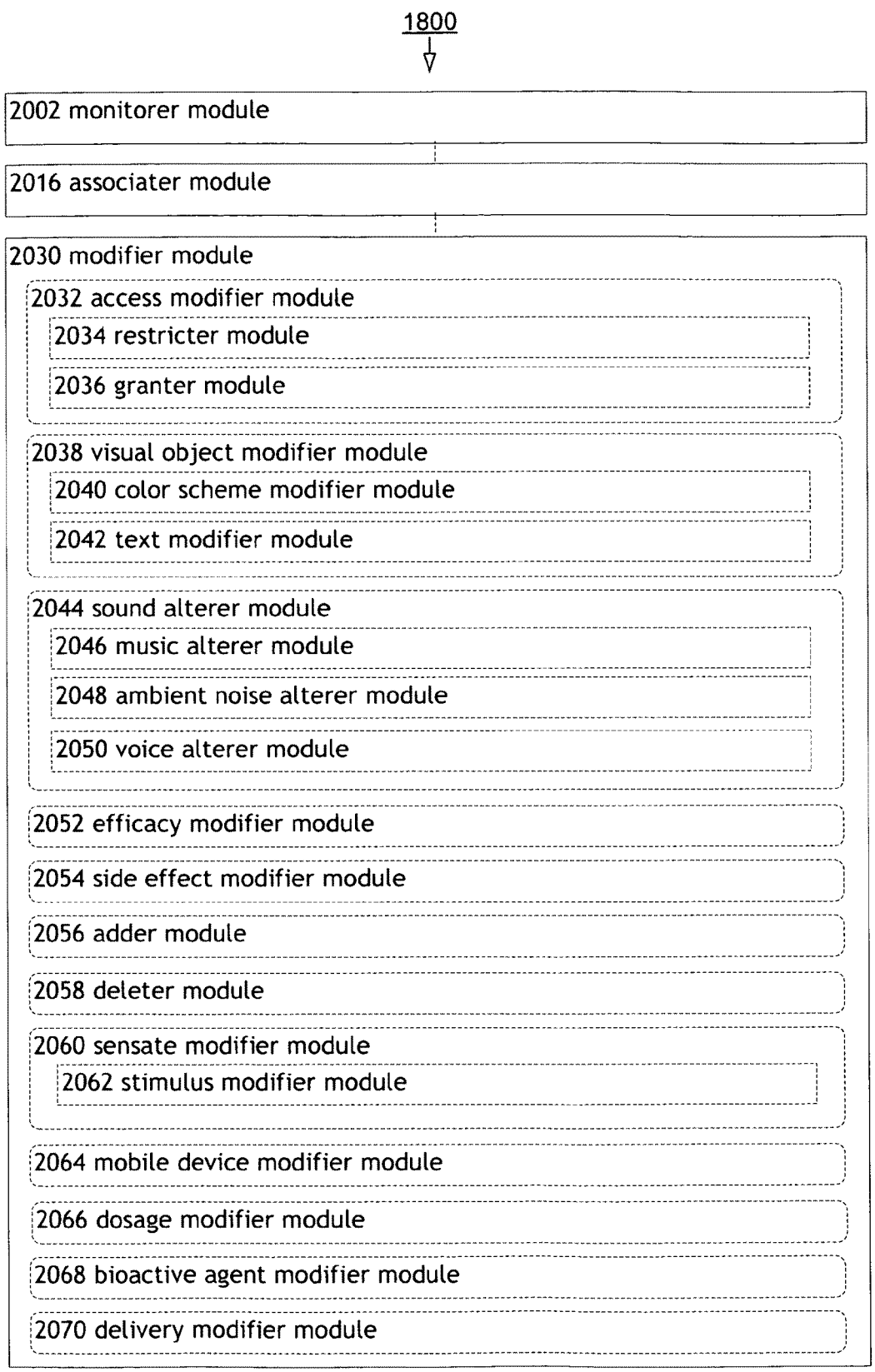
FIG. 21 illustrates an exemplary environment in which one or more technologies may be implemented.

FIG. 21 further illustrates system 1800 including monitorer module 2002, associater module 2016, and/or modifier module 2030. Modifier module 2030 may include access modifier module 2032, visual object modifier module 2038, sound alterer module 2044, efficacy modifier module 2052, side effect modifier module 2054, adder module 2056, deleter module 2058, sensate modifier module 2060, mobile device modifier module 2064, dosage modifier module 2066, bioactive agent modifier module 2068, and/or delivery modifier module 2070. Access modifier module 2032 may include restricter module 2034 and/or granter module 2036. Visual object modifier module 2038 may include color scheme modifier module 2040 and/or text modifier module 2042. Sound alterer module 2044 may include music alterer module 2046, ambient noise alterer module 2048, and/or voice alterer module 2050. Sensate modifier module 2060 may include stimulus modifier module 2062.

System 1800 generally represents instrumentality for monitoring at least one health attribute of an individual during an artificial sensory experience, associating a characteristic of the artificial sensory experience with the at least one health attribute of the individual, and modifying at least one of an inhalation device-dispensed bioactive agent or the artificial sensory experience at least partially based on associating a characteristic of the artificial sensory experience with the at least one health attribute of the individual. The operations of monitoring at least one health attribute of an individual during an artificial sensory experience, associating a characteristic of the artificial sensory experience with the at least one health attribute of the individual, and modifying at least one of an inhalation device-dispensed bioactive agent or the artificial sensory experience at least partially based on associating a characteristic of the artificial sensory experience with the at least one health attribute of the individual may be accomplished electronically, such as with a set of interconnected electrical components, an integrated circuit, and/or a computer processor.

Figure 22:
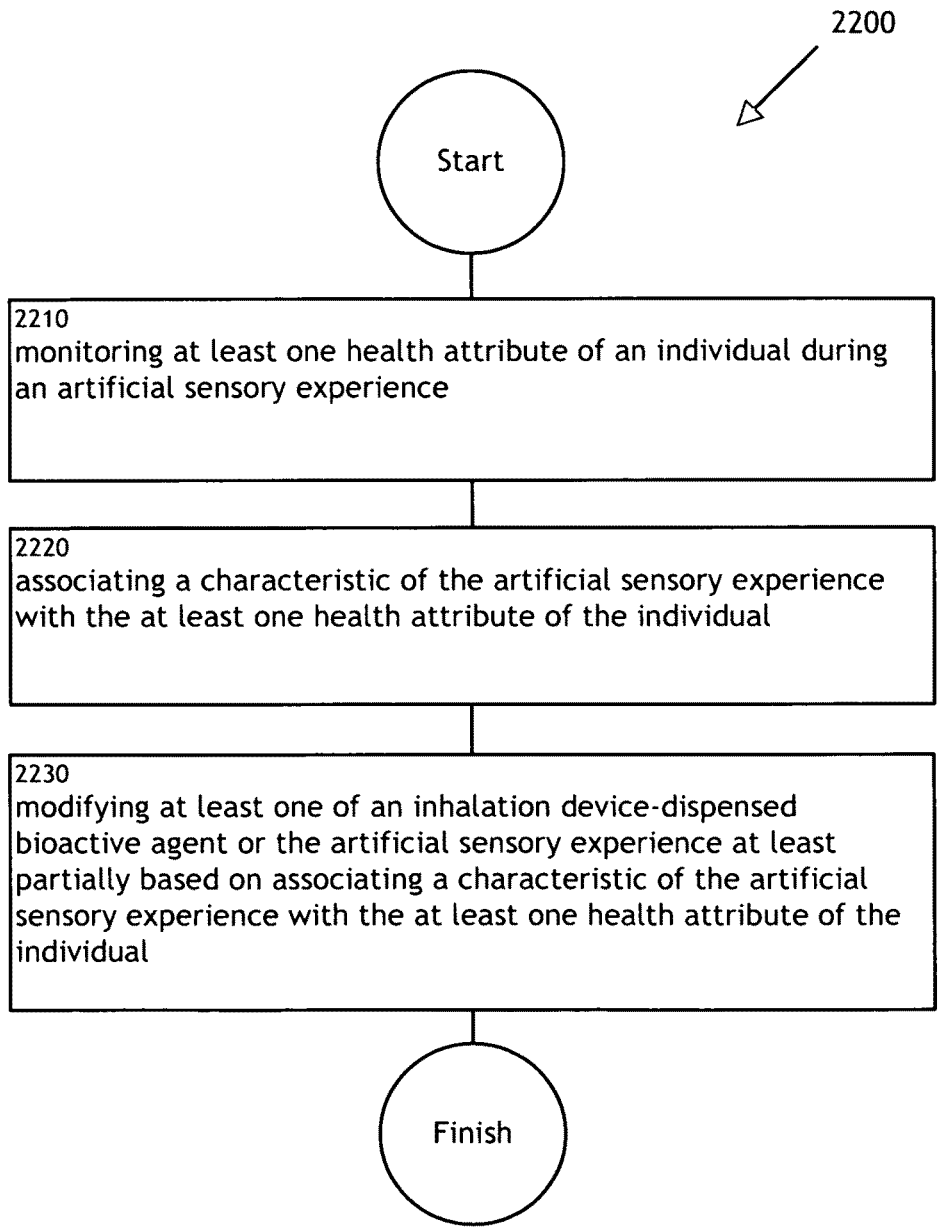
FIG. 22 illustrates an operational flow representing example operations related to combining an inhaled bioactive agent and an artificial sensory experience.

FIG. 22 illustrates an operational flow 2200 representing example operations related to monitoring at least one health attribute of an individual during an artificial sensory experience, associating a characteristic of the artificial sensory experience with the at least one health attribute of the individual, and modifying at least one of an inhalation device-dispensed bioactive agent or the artificial sensory experience at least partially based on associating a characteristic of the artificial sensory experience with the at least one health attribute of the individual. In FIG. 22 and in following figures that include various examples of operational flows, discussion and explanation may be provided with respect to the above-described examples of FIGS. 18 through 21, and/or with respect to other examples and contexts. However, it should be understood that the operational flows may be executed in a number of other environments and contexts, and/or in modified versions of FIGS. 18 through 21. Also, although the various operational flows are presented in the sequence(s) illustrated, it should be understood that the various operations may be performed in other orders than those which are illustrated, or may be performed concurrently.

After a start operation, the operational flow 2200 moves to operation 2210. Operation 2210 depicts monitoring at least one health attribute of an individual during an artificial sensory experience. For example, as shown in FIGS. 18 through 21, monitorer module 2002 may monitor at least one health attribute of an individual during an artificial sensory experience. In one embodiment, monitorer module 2002 may monitor a heart rate while an individual experiences a virtual world. In this embodiment, monitoring the heart rate may enable a health care provider to closely observe the patient and offer quality care. Monitoring may include, for example, observing, recording, detecting, comparing, and/or an ongoing process of collecting and/or analyzing information. A health attribute may include a characterisitic and/or a quality associated with an individual's physical, mental, and/or social well-being. Some examples of a health attribute may include blood pressure, body weight, heart rate, diet, stress level, body temperature, and/or respiratory rate. Other examples of a health attribute may include pupil size, blood glucose amount, a pain scale measurement, speech pitch modulation, and/or facial expression. One example of monitoring a health attribute may be found in Xueliang, H. et al., *A Wireless Pharmaceutical Compliance Monitoring System Based on Magneto-Inductive Sensors*, SENSORS JOURNAL, IEEE, 7(12):1711-19 (2007), which is incorporated herein by reference. In some instances, monitorer module 2002 may include a computer processor and/or medical instrumentation, such as an electrocardiograph.

In another embodiment, monitorer module 2002 may remotely monitor a heart rate while an individual experiences a virtual world. One example of remote monitoring may include a sensor configured to send a signal to a receiver. Other examples of remote monitoring may be found in McGrath, U.S. Pat. No. 7,272,431; Matthews et al., U.S. Pat. No. 7,245,956; Clark et al., U.S. Patent Publication No. 2006/0058694; Harland, C. J. et al., *Electric Potential Probes-New Directions in the Remote Sensing of the Human Body*, MEAS. SCI. TECHNOL. 13: 163-169 (2002); Harland, C. J et al., *Remote detection of human electroencephalograms using ultrahigh input impedance electric potential sensors*, APPL. PHYS. LETT., 81(17) 3284-3286 (2002); and/or McGrath, U.S. Patent Publication No. 2008/0045832, each of which are incorporated herein by reference. In a separate embodiment, monitorer module 2002 may non-invasively monitor pupil size while an individual experiences a virtual world. Some examples of non-invasive monitoring may include Prance, R. J. et al., *Adaptive Electric Potential Sensors for smart signal acquisition and processing*, 2007 Journal of Physics: Conference Series, 76: 012025; Harland, C. J. et al., *High resolution ambulatory electrocardiographic monitoring using wrist-mounted electric potential sensors*, MEAS. SCI. TECHNOL., 14:923-928 (2003); and Abourizk, et al., U.S. Pat. No. 7,226,164, each of which are incorporated herein by reference.

Then, operation 2220 depicts associating a characteristic of the artificial sensory experience with the at least one health attribute of the individual. For example, as shown in FIGS. 18 through 21, associater module 2016 may associate a characteristic of the artificial sensory experience with the at least one health attribute of the individual. In one embodiment, associater module 2016 may associate a characteristic of the artificial sensory experience, such as soothing background music, with a health attribute of an individual, such as a heart rate. Some examples of an artificial sensory experience characteristic may include music, lighting, a color scheme, and/or action in the artificial sensory experience, such as movement and/or simulated fighting in a virtual world gaming environment (World of Warcraft). Associating may include, for example, relating, statistically correlating, and/or linking information and/or data. One further example of associating may be found in Davies, et al., U.S. Patent Publication No. 2008/0212847, which is incorporated herein by reference. In some instances, associater module 2016 may include a computer processor.

Then, operation 2230 depicts modifying at least one of an inhalation device-dispensed bioactive agent or the artificial sensory experience at least partially based on associating a characteristic of the artificial sensory experience with the at least one health attribute of the individual. For example, as shown in FIGS. 18 through 21, modifier module 2030 may modify at least one of an inhalation device-dispensed bioactive agent or the artificial sensory experience at least partly based on associating a characteristic of the artificial sensory experience with the at least one health attribute of the individual. One example of an inhalation device configured to dispense a bioactive agent may include an inhaler used for delivering a bioactive agent into the body using a body airway. Some other examples may include a collar, necklace, and/or a bracelet with a bioactive agent dispenser proximate to the nose, mouth, and/or inhalation route. In one embodiment, modifier module 2030 may modify an inhaled steroid by decreasing a dosage subsequent based on associating an individual's ease of breathing with a mountainous virtual world. In this embodiment, the mountainous virtual world may serve to lessen an individual's elevated anxiety and may encourage a peaceful and/or relaxing atmosphere, which may be indicated by the eased and/or relaxed breathing. In another embodiment, modifier module 2030 may decrease an inhaled antidepressant dosage based on an individual's decreased blood pressure while experiencing a virtual world configured to facilitate a happy environment. In this embodiment, the decreased blood pressure and the virtual world may be designed to reduce depression and may warrant a modification of a medication, such as a decreased inhaled antidepressant dosage. Some examples of an artificial sensory experience may include a virtual experience, such as an online game or a social networking site, and/or a real-world sensory stimulus, such as a smell and/or a sight. Other examples of modifying an artificial sensory experience may include changing a computer game and/or changing a computer display background. An additional example of modifying an artificial sensory experience may include a changing a virtual game utilizing a neuroheadset having sensors for detecting mental states based on, for example, electrical signals and/or blood flow in the brain. See, for example, headsets manufactured by Emotiv Systems, Inc. In some instances, modifier module 2030 may include a computer processor.

Figure 23:
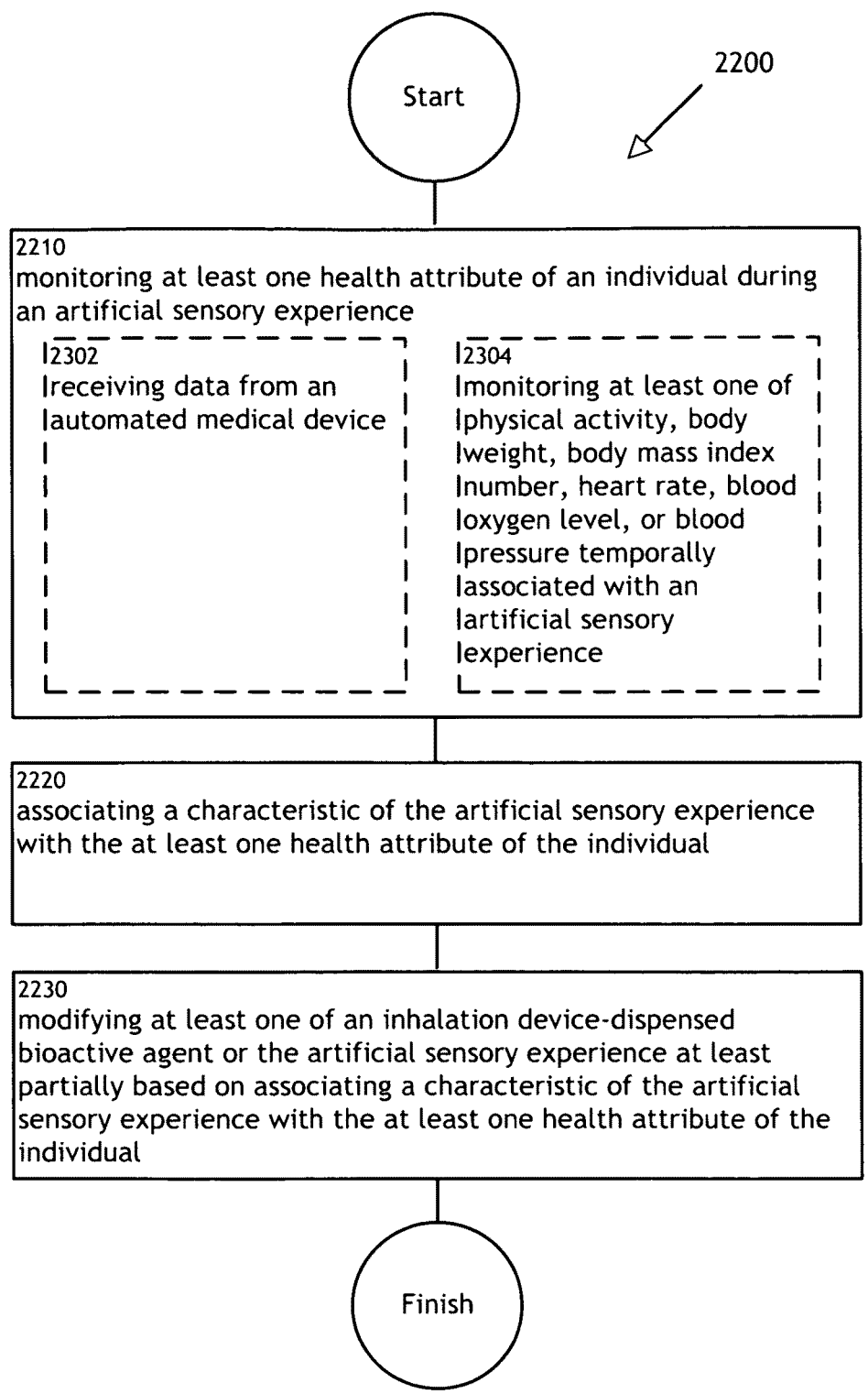
FIG. 23 illustrates an alternative embodiment of the operational flow of FIG. 22.

FIG. 23 illustrates alternative embodiments of the example operational flow 2200 of FIG. 22. FIG. 23 illustrates example embodiments where operation 2210 may include at least one additional operation. Additional operations may include operation 2302, and/or operation 2304.

Operation 2302 illustrates receiving data from an automated medical device. For example, as shown in FIGS. 18 through 21, data receiver module 2004 may receive data from an automated medical device, such as an electrocardiograph. An automated medical device may include a medical monitor and/or a device that senses a patient's vital signs and communicates the results, such as to a monitor and/or a user 118. Some examples of an automated medical device may include an electrocardiograph, such as a Holter monitor, medical imaging machines, such as an ultrasound machine and/or a magnetic resonance imaging machine, analysis instrumentation, such as a blood glucose meter, and/or a pulse oximeter. Other examples of an automated medical device may include a pedometer, a heart rate monitor, a blood pressure monitor, a body-fat analyzer, and/or a neurophysiological monitor. Additionally, a multi-parameter automated medical device may simultaneously measure and/or track multiple vital signs. One example of an automated device may include a tele-medicine application, further described in Jeanpierre, L.

et al., *Automated medical diagnosis with fuzzy stochastic models: monitoring chronic diseases*, ACTA BIOTHERETICA, 52(4):291-311 (2004), which is incorporated herein by reference. In some instances, data receiver module 2004 may include a computer processor, a monitor coupled to a computer processor, and/or other medical devices, such as those described above.

Operation 2304 illustrates monitoring at least one of physical activity, body weight, body mass index number, heart rate, blood oxygen level, or blood pressure temporally associated with an artificial sensory experience. For example, as shown in FIGS. 18 through 21, health attribute monitorer module 2006 may monitor an individual's heart rate. Physical activity may include any form of exercise, movement, and/or bodily activity. Some examples of a physical activity may include exercise, body movement, walking, running, and/or muscle stretching. Monitoring physical activity may include using a pedometer, an accelerometer, for example, available from New-Lifestyles, Inc., Lee's Summit, Mo., and/or other devices, such as actometers, further discussed in Zhang et al., *Measurement of Human Daily Physical Activity*, OBESITY RESEARCH, 11(1):33-40 (2003), which is incorporated herein by reference.

Monitoring a body weight and/or a body mass index may include using a scale and/or a computing device. In one embodiment, health attribute monitorer module 2006 may monitor a body mass index of an individual experiencing a Wii Fitness game while being administered a weight loss medication by using a scale 3220 coupled with a computer processor. In the same embodiment, scale 3220 and computer processor may constantly monitor the body mass index of the individual 134. Further, monitoring a heart rate may include measuring work done by the heart, such as measuring beats per unit time and/or a pulse. Monitoring a blood oxygen level may include utilizing a pulse oximeter and/or measuring oxygen saturation directly through a blood sample. Monitoring blood pressure may include utilizing a sphygmomanometer, which may be coupled to a computer processor or other monitoring device. Monitoring physical activity, a heart rate, a blood oxygen level, and/or blood pressure when an individual is experiencing an artificial sensory experience may serve to determine the efficacy of a bioactive agent. For example, when an antianxiety medication is administered to an individual prior to and/or during an artificial sensory experience, such as a spider world designed to overcome a spider phobia, health attribute monitorer module 2006 may monitor a heart rate in order to determine whether the antianxiety medication is effective. In the above example, the individual's heart rate may decrease due to a decrease in anxiety as the antianxiety medication takes effect, which may indicate drug efficacy. Additionally, health attribute monitorer module 2006 may monitor before, during, and/or after an individual experiences an artificial sensory experience. In some instances, health attribute monitorer module 2006 may include a computer processor and/or other medical instrumentation, such as that discussed herein.

Figure 24:
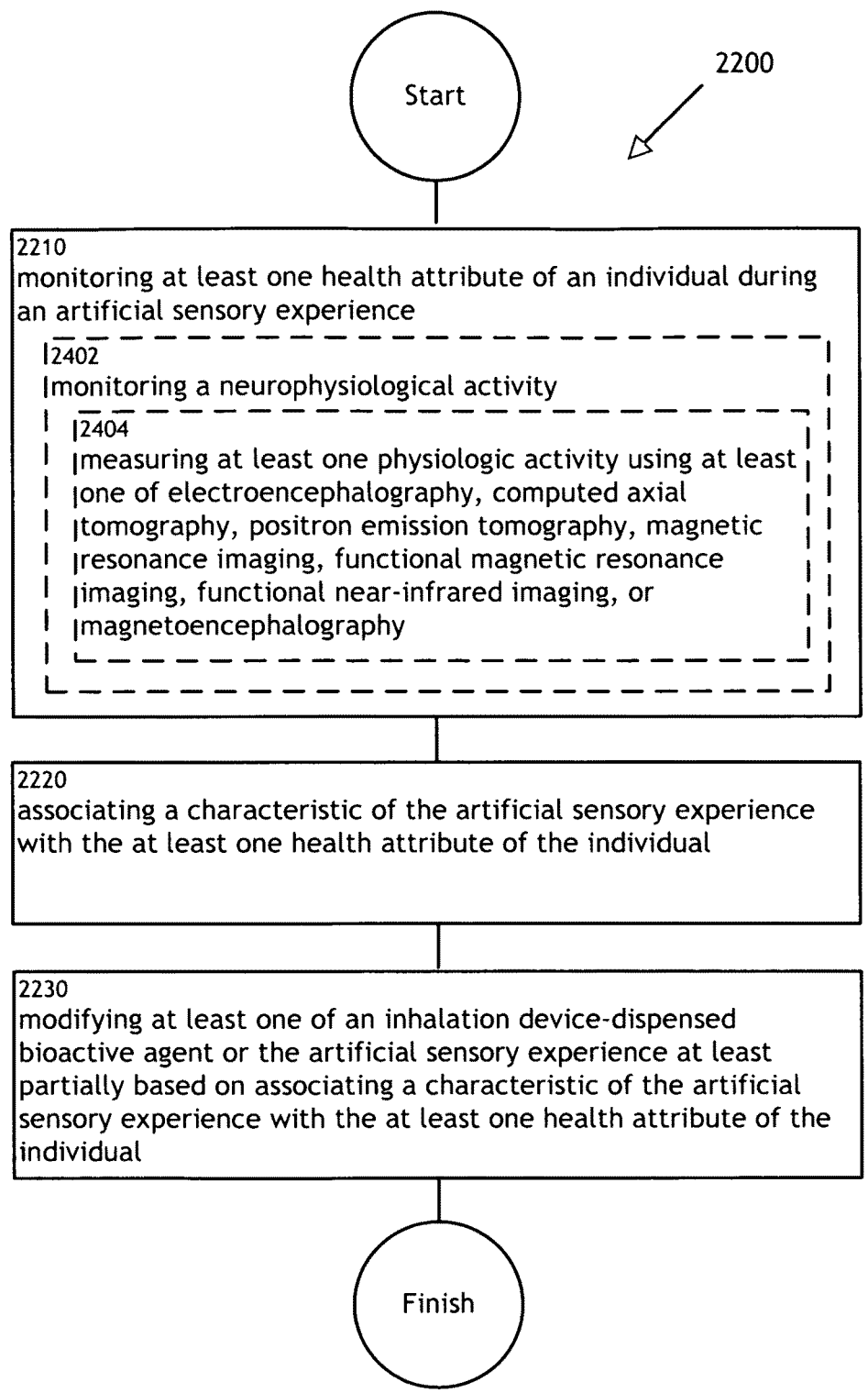
FIG. 24 illustrates an alternative embodiment of the operational flow of FIG. 22.

FIG. 24 illustrates alternative embodiments of the example operational flow 2200 of FIG. 22. FIG. 24 illustrates example embodiments where operation 2210 may include at least one additional operation. Additional operations may include operation 2402, and/or operation 2404.

Operation 2402 illustrates monitoring a neurophysiological activity. For example, as shown in FIGS. 18 through 21, neurophysiological monitorer module 2008 may monitor a neurophysiological measurement, such as, for example, a measurement of the activation signal of muscles (electromyography) and/or the measurement of transcranial magnetic stimulation. A neurophysiological measurement may include a measurement of the brain, nervous system, and/or neuromonitoring. In some instances, neurophysiological activity monitorer module 3408 may include a computer processor and/or a medical device, such as device configured to measure somatosensory evoked potentials (SSEPs), auditory brainstem response (ABR), and/or scalp sensors used in electroencephalography (EEG). In some instances, neurophysiological monitorer module 2008 may include a computer processor and/or medical instrumentation.

Further, operation 2404 illustrates measuring at least one physiologic activity using at least one of electroencephalography, computed axial tomography, positron emission tomography, magnetic resonance imaging, functional magnetic resonance imaging, functional near-infrared imaging, or magnetoencephalography. For example, as shown in FIGS. 18 through 21, neurophysiological measurer module 2010 may measure at least one physiologic activity using at least one of electroencephalography, computed axial tomography, positron emission tomography, magnetic resonance imaging, functional magnetic resonance imaging, functional near-infrared imaging, or magnetoencephalography. In some instances, neurophysiological measurer module 2010 may include a computer processor, and/or a medical device, such as an apparatus configured to perform a computed axial tomography scan.

Electroencephalography may include measuring the electrical activity of the brain by recording from electrodes placed on the scalp or, in special cases, subdurally, or in the cerebral cortex. The resulting traces are known as an electroencephalogram (EEG) and represent a summation of post-synaptic potentials from a large number of neurons. EEG is most sensitive to a particular set of post-synaptic potentials: those which are generated in superficial layers of the cortex, on the crests of gyri directly abutting the skull and radial to the skull. Dendrites that are deeper in the cortex, inside sulci, are in midline or deep structures (such as the cingulate gyrus or hippocampus) or that produce currents that are tangential to the skull make a smaller contribution to the EEG signal.

One application of EEG is event-related potential (ERP) analysis. An ERP is any measured brain response that is directly the result of a thought or perception. ERPs can be reliably measured using electroencephalography (EEG), a procedure that measures electrical activity of the brain, typically through the skull and scalp. As the EEG reflects thousands of simultaneously ongoing brain processes, the brain response to a certain stimulus or event of interest is usually not visible in the EEG. One of the most robust features of the ERP response is a response to unpredictable stimuli. This response is known as the P300 (P3) and manifests as a positive deflection in voltage approximately 300 milliseconds after the stimulus is presented.

A two-channel wireless brain wave monitoring system powered by a thermo-electric generator has been developed by IMEC (Interuniversity Microelectronics Centre, Leuven, Belgium). This device uses the body heat dissipated naturally from the forehead as a means to generate its electrical power. The wearable EEG system operates autonomously with no need to change or recharge batteries. The EEG monitor prototype is wearable and integrated into a headband where it consumes 0.8 milliwatts. A digital signal processing block encodes extracted EEG data, which is sent to a PC via a 2.4-GHz wireless radio link. The thermoelectric generator is mounted on the forehead and converts the heat flow between the skin and air into electrical power. The generator is composed of 10 thermoelectric units interconnected in a flexible way. At room temperature, the generated power is about 2 to 2.5-mW or 0.03-mW per square centimeter, which is the theoretical limit of power generation from the human skin. Such a device is proposed to associate emotion with EEG signals. See Clarke, "IMEC has a brain wave: feed EEG emotion back into games," EE Times online, http://www.ee-times.eu/design/202801063 (Nov. 1, 2007).

Computed axial tomography may include medical imaging employing tomography and digital geometry processing for generating a three-dimensional image of the inside of an object from a large series of two-dimensional X-ray images taken around a single axis of rotation. Positron emission tomography may include a nuclear medicine imaging technique, which produces a three-dimensional image and/or map of at least one functional process in the body. The system detects pairs of gamma rays emitted indirectly by a positron-emitting radionuclide (a tracer), which is introduced into the body on a biologically active molecule. Images of tracer concentration in 3-dimensional space within the body may then be reconstructed by computer analysis. Magnetic resonance imaging may include a medical imaging technique using a magnetic field to align the nuclear magnetization of hydrogen atoms in water in the body, resulting in an image of the body. Functional magnetic resonance imaging may include and imaging method for measuring haemodynamic response related to neural activity in the brain or spinal cord. Functional near-infrared imaging (fNIR) may include a spectroscopic neuro-imaging method for measuring the level of neuronal activity in the brain. Functional near-infrared imaging (fNIR) is based on neuro-vascular coupling, or the relationship between metabolic activity and oxygen level (oxygenated hemoglobin) in feeding blood vessels.

Magnetoencephalography includes measuring the magnetic fields produced by electrical activity in the brain using magnetometers such as superconducting quantum interference devices (SQUIDs) or other devices. Smaller magnetometers are in development, including a mini-magnetometer that uses a single milliwatt infrared laser to excite rubidium in the context of an applied perpendicular magnetic field. The amount of laser light absorbed by the rubidium atoms varies predictably with the magnetic field, providing a reference scale for measuring the field. The stronger the magnetic field, the more light is absorbed. Such a system is currently sensitive to the 70 fT range, and is expected to increase in sensitivity to the 10 fT range. See Physorg.com, "New mini-sensor may have biomedical and security applications," Nov. 1, 2007, http://www.physorg.com/news13151078.html, which is incorporated herein by reference.

Figure 25:
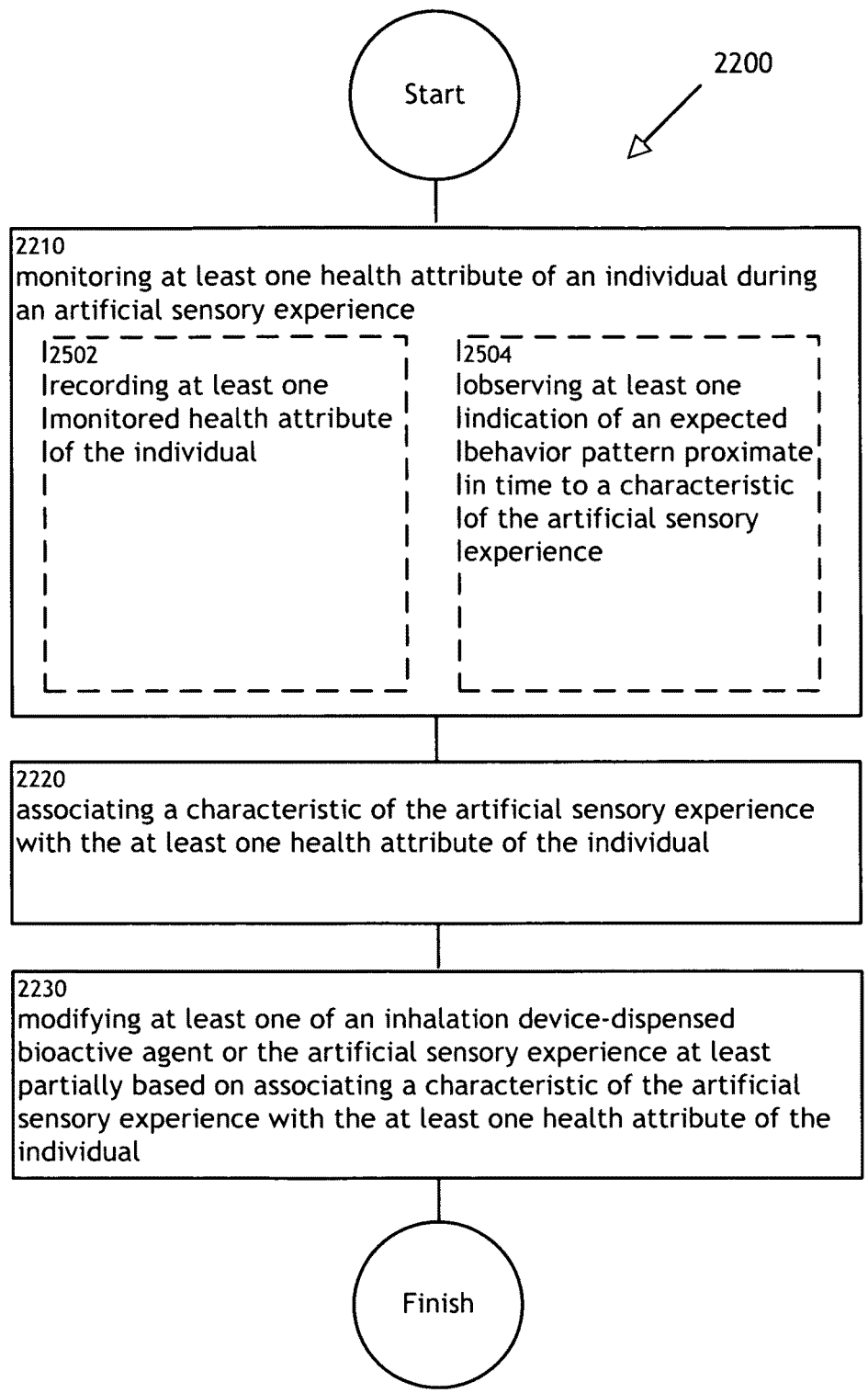
FIG. 25 illustrates an alternative embodiment of the operational flow of FIG. 22.

FIG. 25 illustrates alternative embodiments of the example operational flow 2200 of FIG. 22. FIG. 25 illustrates example embodiments where operation 2210 may include at least one additional operation. Additional operations may include operation 2502, and/or operation 2504.

Operation 2502 illustrates recording at least one monitored health attribute of the individual. For example, as shown in FIGS. 18 through 21, recorder module 2012 may record at least one monitored health attribute of the individual. Recording a monitored health attribute may include capturing data, including the monitored health attribute, to a record and/or a format stored on a storage medium. In one embodiment, recorder module 2012 may record a monitored heart rate onto a hard disk drive. Other examples of a record and/or storage medium may include flash memory devices, a tape drive, circuitry with non-volatile and/or volatile RAM, an optical disc, for example a CD and/or DVD, and/or a paper record, such as a collection of printed spreadsheets and/or other lists of data. In an additional embodiment, recorder module 2012 may record a monitored health attribute by utilizing data acquisition software. Further discussion of data acquisition may be found in Green, T. et al., *PC-Based Medical Data Acquisition and Analysis, cbms*, p. 0159, EIGHTH IEEE SYMPOSIUM ON COMPUTER-BASED MEDICAL SYSTEMS (CBMS'95), 1995, which is incorporated herein by reference. In some instances, recorder module 2012 may include a computer processor and/or other data logging instrumentation, such as NI CompactDAQ hardware, available from National Instruments, Austin, Tex. (http://www.ni.com/dataacquisition/compactdaq/).

Operation 2504 illustrates observing at least one indication of an expected behavior pattern proximate in time to a characteristic of the artificial sensory experience. For example, as shown in FIGS. 18 through 21, observer module 2014 may observe at least one indication of an expected behavior pattern proximate in time to a characteristic of the artificial sensory experience. In one embodiment, observer module 2014 may observe an elevated respiratory rate and increased sweating proximate in time to an individual experiencing an elevated height in a virtual world designed to help the individual overcome acrophobia, or a phobia of heights. Observing an indication of an expected behavior pattern proximate in time to an artificial sensory experience characteristic may indicate a likelihood of causality by the artificial sensory experience characteristic on the expected behavior pattern. In some instances, observer module 2014 may include a computer processor and/or medical instrumentation, such as heart rate monitor coupled to a computer processor configured to statistically link and/or correlate information.

Figure 26:
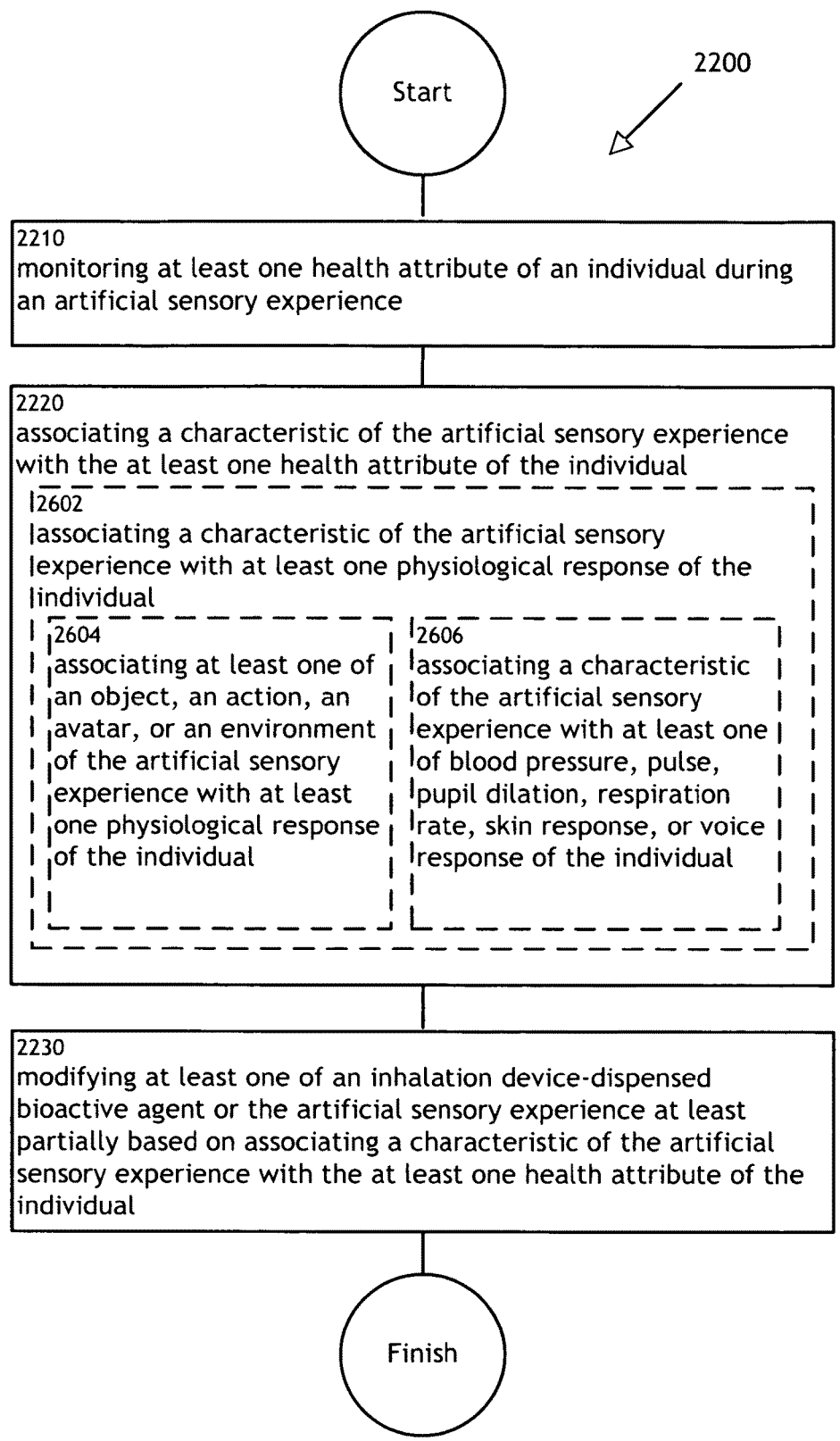
FIG. 26 illustrates an alternative embodiment of the operational flow of FIG. 22.

FIG. 26 illustrates alternative embodiments of the example operational flow 2200 of FIG. 22. FIG. 26 illustrates example embodiments where operation 2220 may include at least one additional operation. Additional operations may include operation 2602, operation 2604, and/or operation 2606.

Operation 2602 illustrates associating a characteristic of the artificial sensory experience with at least one physiological response of the individual. For example, as shown in FIGS. 18 through 21, physiological response associater module 2018 may associate a characteristic of the artificial sensory experience with at least one physiological response of the individual. In one embodiment, physiological response associater module 2018 may associate soothing music in an artificial sensory experience with an individual's Lowered blood pressure and reduced sweating. In this embodiment, associating an artificial sensory experience characteristic with a physiological response may serve to enable a health care professional to better meet the needs of the individual. In some instances, physiological response associater module 2018 may include a computer processor.

Further, operation 2604 illustrates associating at Least one of an object, an action, an avatar, or an environment of the artificial sensory experience with at least one physiological response of the individual. For example, as shown in FIGS. 18 through 21, artificial sensory experience associater module 2020 may associate at least one of an object, an action, an avatar, or an environment of the artificial sensory experience with at least one physiological response of the individual. In one embodiment, artificial sensory experience associater module 2020 may associate an artificial sensory experience environment with an individual's pulse. Some examples of an object of an artificial sensory experience may include a background, associated music, and/or a visual observation, such as a landscape. Some examples of an action may include an action by an avatar, an action by a virtual game, such as a level advancement, and/or an action which may prompt the user to act, such as a textual based set of questions. An avatar may include a graphical representation of a character. Some examples of an artificial sensory experience environment may include a landscape and/or a circumstance in which the individual and/or an avatar controlled by the individual may be placed. In some instances, artificial sensory experience associater module 2020 may include a computer processor.

Further, operation 2606 illustrates associating a characteristic of the artificial sensory experience with at least one of blood pressure, pulse, pupil dilation, respiration rate, skin response, or voice response of the individual. For example, as shown in FIGS. 18 through 21, health attribute associater module 2022 may associate a characteristic of the artificial sensory experience with at Least one of blood pressure, pulse, pupil dilation, respiration rate, skin response, or voice response of the individual. In one embodiment, health attribute associater module 2022 may associate a set of avatar interactions in a virtual world with a skin response, such as increased sweating, of an individual. Such an association may allow a health care provider to modify a therapy, for example increase an antianxiety medication. In another embodiment, health attribute associater module 2022 may associate a lighting scheme in a virtual world with an increased pulse in an individual. In this embodiment, increased pulse may indicate a decrease in depression and may indicate to a health care professional a medication adjustment may be needed. A change and/or a certain measurement of blood pressure, pulse, pupil dilation, respiration rate, skin response, and/or voice response may indicate a modification of an artificial sensory experience and/or a bioactive agent may be needed and/or desired. In some instances, health attribute associater module 2022 may include a computer processor.

Figure 27:
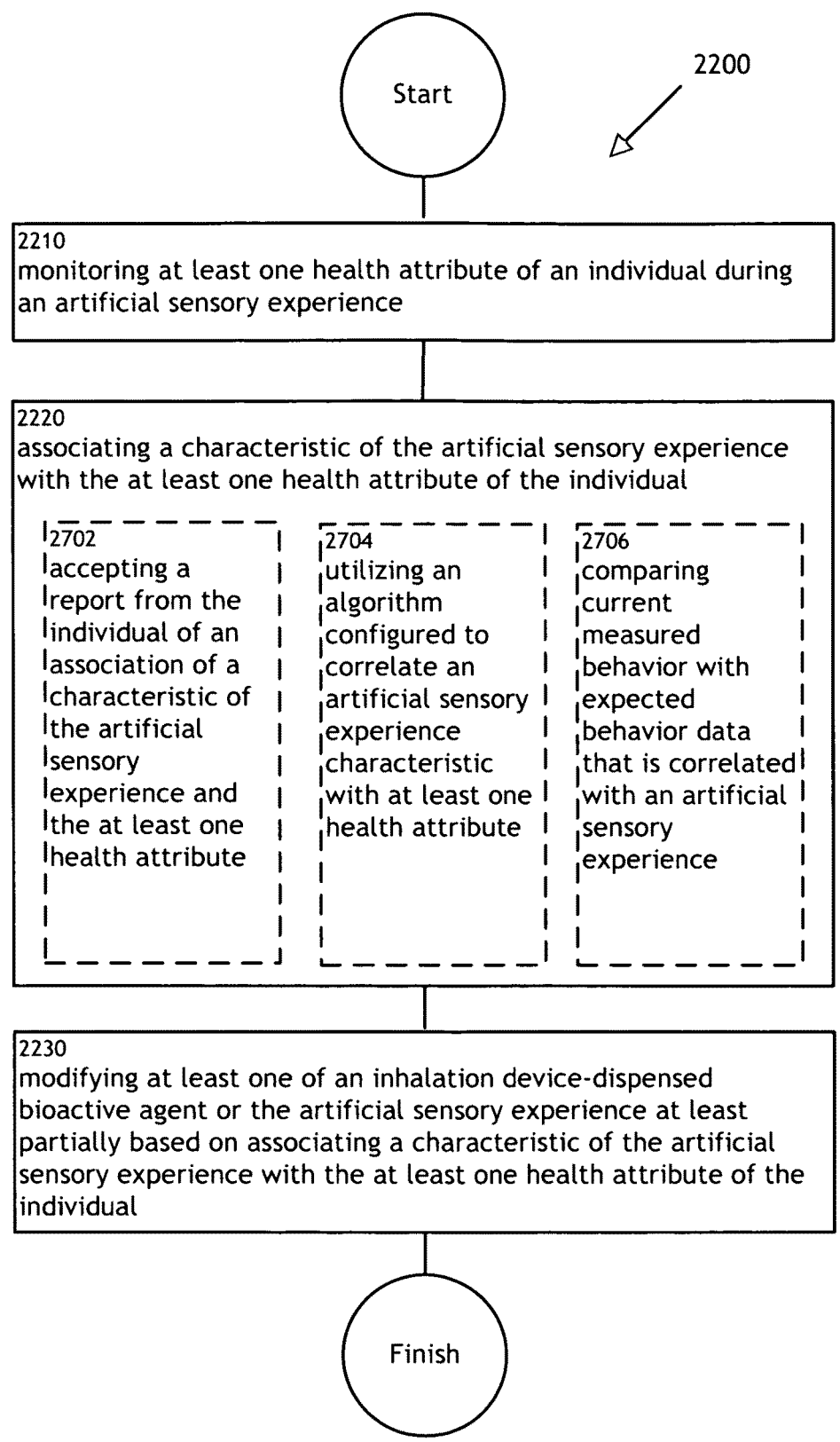
FIG. 27 illustrates an alternative embodiment of the operational flow of FIG. 22.

FIG. 27 illustrates alternative embodiments of the example operational flow 2200 of FIG. 22. FIG. 27 illustrates example embodiments where operation 2220 may include at least one additional operation. Additional operations may include operation 2702, operation 2704, and/or operation 2706.

Operation 2702 illustrates accepting a report from the individual of an association of a characteristic of the artificial sensory experience and the at least one health attribute. For example, as shown in FIGS. 18 through 21, report accepter module 2024 may accept a report from the individual of an association of a characteristic of the artificial sensory experience and the at least one health attribute. In one embodiment, report accepter module 2024 may accept a self evaluation from an individual of an amount of breathing difficulty that the individual feels when experiencing an artificial sensory experience, such as an online game (Second Life). In this embodiment, breathing difficulty may indicate stress. A report from an individual may include any type of input from the individual. One example of a report from an individual may include a self evaluation, such as an evaluation of how much pain the individual is experiencing. Another example of a report from an individual may be found in Chikovani, et al., U.S. Pat. No. 6,383,135, which is incorporated herein by reference. In some instances, report accepter module 2024 may include a computer processor.

Operation 2704 illustrates utilizing an algorithm configured to correlate an artificial sensory experience characteristic with at least one health attribute. For example, as shown in FIGS. 18 through 21, utilizer module 2026 may utilize an algorithm configured to correlate an artificial sensory experience characteristic with at least one health attribute. In one embodiment, utilizer module 2026 may utilize an algorithm for correlating a length of a virtual experience designed to reduce stress and an amount of stress felt by the individual, where the individual may input a result from a self evaluation. A further example of utilizing an algorithm may be found in Kurtberg, et al., U.S. Pat. No. 6,487,520, which is incorporated herein by reference. In some instances, utilizer module 2026 may include a computer processor.

Operation 2706 illustrates comparing current measured behavior with expected behavior data that is correlated with an artificial sensory experience. For example, as shown in FIGS. 18 through 21, comparer module 2028 may compare current measured behavior with expected behavior data that is correlated with an artificial sensory experience. In one embodiment, comparer module 2028 may compare an individual's respiratory rate when experiencing an artificial sensory experience and a database including information regarding an expected respiratory rate correlated with at least a similar artificial sensory experience. Comparing current measured behavior with expected behavior data correlated with an artificial sensory experience may be beneficial, for example, when determining if an individual is responding normally or abnormally to an artificial sensory experience. By comparing current behavior with past behavior, a health professional may be able to determine the efficacy of an artificial sensory experience and/or a bioactive agent therapy. In some instances, comparer module 2028 may include a computer processor.

FIG. 28 illustrates alternative embodiments of the example operational flow 2200 of FIG. 22. FIG. 28 illustrates example embodiments where operation 2230 may include at least one additional operation. Additional operations may include operation 2802, operation 2804, and/or operation 2806.

Operation 2802 illustrates modifying access to at least a portion of the artificial sensory experience. For example, as shown in FIGS. 18 through 21, access modifier module 2032 may modify access to a portion of the artificial sensory experience, for example to alter at least one effect of the bioactive agent. In one instance, access modifier module 2032 may modify access to a portion of an artificial sensory experience including a photo gallery portion of a social networking website. Such modified access may, for example white being administered an antidepressant, function therapeutically to prevent access of an individual to potentially depressing, stressful, or otherwise triggering sensory experiences, and/or the modified access may involve presentation of a sensory experience that affirmatively improves a condition (e.g., bright sunny images for a clinically depressed individual). In some instances, access modifier module 2032 may include a computer processor.

Further, operation 2804 illustrates restricting access to at least a portion of the artificial sensory experience. For example, as shown in FIGS. 18 through 21, restricter module 2034 may restrict access to at least a portion of the artificial sensory experience. In one instance, restricter module 2034 may restrict access to a portion of a virtual world designed to overcome a flying phobia, where access to a portion of a simulated flying experience is prevented, for example, a jet take-off portion. In this instance, the most stressful portion of the flight simulation may be avoided. In some instances, restricter module 2034 may include a computer processor.

Further, operation 2806 illustrates granting access to at least a portion of the artificial sensory experience. For example, as shown in FIGS. 18 through 21, granter module 2036 may grant access to at least a portion of the artificial sensory experience. In one instance and continuing with the above example, granter module 2036 may grant access to at least a portion of a virtual world designed to overcome a flying phobia, where access to a portion of a simulated flying experience is granted, including a jet landing portion. Such a simulation presenting gradually increasing contact with the object of the fear may serve to provide conditioning for the individual to eventually overcome the phobia. In some instances, granter module 2036 may include a computer processor.

Figure 29:
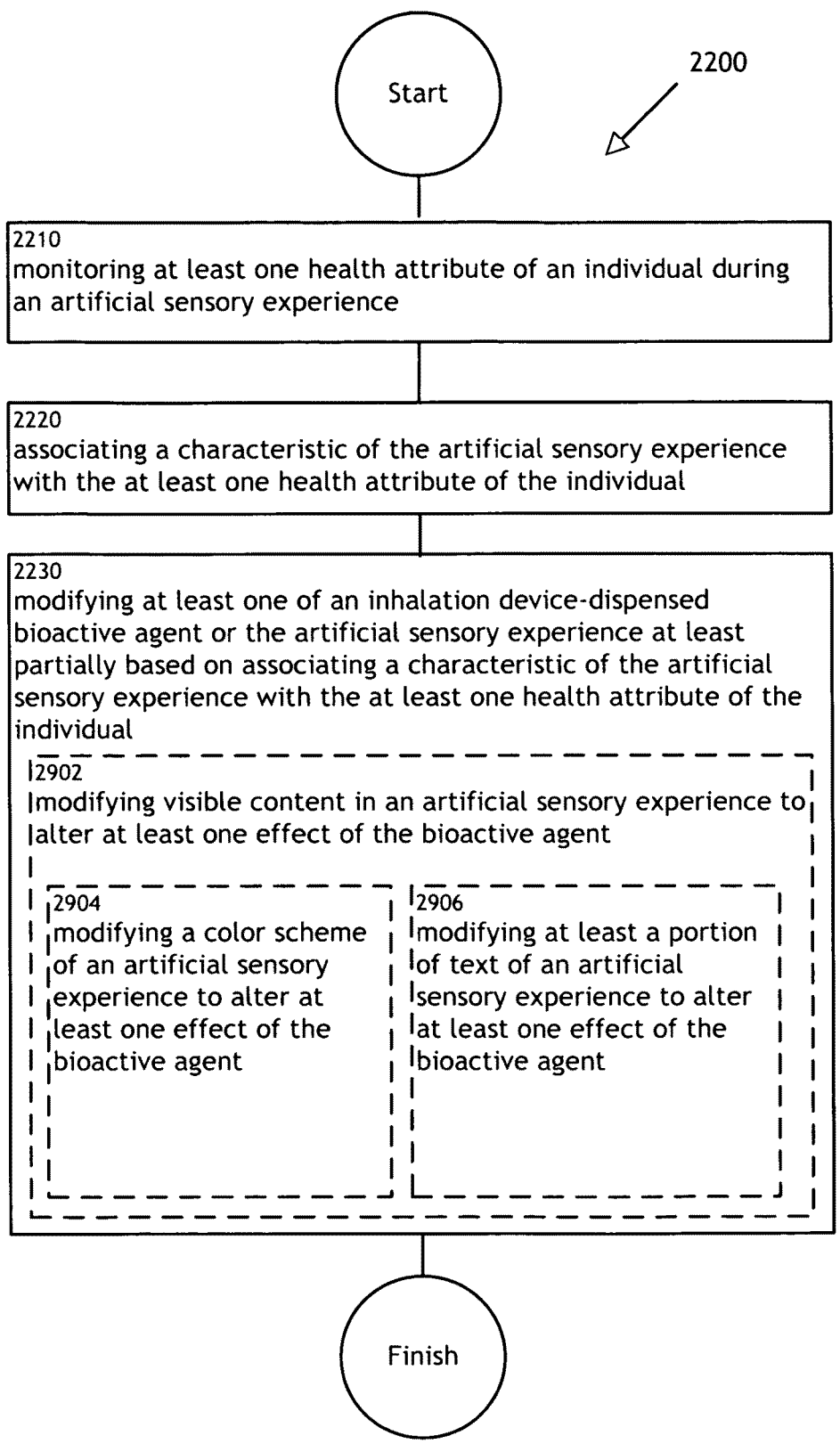
FIG. 29 illustrates an alternative embodiment of the operational flow of FIG. 22.

FIG. 29 illustrates alternative embodiments of the example operational flow 2200 of FIG. 22. FIG. 29 illustrates example embodiments where operation 2230 may include at least one additional operation. Additional operations may include operation 2902, operation 2904, and/or operation 2906.

Operation 2902 illustrates modifying visible content in an artificial sensory experience to alter at least one effect of the bioactive agent. For example, as shown in FIGS. 18 through 21, visual object modifier module 2038 may modify visible content in an artificial sensory experience to alter at least one effect of the bioactive agent. In one instance and continuing with the above example, visual object modifier module 2038 may modify a visual object, such as adding window covers over the windows of a virtual plane in a virtual world designed to overcome a flying phobia to alter at least one effect of an anti-anxiety medication. In this example, the window covers may reduce anxiety experienced by the individual in addition to anxiety reduction mediated by the anti-anxiety medication. Additional examples of visible content and/or a visual object may include a virtual character (i.e., an avatar), an action performed by the avatar, and/or character attribute and/or artifact, such as facial features, weapons, clothing, a sky, and/or tools. In some instances, visual object modifier module 2038 may include a computer processor.

Further, operation 2904 illustrates modifying a color scheme of an artificial sensory experience to alter at least one effect of the bioactive agent. For example, as shown in FIGS. 18 through 21, color scheme modifier module 2040 may modify a color scheme of an artificial sensory experience to alter at least one effect of the bioactive agent. In one instance, color scheme modifier module 2040 may modify a color scheme by adding brighter background lights and colors in a virtual world designed to overcome depression to alter an effect of an inhaled anti-depression medication. Such a color scheme modification may help to overcome depression, seasonal affective disorder, and/or other disorders because it has been purported that color and/or light may affect nonvisual psychological processes. Discussion regarding the effects of color and/or light on nonvisual psychological processes may be found in Knez, *Effects of colour of light on nonvisual psychological processes*, JOURNAL OF ENVIRONMENTAL PSYCHOLOGY, 21(2):201-208 (2001); M. R Basso Jr., *Neurobiological relationships between ambient lighting and the startle response to acoustic stress in humans*, INT J NEUROSCI., 110(3-4):147-57 (2001), and Lam et al., *The Can-SAD Study: a randomized controlled trial of the effectiveness of light therapy and fluoxetine in patients with winter seasonal affective disorder*, AMERICAN JOURNAL OF PSYCHIATRY, 163(5):805-12 (2006), each incorporated by reference. In some instances, color scheme modifier module 2040 may include a computer processor.

Further, operation 2906 illustrates modifying at least a portion of text of an artificial sensory experience to alter at least one effect of the bioactive agent. For example, as shown in FIGS. 18 through 21, text modifier module 2042 may modify at least a portion of text of an artificial sensory experience to alter at least one effect of the bioactive agent. In one instance, text modifier module 2042 may modify a portion of instructional text in a virtual world, such as a computer game, to alter an effect of a bioactive agent, such as an aromatherapeutic for stress relief. In this instance, text modification may include changing the text font and/or style (e.g., size type, and/or color). Additionally, text modification may improve memory by utilizing techniques such as underlining, highlighting, boldfacing, and/or mnemonics as discussed in Carney, R. N., & Levin, J. R., *Mnemonic instruction with a focus on transfer*, JOURNAL OF EDUCATIONAL PSYCHOLOGY, 92(4):783-90, incorporated herein by reference. Another example may include instructional text providing contextual or associative information, perhaps individualized, to aid in remembering during the rest of a module. Another example of text modification and memory may include modifying the use of interactive components, e.g. via a keyboard and/or speakers, to use multiple forms of memory input, including visual, auditory, motor, and contextual. For example, this may be used to aid memory and/or in learning disorders such as dysgraphia, and/or memory disorders, such as in conjunction with memory-enhancing medications, for example cholinesterase inhibitors or herbal memory supplements. Additionally, text messages may be added and/or altered based on cognitive therapy but individualized for the person, affliction, and/or medication (e.g. an antidepressant and instructions to work toward a goal within a game that will aid in refuting automatic negative thoughts). In some instances, text modifier module 2042 may include a computer processor.

Figure 30:
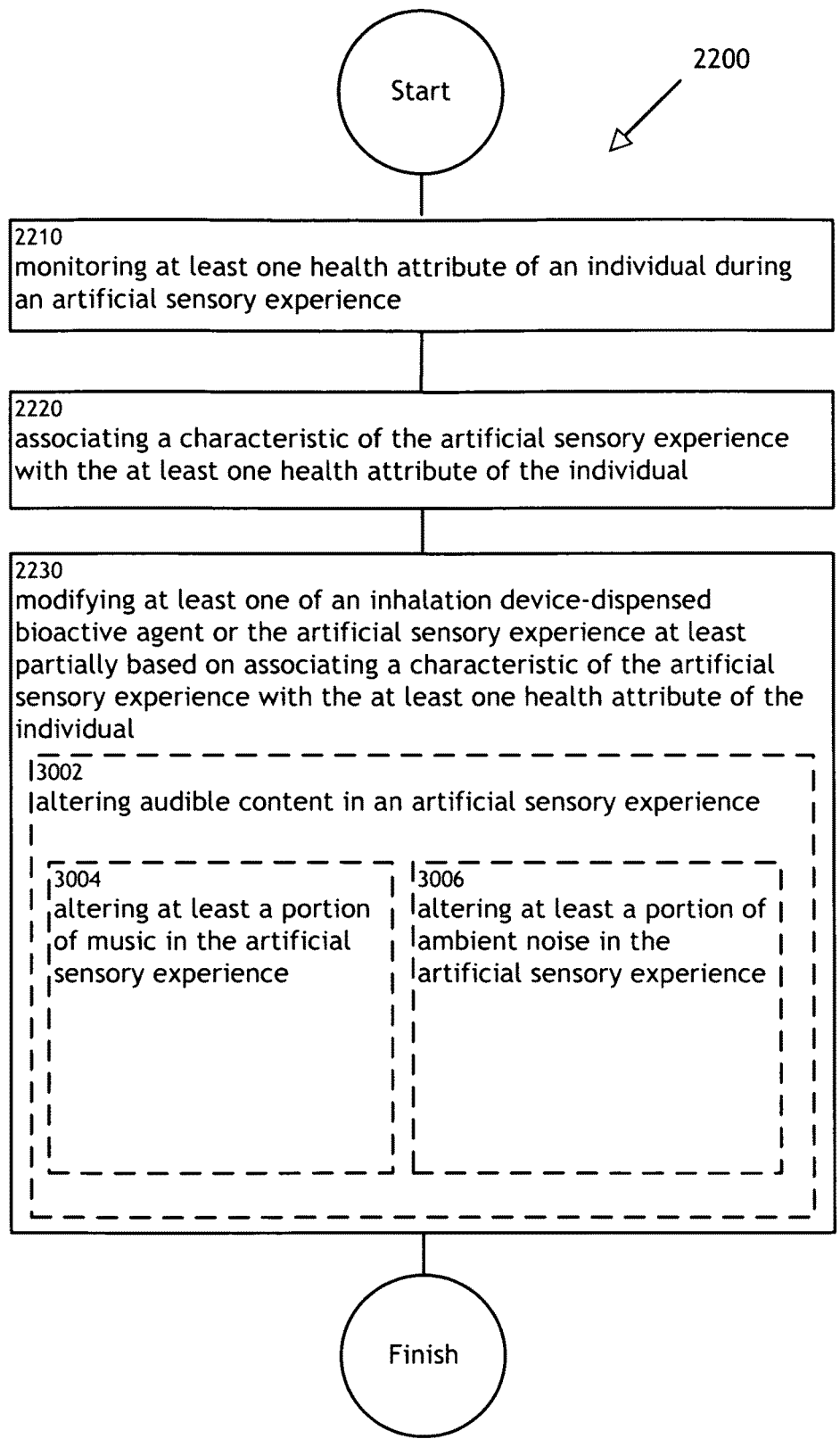
FIG. 30 illustrates an alternative embodiment of the operational flow of FIG. 22.

FIG. 30 illustrates alternative embodiments of the example operational flow 2200 of FIG. 22. FIG. 30 illustrates example embodiments where operation 2230 may include at least one additional operation. Additional operations may include operation 3002, operation 3004, and/or operation 3006.

Operation 3002 illustrates altering audible content in an artificial sensory experience. For example, as shown in FIGS. 18 through 21, sound alterer module 2044 may alter audible content in an artificial sensory experience. In one instance, sound alterer module 2044 may alter a sound in a virtual world, such as an instructor's voice tone in an instructional tutorial. This may be done as a custom-tailored feature. For example, various voice tones may be tested with an individual in order to find one that has the most significant benefit for the individual, in conjunction with an inhaled bioactive agent. In some instances, sound alterer module 2044 may include a computer processor.

Further, operation 3004 illustrates altering at least a portion of music in the artificial sensory experience. For example, as shown in FIGS. 18 through 21, music alterer module 2046 may alter at least a portion of music in the artificial sensory experience. In one instance, music alterer module 2046 may alter a portion of music including background music in an instructional tutorial. Music in the artificial sensory experience may include pitch, rhythm, tempo, meter, and articulation, dynamics, lyrics, timbre and texture. In one specific instance, music alterer module 2046 may alter a portion of uptempo music to soothing classical music in an artificial sensory experience coupled with administration of an anxiolytic. Such a music alteration may serve to provide a calming and/or relaxing environment where the effects of the anxiolytic may be facilitated. In another instance, a sound pitch may be altered to affect bone (as in healing fractures and/or promoting bone growth) and/or sinuses (including joints). Additionally, music alterer module 2046 may include providing another type of sound, such as a low frequency, to aid in heating, e.g. in conjunction with pain medication and/or an anti-inflammatory medication. In another example, the sound may originate from a natural source, for instance a purr of a cat, possibly provided at a particular pitch, to aid in relaxation, as in conjunction with a tranquilizer, and/or in healing tissue in conjunction with pain medication or anti-inflammatories. Further discussion regarding low frequency therapeutic biomechanical stimulation may be found in von Muggenthaler, E. K., *The Felid purr: low frequency therapeutic biomechanical stimulation,* 12th International Conference on Low Frequency Noise and Vibration and its Control, Bristol, UK, Sep. 18-20, 2006, Abstract located at Fauna Communications Research Institute <http://animalvoice-.com/catpurrP.htm#2pAB7.%20felid%20purr: %20A%20healing%20mechanism?%20Session: %20Tuesday%20Afternoon,%20Dec%20 04%20Time: %203:15>, and Simos et al., U.S. patent application Ser. No. 11/262,884, each incorporated herein by reference. In some instances, music alterer module 2046 may include a computer processor.

Further, operation 3006 illustrates altering at least a portion of ambient noise in the artificial sensory experience. For example, as shown in FIGS. 18 through 21, ambient noise alterer module 2048 may alter at least a portion of ambient noise in the artificial sensory experience. In one instance, ambient noise atterer module 2048 may alter the ambient noise in an artificial sensory experience including a level of white noise in the online virtual world Second Life. Ambient noise may include white noise, background noise, such as people talking, sounds naturally occurring in nature (e.g., children laughing white playing at a park), and/or room noise. Additionally, ambient noise may include abnormal, non-recurring, and/or disruptive audible content, such as gunfire. Changing the level of white noise may enhance the effect of an attention deficit drug such as Ritalin, or it may enhance the sedative properties of a steep medication or tranquilizer. Further discussion of the effects of white noise may be found in Spencer, J. A. et al., White noise and sleep induction, ARCH DIS CHILD 65(1):135-7 (1990). In some instances, ambient noise alterer module 2048 may include a computer processor.

Figure 31:
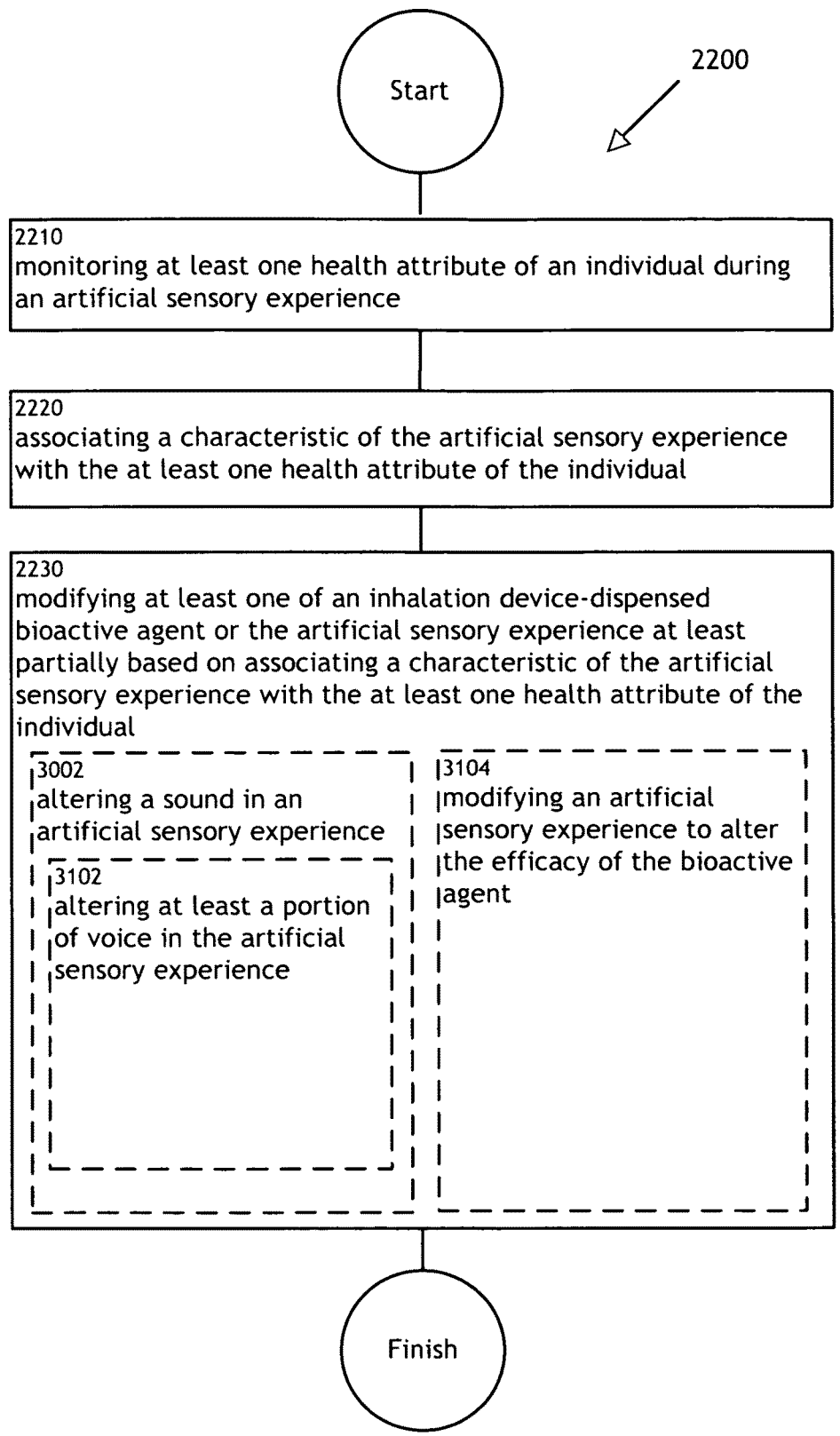
FIG. 31 illustrates an alternative embodiment of the operational flow of FIG. 22.

FIG. 31 illustrates alternative embodiments of the example operational flow 2200 of FIG. 22. FIG. 31 illustrates example embodiments where operation 2230 may include at least one additional operation. Additional operations may include operation 3102, and/or operation 3104.

Further, operation 3102 illustrates altering at Least a portion of voice in the artificial sensory experience. For example, as shown in FIGS. 18 through 21, voice alterer module 2050 may alter at least a portion of voice in the artificial sensory experience. In one instance, voice alterer module 2050 may alter a voice rhythm in an online tutorial. Such alteration may enhance the effect of an inhaled attention deficit bioactive agent, for example by elimination or reduction of monotonic qualities in the voice rhythm of the online tutorial, for example. Some examples of a voice may include a voice recording, an artificially generated voice (e.g., synthesized speech and/or voice built into animation simulations), and/or a human voice. In some instances, voice alterer module 2050 may include a computer processor.

Operation 3104 illustrates modifying an artificial sensory experience to alter the efficacy of the bioactive agent. For example, as shown in FIGS. 18 through 21, efficacy modifier module 2052 may modify an artificial sensory experience to enhance the efficacy of the bioactive agent. In one embodiment, efficacy modifier module 2052 may modify a virtual world by adding uptempo music to enhance the efficacy of an inhaled antidepressant. Further discussion of music effects may be found in Schellenberg, E. G. et al., *Exposure to music and cognitive performance: tests of children and adults*, PSYCHOLOGY OF MUSIC, Vol. 35, No. 1, 5-19 (2007), incorporated herein by reference. In some instances, efficacy modifier module 2052 may include a computer processor.

Figure 32:
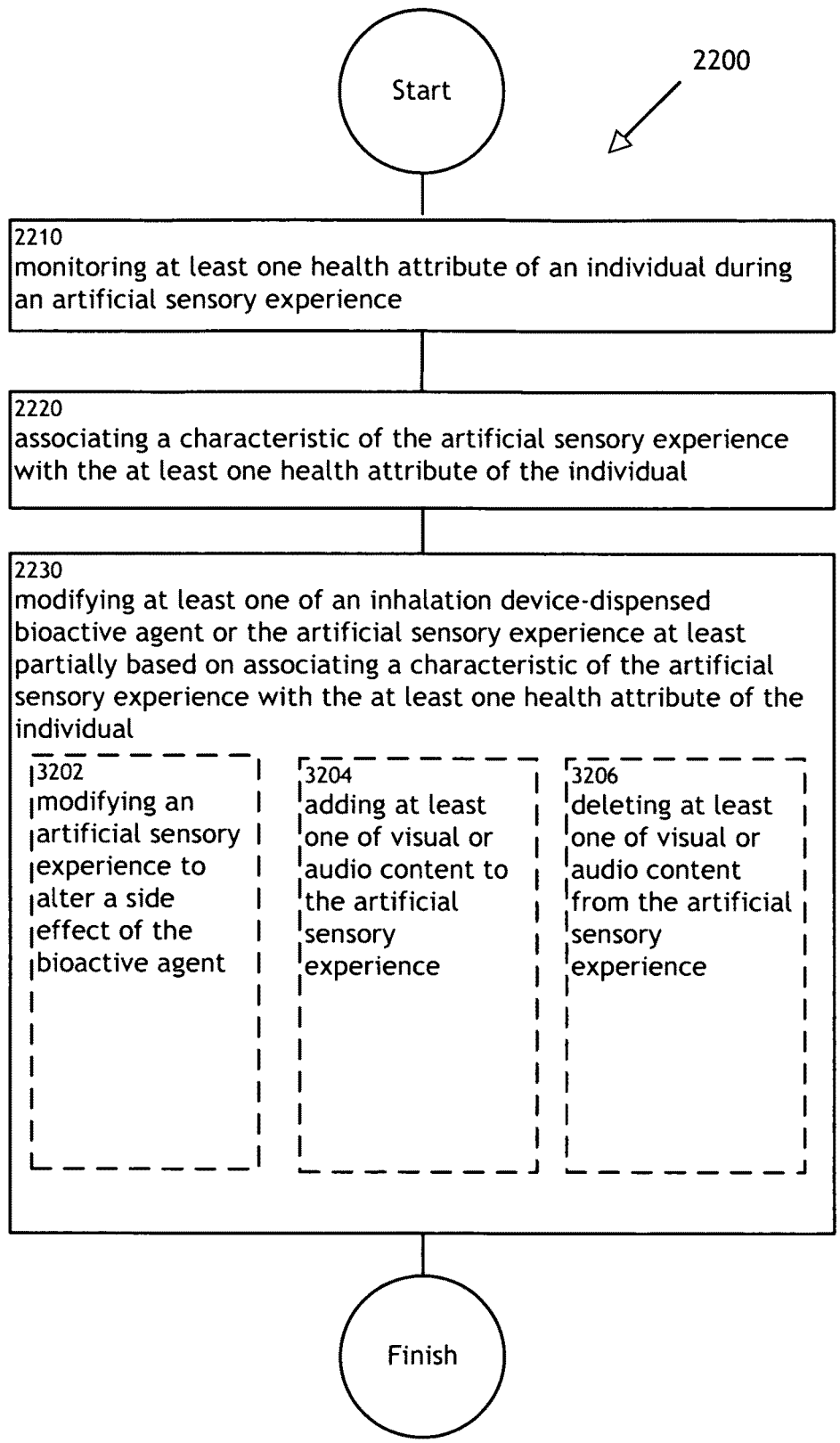
FIG. 32 illustrates an alternative embodiment of the operational flow of FIG. 22.

FIG. 32 illustrates alternative embodiments of the example operational flow 2200 of FIG. 22. FIG. 32 illustrates example embodiments where operation 2230 may include at least one additional operation. Additional operations may include operation 3202, operation 3204, and/or operation 3206.

Operation 3202 illustrates modifying an artificial sensory experience to alter a side effect of the bioactive agent. For example, as shown in FIGS. 18 through 21, side effect modifier module 2054 may modify an artificial sensory experience to alter a side effect of the bioactive agent. In one instance, side effect modifier module 2054 may modify a virtual world by adding music and/or sounds occurring in nature for reducing a side effect, such as a headache due to an administration of penicillin. Further discussion of music effects upon a side effect may be found in Siedliecki, S. L. and Good, M., *Effect of music on power, pain, depression and disability*, JOURNAL OF ADVANCED NURSING 54(5):553-562 (2006), and *Natural distractions reduce pain—study finds that sights and sounds of nature aid in pain reduction—Brief Article*, MEN'S FITNESS. October 2001, each incorporated by reference. In some instances, side effect modifier module 2054 may include a computer processor.

Operation 3204 illustrates adding at least one of visual or audio content to the artificial sensory experience. For example, as shown in FIGS. 18 through 21, adder module 2056 may add visual and/or audio content to the artificial sensory experience. In one instance, adder module 2056 may add audio content including calming music to an artificial sensory experience including a virtual world for treating stress. Adding may include increasing, creating, and/or combining content. Some examples of visual content may include visual objects, light amount and/or intensity, and or color schemes. Examples of audio content may include music, voices, artificial sounds, and/or white noise. In some instances, adder module 2056 may include a computer processor.

Operation 3206 illustrates deleting at least one of visual or audio content from the artificial sensory experience. For example, as shown in FIGS. 18 through 21, deleter module 2058 may delete at least one of visual or audio content of the artificial sensory experience. In one instance, deleter module 2058 may delete visual content including a bright lighting environment in a virtual world for enhancing the effect of a medication for a migraine headache. Deleting may include reducing and/or eliminating visual and/or audio content. In some instances, deleter module 2058 may include a computer processor.

Figure 33:
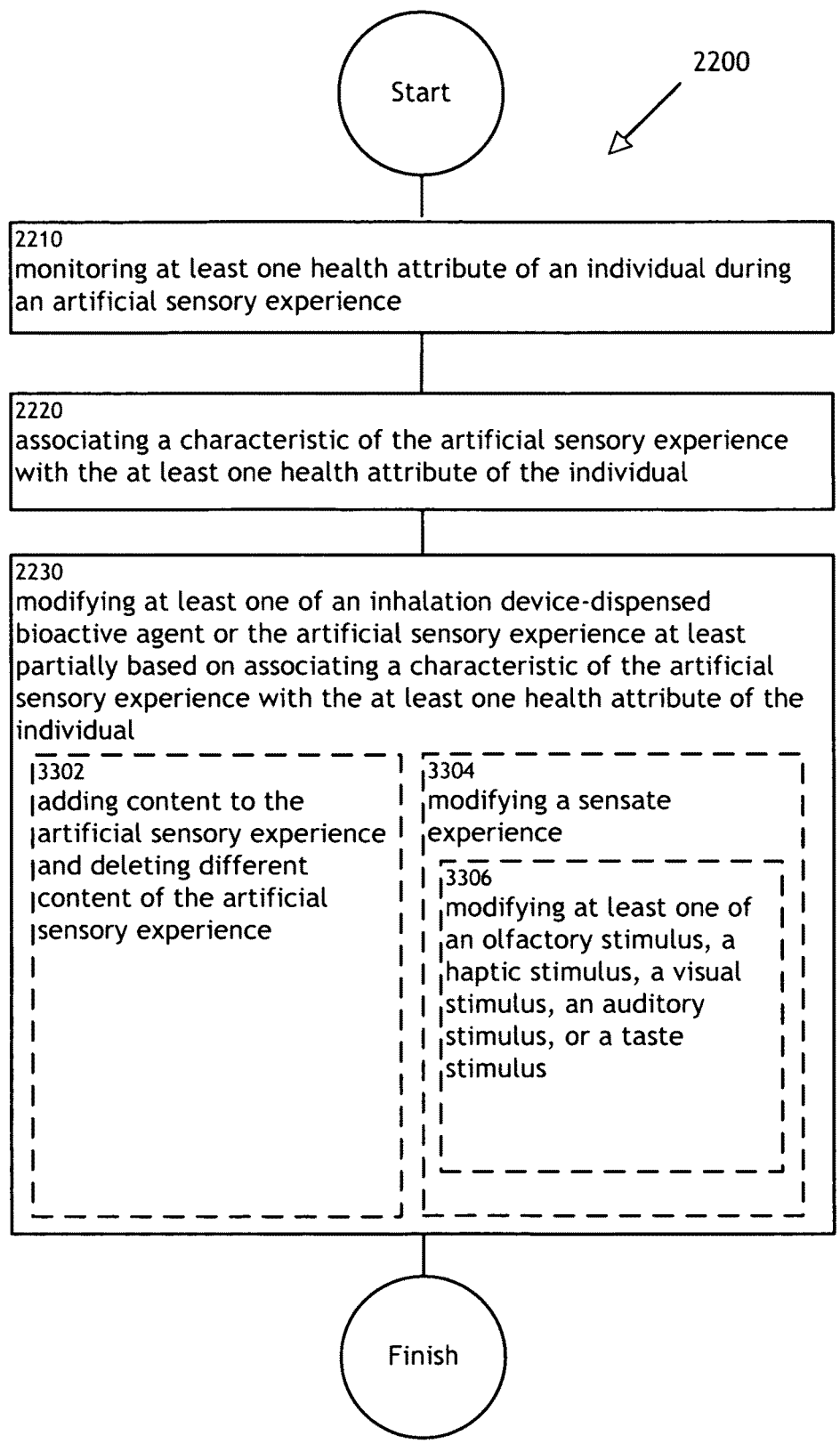
FIG. 33 illustrates an alternative embodiment of the operational flow of FIG. 22.

FIG. 33 illustrates alternative embodiments of the example operational flow 2200 of FIG. 22. FIG. 33 illustrates example embodiments where operation 2230 may include at least one additional operation. Additional operations may include operation 3302, operation 3304, and/or operation 3306.

Operation 3302 illustrates adding content to the artificial sensory experience and deleting different content of the artificial sensory experience. For example, as shown in FIGS. 18 through 21, adder module 2056 and deleter module 2058 may add content to the artificial sensory experience and delete different content of the artificial sensory experience. In one instance, adder module 2056 may add classical background music to a virtual world and deleter module 2058 may delete ambient street noise, for example, using sound detection and/or noise-cancellation technology, to enhance the effect of a sedative or other similar bioactive agent. In some instances, adder module 2056 and/or deleter module 2058 may include a computer processor.

Operation 3304 illustrates modifying a sensate experience. For example, as shown in FIGS. 18 through 21, sensate modifier module 2060 may modify a sensate experience, such as for altering at least one effect of the bioactive agent. In one instance, sensate modifier module 2060 may modify a sensate experience including adding a pleasant aroma to enhance the effect of an anxiolytic drug or other similar bioactive agent. A sensate experience may include a thing perceived by the senses, such as an aroma, a sound, a feel, a taste, and/or a sight. In some instances, sensate modifier module 2060 may include a computer processor.

Further, the operation 3306 illustrates modifying at least one of an olfactory stimulus, a haptic stimulus, a visual stimulus, an auditory stimulus, or a taste stimulus. For example, as shown in FIGS. 18 through 21, stimulus modifier module 2062 may modify at least one of an olfactory stimulus, a haptic stimulus, a visual stimulus, an auditory stimulus, or a taste stimulus. In one instance, stimulus modifier module 2062 may modify an olfactory stimulus by adding a floral aroma and/or gentle vibration to enhance a relaxing effect of a sedative or other similar bioactive agent, such as an anti-anxiety medication. Further discussion of an olfactory stimulus may be found in Shaw, D. et al., *Anxiolytic effects of lavender oil inhalation on open-field behaviour in rats*, PHYTOMEDICINE, 14(9):613-20 (2007), incorporated by reference. In some instances, stimulus modifier module 2062 may include a computer processor.

Figure 34:
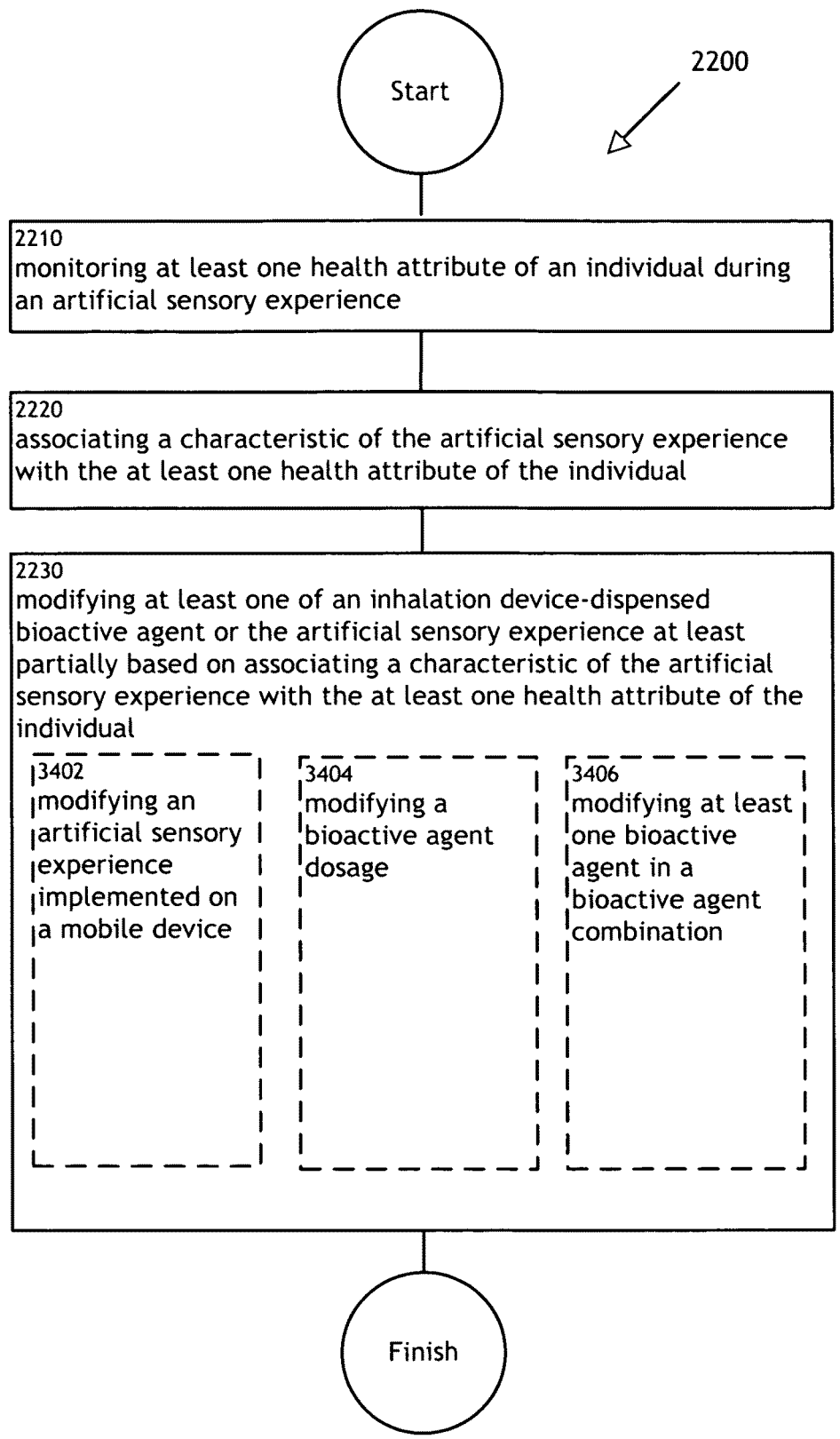
FIG. 34 illustrates an alternative embodiment of the operational flow of FIG. 22.

FIG. 34 illustrates alternative embodiments of the example operational flow 2200 of FIG. 22. FIG. 34 illustrates example embodiments where operation 2230 may include at least one additional operation. Additional operations may include operation 3402, operation 3404, and/or operation 3406.

Operation 3402 illustrates modifying an artificial sensory experience implemented on a mobile device. For example, as shown in FIGS. 18 through 21, mobile device modifier module 2064 may modify an artificial sensory experience implemented on a mobile device. In one instance, mobile device modifier module 2064 may modify a virtual world implemented in a web browser on a laptop computer having wireless capability and a battery by changing a background color theme to a brighter color theme in the virtual world. An artificial sensory experience modification, such as the color change in the above example, may enhance the effect of a bioactive agent. For example, modifying the color in the above example white an inhaled anti-depressant is bioavailable may create a more pleasant environment in the artificial sensory experience. Some examples of a mobile device may include a laptop or notebook computer, a personal digital assistant (PDA), an ipod, a smartphone, an Enterprise digital assistant (EDA), and/or a pager. In another example, mobile device modifier module 2064 may modify a city image by providing a soothing image having fewer people in the same part of the city and combining the modified image with an inhaled anti-anxiety medicine for alleviating a phobia, such as agoraphobia. In another example, mobile device modifier module 2064 may provide a stepwise procedure, with a gradually less specific procedure and/or less steps, for a compulsive patient to follow to achieve a goal for a particular outing while taking a selective serotonin reuptake inhibitor (SSRI). Data sent to or from a mobile device may be encrypted by methods known in the art to preserve the integrity of the data and the privacy of the individual's personal and medical information. In some instances, mobile device modifier module 2064 may include a computer processor.

Operation 3404 illustrates modifying a bioactive agent dosage. For example, as shown in FIGS. 18 through 21, dosage modifier module 2066 may modify a bioactive agent dosage. In one embodiment, dosage modifier module 2066 may reduce an inhaled antianxiety dose for an individual experiencing an artificial sensory experience and exhibiting a drastically reduced heart rate. Such a dosage reduction may serve to achieve a bioactive agent effective dose, reduce one or more detected side effects, and/or increase efficiency of the combination bioactive agent and artificial sensory experience. One example of reducing a bioactive agent dosage using a controller in an implanted device may be found in Shelton, U.S. Patent Publication No. 2008/0172044, which is incorporated herein by reference. In some instances, dosage modifier module 2066 may include a computer processor and/or medical instrumentation.

Operation 3406 illustrates modifying at least one bioactive agent in a bioactive agent combination. For example, as shown in FIGS. 18 through 21, bioactive agent modifier module 2068 may modify a bioactive agent in a bioactive agent combination. A bioactive agent combination may include two or more bioactive agents. One example of an inhaled bioactive agent combination may include a long acting $B_2$-agonist and a corticosteroid, further discussed in Usmani et al., *Glucocorticoid Receptor Nuclear Translocation in Airway Cells after Inhaled Combination Therapy*, AMERICAN JOURNAL OF RESPIRATORY AND CRITICAL CARE MEDICINE, 172:704-12 (2005), which is incorporated herein by reference. In some instances, bioactive agent modifier module 2068 may include a computer processor and/or medical instrumentation.

Figure 35:
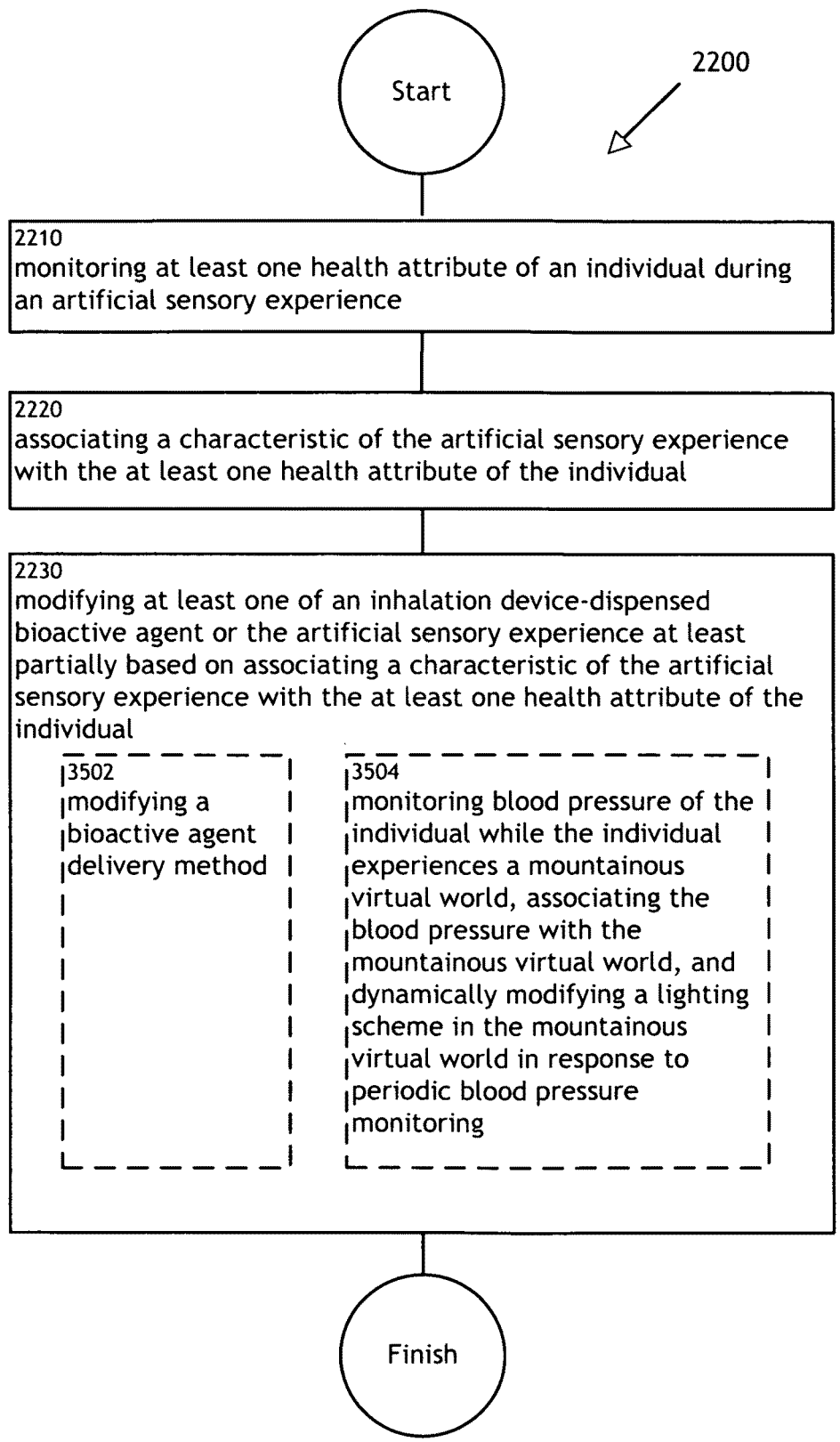
FIG. 35 illustrates an alternative embodiment of the operational flow of FIG. 22.

FIG. 35 illustrates alternative embodiments of the example operational flow 2200 of FIG. 22. FIG. 35 illustrates example embodiments where operation 2230 may include at least one additional operation. Additional operations may include operation 3502, and/or operation 3504.

Operation 3502 illustrates modifying a bioactive agent delivery method. For example, as shown in FIGS. 18 through 21, delivery modifier module 2070 may modify a bioactive agent delivery method. In one embodiment, delivery modifier module 2070 may modify an antidepressant route of administration from an inhalation collar delivery to a inhalation bracelet delivery. Some examples of bioactive delivery methods may include mucosal administration, parenterat administration (such as intravenous, intramuscular, and/or subcutaneous administration), topical administration such as epicutaneous administration, inhalational administration (e.g., inhalation collar, bracelet, tie, and/or other device configured to dispense a bioactive agent for inhalation), transdermal administration, and/or enteral therapy, such as a pill taken orally, or the like. In some instances, delivery modifier module 2070 may include a computer processor and/or a medical device.

Operation 3504 illustrates monitoring blood pressure of the individual while the individual experiences a mountainous virtual world, associating the blood pressure with the mountainous virtual world, and dynamically modifying a lighting scheme in the mountainous virtual world in response to periodic blood pressure monitoring. For example, as shown in FIGS. 18 through 21, monitorer module 2002, associater module 2016, and modifier module 2030 may monitor blood pressure of the individual while the individual experiences a mountainous virtual world, associating the blood pressure with the mountainous virtual world, and dynamically modifying a Lighting scheme in the mountainous virtual world in response to periodic blood pressure monitoring. In some instances, monitorer module 2002 may include a computer processor and/or medical instrumentation, such as an electrocardiograph. In some instances, associater module 2016 may include a computer processor. In some instances, modifier module 2030 may include a computer processor and/or medical instrumentation, such as a valve and or pump configured for pumping a bioactive agent.

Figure 36:
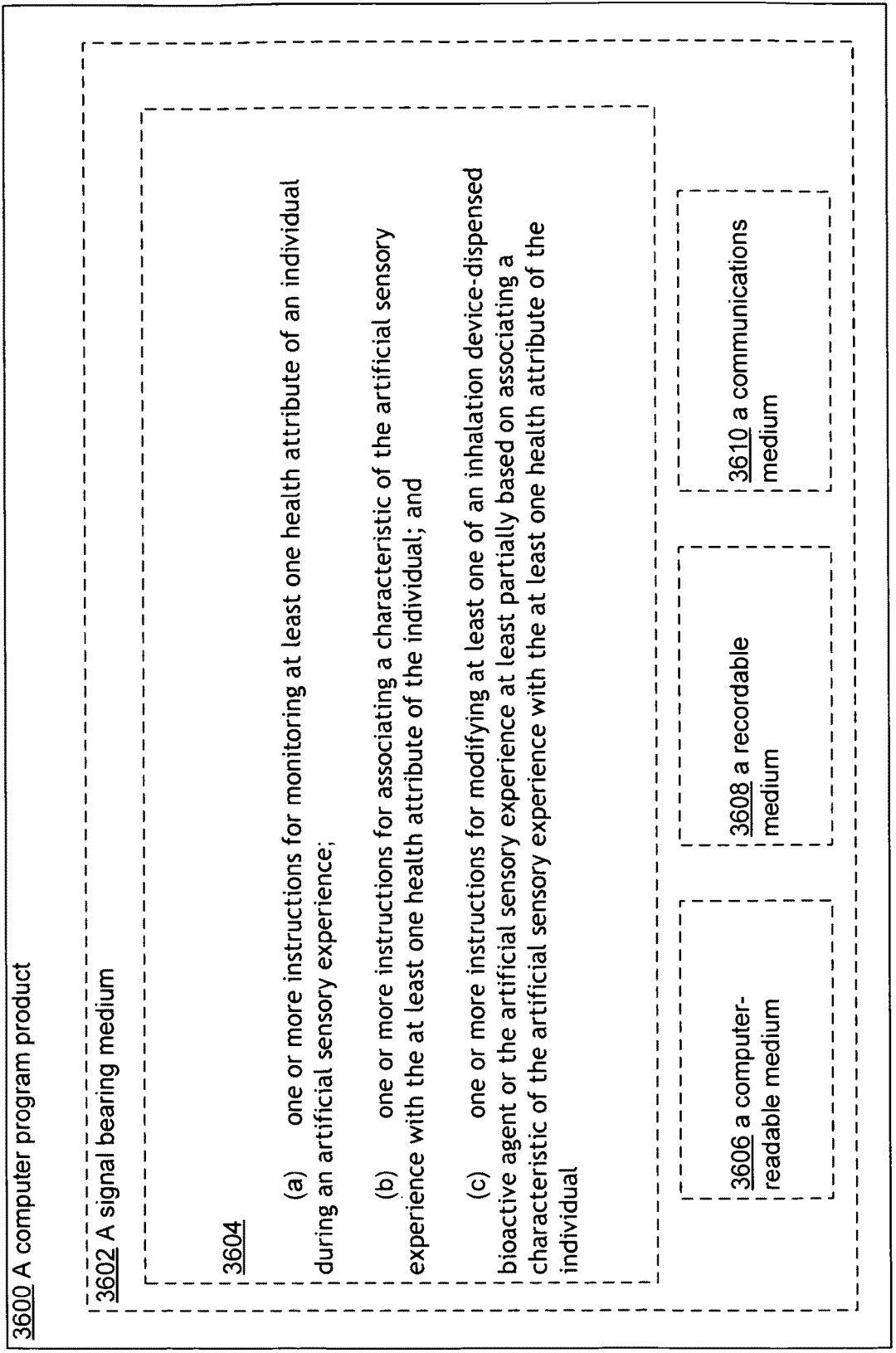
FIG. 36 illustrates a computer program product related to combining an inhaled bioactive agent and an artificial sensory experience.

FIG. 36 illustrates a partial view of an example computer program product 3600 that includes a computer program 3604 for executing a computer process on a computing device. An embodiment of the example computer program product 3600 is provided using a signal-bearing medium

3602, and may include one or more instructions for monitoring at least one health attribute of an individual during an artificial sensory experience, one or more instructions for associating a characteristic of the artificial sensory experience with the at least one health attribute of the individual, and one or more instructions for modifying at least one of an inhalation device-dispensed bioactive agent or the artificial sensory experience at least partially based on associating a characteristic of the artificial sensory experience with the at least one health attribute of the individual. The one or more instructions may be, for example, computer executable and/or logic-implemented instructions. In one implementation, the signal-bearing medium 3602 may include a computer-readable medium 3606. In one implementation, the signal bearing medium 3602 may include a recordable medium 3608. In one implementation, the signal bearing medium 3602 may include a communications medium 3610.

Figure 37:
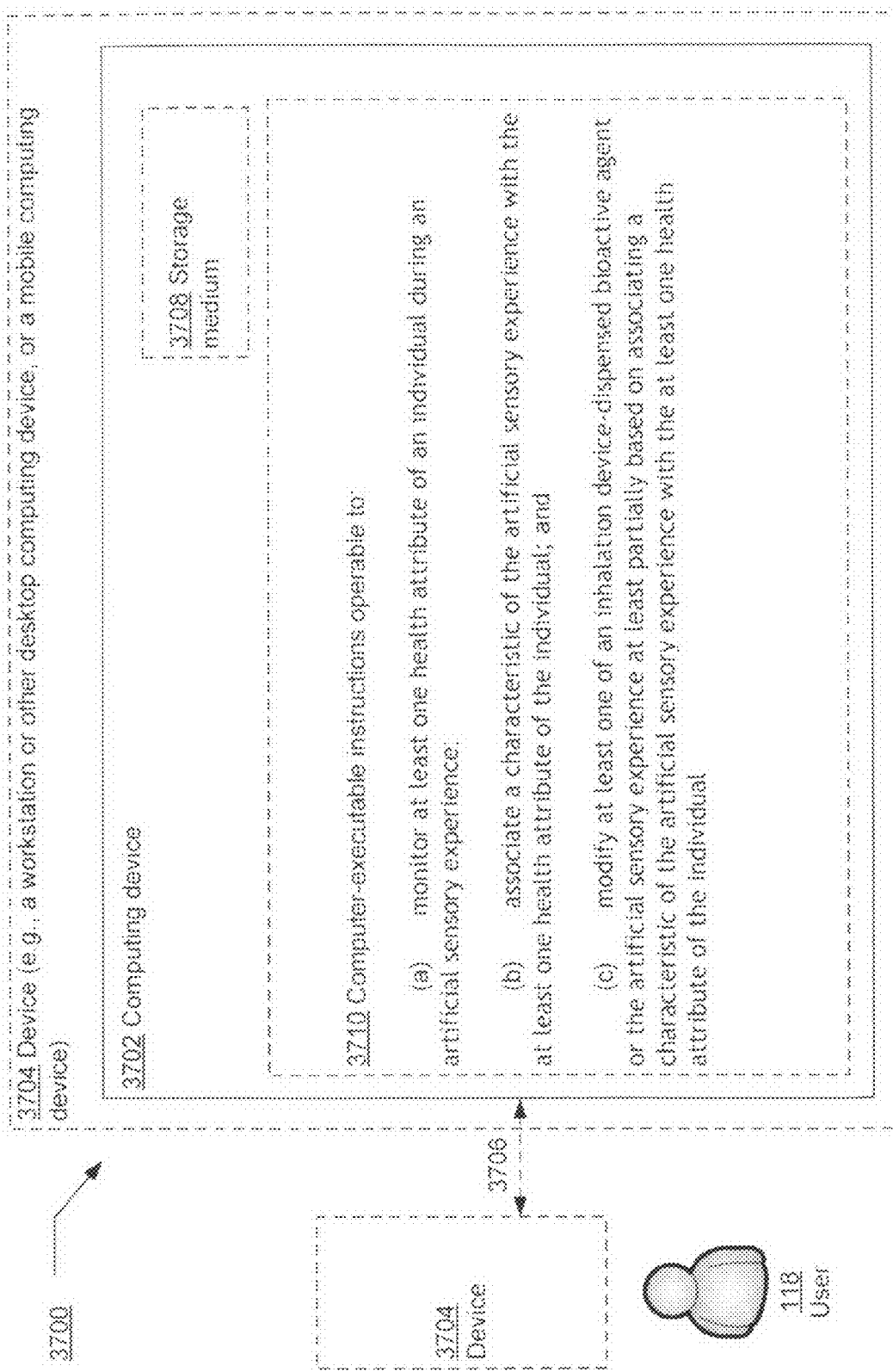
FIG. 37 illustrates a system related to combining an inhaled bioactive agent and an artificial sensory experience.

FIG. 37 illustrates an example system 3700 in which embodiments may be implemented. The system 3700 includes a computing system environment. The system 3700 also illustrates the user 118 using a device 3704, which is optionally shown as being in communication with a computing device 3702 by way of an optional coupling 3706. The optional coupling 3706 may represent a local, wide-area, or peer-to-peer network, or may represent a bus that is internal to a computing device (e.g., in example embodiments in which the computing device 3702 is contained in whole or in part within the device 3704). A storage medium 3708 may be any computer storage media.

The computing device 3702 includes computer-executable instructions 3710 that when executed on the computing device 3702 cause the computing device 3702 to monitor at least one health attribute of an individual during an artificial sensory experience, associate a characteristic of the artificial sensory experience with the at least one health attribute of the individual, and modify at least one of an inhalation device-dispensed bioactive agent or the artificial sensory experience at least partially based on associating a characteristic of the artificial sensory experience with the at least one health attribute of the individual. As referenced above and as shown in FIG. 37, in some examples, the computing device 3702 may optionally be contained in whole or in part within the device 3704.

In FIG. 37, then, the system 3700 includes at least one computing device (e.g., 3702 and/or 3704). The computer-executable instructions 3710 may be executed on one or more of the at least one computing device. For example, the computing device 3702 may implement the computer-executable instructions 3710 and output a result to (and/or receive data from) the computing device 3704. Since the computing device 3702 may be wholly or partially contained within the computing device 3704, the device 3704 also may be said to execute some or all of the computer-executable instructions 3710, in order to be caused to perform or implement, for example, various ones of the techniques described herein, or other techniques.

The device 3704 may include, for example, a portable computing device, workstation, or desktop computing device. In another example embodiment, the computing device 3702 is operable to communicate with the device 3704 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception Logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. ConsequentLy, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may Likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken Limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A atone, B atone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be Limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   a monitorer module configured to monitor at least one health attribute of an individual during at least one virtual reality experience;
   an associater module configured to associate a characteristic of the at least one virtual reality experience with the at least one health attribute of the individual; and
   a modifier module configured to modify at least one of an inhalation device-dispensed bioactive agent or at least a portion of the at least one virtual reality experience at least partially based on associating a characteristic of the at least one virtual reality experience with the at least one health attribute of the individual,
   wherein at least one of the monitorer module, the associater module or the modifier module is at least partially implemented using hardware.

2. The system of claim 1, wherein the monitorer module configured to modify at least one of an inhalation device-dispensed bioactive agent or at least a portion of the at least one virtual reality experience at least partially based on associating a characteristic of the at least one virtual reality experience with the at least one health attribute of the individual comprises:
   a data receiver module configured to receive data from an automated medical device.

3. The system of claim 1, wherein the monitorer module configured to modify at least one of an inhalation device-dispensed bioactive agent or at least a portion of the at least one virtual reality experience at least partially based on associating a characteristic of the at least one virtual reality experience with the at least one health attribute of the individual comprises:
   a health attribute monitorer module configured to monitor at least one of physical activity, body weight, body mass index number, heart rate, blood oxygen level, or blood pressure temporally associated with the at least one virtual reality experience.

4. The system of claim 1, wherein the monitorer module configured to modify at least one of an inhalation device-dispensed bioactive agent or at least a portion of the at least one virtual reality experience at least partially based on associating a characteristic of the at least one virtual reality experience with the at least one health attribute of the individual comprises:
   a neurophysiological monitorer module configured to monitor a neurophysiological activity.

5. The system of claim 4, wherein the neurophysiological monitorer module configured to monitor a neurophysiological activity comprises:
   a neurophysiological measurer module configured to measure at least one physiologic activity using at least one of electroencephalography, computed axial tomography, positron emission tomography, magnetic resonance imaging, functional magnetic resonance imaging, functional near-infrared imaging, or magnetoencephalography.

6. The system of claim 1, wherein the monitorer module configured to modify at least one of an inhalation device-dispensed bioactive agent or at least a portion of the at least one virtual reality experience at least partially based on associating a characteristic of the at least one virtual reality experience with the at least one health attribute of the individual comprises:
   a recorder module configured to record at least one monitored health attribute of the individual.

7. The system of claim 1, wherein the monitorer module configured to modify at least one of an inhalation device-dispensed bioactive agent or at least a portion of the at least one virtual reality experience at least partially based on associating a characteristic of the at least one virtual reality experience with the at least one health attribute of the individual comprises:
- an observer module configured to observe at least one indication of an expected behavior pattern proximate in time to a characteristic of the at least one virtual reality experience.

8. The system of claim 1, wherein the associater module configured to associate a characteristic of the at least one virtual reality experience with the at least one health attribute of the individual comprises:
- a physiological response associater module configured to associate a characteristic of the at least one virtual reality experience with at least one physiological response of the individual.

9. The system of claim 8, wherein the physiological response associater module configured to associate a characteristic of the at least one virtual reality experience with at least one physiological response of the individual comprises:
- an artificial sensory experience associater module configured to associate at least one of an object, an action, an avatar, or an environment of the at least one virtual reality experience with at least one physiological response of the individual.

10. The system of claim 8, wherein the physiological response associater module configured to associate a characteristic of the at least one virtual reality experience with at least one physiological response of the individual comprises:
- a health attribute associater module configured to associate a characteristic of the at least one virtual reality experience with at least one of blood pressure, pulse, pupil dilation, respiration rate, skin response, or voice response of the individual.

11. The system of claim 1, wherein the associater module configured to associate a characteristic of the at least one virtual reality experience with the at least one health attribute of the individual comprises:
- a report accepter module configured to accept a report from the individual of an association of a characteristic of the at least one virtual reality experience and the at least one health attribute.

12. The system of claim 1, wherein the associater module configured to associate a characteristic of the at least one virtual reality experience with the at least one health attribute of the individual comprises:
- a utilizer module configured to utilize an algorithm configured to correlate at least one virtual reality characteristic with at least one health attribute.

13. The system of claim 1, wherein the associater module configured to associate a characteristic of the at least one virtual reality experience with the at least one health attribute of the individual comprises:
- a comparer module configured to compare current measured behavior with expected behavior data that is correlated with the at least one virtual reality experience.

14. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
- an access modifier module configured to modify access to at least a portion of the at least one virtual reality experience.

15. The system of claim 14, wherein the access modifier module configured to modify access to at least a portion of the at least one virtual reality experience comprises:
- a restricter module configured to restrict access to at least a portion of the at least one virtual reality experience.

16. The system of claim 14, wherein the access modifier module configured to modify access to at least a portion of the virtual world comprises:
- a granter module configured to grant access to at least a portion of the at least one virtual reality experience.

17. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
- a visual object modifier module configured to modify visible content in the at least one virtual reality experience to alter at least one effect of the bioactive agent.

18. The system of claim 17, wherein the visual object modifier module configured to modify visible content in at least one virtual reality experience to alter at least one effect of the bioactive agent comprises:
- a color scheme modifier module configured to modify a color scheme of the at least one virtual reality experience to alter at least one effect of the bioactive agent.

19. The system of claim 17, wherein the visual object modifier module configured to modify visible content in at least one virtual reality experience to alter at least one effect of the bioactive agent comprises:
- a text modifier module configured to modify at least a portion of text of the at least one virtual reality experience to alter at least one effect of the bioactive agent.

20. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
- a sound alterer module configured to alter audible content in the at least one virtual reality experience.

21. The system of claim 20, wherein the sound alterer module configured to alter audible content in at least one virtual reality experience comprises:
- a music alterer module configured to alter at least a portion of music in the at least one virtual reality experience.

22. The system of claim 20, wherein the sound alterer module configured to alter audible content in at least one virtual reality experience comprises:
- an ambient noise alterer module configured to alter at least a portion of ambient noise in the at least one virtual reality experience.

23. The system of claim 20, wherein the sound alterer module configured to alter audible content in at least one virtual reality experience comprises:
- a voice alterer module configured to alter at least a portion of voice in the at least one virtual reality experience.

24. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    an efficacy modifier module configured to modify the at least one virtual reality experience to alter the efficacy of the bioactive agent.

25. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    a side effect modifier module configured to modify the at least one virtual reality experience to alter a side effect of the bioactive agent.

26. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    an adder module configured to add at least one of visual or audio content to the at least one virtual reality experience.

27. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    a deleter module configured to delete at least one of visual or audio content from the at least one virtual reality experience.

28. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    a sensate modifier module configured to modify a sensate experience.

29. The system of claim 28, wherein the sensate modifier module configured to modify a sensate experience comprises:
    a stimulus modifier module configured to modify at least one of an olfactory stimulus, a haptic stimulus, a visual stimulus, an auditory stimulus, or a taste stimulus.

30. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    a mobile device modifier module configured to modify at least one virtual reality experience implemented on a mobile device.

31. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    a dosage modifier module configured to modify a bioactive agent dosage.

32. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    a bioactive agent modifier module configured to modify at least one bioactive agent in a bioactive agent combination.

33. The system of claim 1, wherein the modifier module configured to modify at least one of an inhalation device-dispensed bioactive agent or at least a portion of the at least one virtual reality experience at least partially based on associating a characteristic of the at least one virtual reality experience with the at least one health attribute of the individual comprises:
    a delivery modifier module configured to modify a bioactive agent delivery method.

34. The system of claim 1, wherein the monitorer module configured to monitor at least one health attribute of an individual during at least one virtual reality experience comprises:
    a monitorer module configured to monitor at least one attribute related to a central nervous system of an individual during the at least one virtual reality experience.

35. The system of claim 1, wherein the monitorer module configured to monitor at least one health attribute of an individual during at least one virtual reality experience, the associater module configured to associate a characteristic of the at least one virtual reality experience with at the at least one health attribute of the individual, and the modifier module configured to modify at least one of an inhalation device-dispensed bioactive agent or at least a portion of the at least one virtual reality experience at least partially based on associating a characteristic of the at least one virtual reality experience with the at least one health attribute of the individual comprise:
    a monitorer module configured to monitor at least one health attribute of an individual during an artificial sensory experience;
    an associater module configured to associate a characteristic of the artificial sensory experience with the at least one health attribute of the individual; and
    a modifier module configured to modify at least one of an inhalation device-dispensed bioactive agent or at least a portion of the artificial sensory experience at least partially based on associating a characteristic of the artificial sensory experience with the at least one health attribute of the individual.

36. The system of claim 1, wherein the monitorer module configured to monitor at least one health attribute of an individual during at least one virtual reality experience, the associater module configured to associate a characteristic of the at least one virtual reality experience with at the at least one health attribute of the individual, and the modifier module configured to modify at least one of an inhalation device-dispensed bioactive agent or at least a portion of the at least one virtual reality experience at least partially based on associating a characteristic of the at least one virtual reality experience with the at least one health attribute of the individual comprise:
    a monitorer module configured to monitor at least one attribute related to a central nervous system of an individual during an artificial sensory experience;

an associater module configured to associate a characteristic of the artificial sensory experience with the at least one attribute related to a central nervous system of the individual; and a modifier module configured to modify at least one of an inhalation device-dispensed bioactive agent or at least a portion of the artificial sensory experience at least partially based on associating a characteristic of the artificial sensory experience with the at least one attribute related to a central nervous system of the individual.

37. The system of claim 1, wherein the monitorer module configured to monitor at least one health attribute of an individual during at least one virtual reality experience comprises:

a monitorer module configured to monitor at least one health attribute of an individual during at least one of an artificial sensory experience, a virtual world, a massively multiplayer online game, a learning tutorial, a computer-based simulated environment, a text-based chat room, a picture chat, an instant messaging application, an online class, an internet marketplace, a computer conferencing, an online game, a single player game, a networked game, a video game, an interactive experience including at least a religious ceremony, an interactive experience including at least a combat training exercise, a screen recording, a written document, an audio file, a virtual scent environment, an interactive experience including at least a secular ceremony, a social networking environment, an online learning environment, an online educational experience, an online shopping environment, or an online medical information environment.

38. A computer program product, comprising:

at least one non-transitory computer readable medium including at least:

one or more instructions for monitoring at least one health attribute of an individual during at least one virtual reality experience;

one or more instructions for associating a characteristic of the at least one virtual reality experience with the at least one health attribute of the individual; and one or more instructions for modifying at least one of an inhalation device-dispensed bioactive agent or at least a portion of the at least one virtual reality experience at least partially based on associating a characteristic of the at least one virtual reality experience with the at least one health attribute of the individual.

39. A system, comprising:

circuitry for monitoring at least one health attribute of an individual during at least one virtual reality experience;

circuitry for associating a characteristic of the at least one virtual reality experience with the at least one health attribute of the individual; and circuitry for modifying at least one of an inhalation device-dispensed bioactive agent or at least a portion of the at least one virtual reality experience at least partially based on associating a characteristic of the at least one virtual reality experience with the at least one health attribute of the individual.

* * * * *